United States Patent
Koike et al.

(10) Patent No.: US 9,963,443 B2
(45) Date of Patent: May 8, 2018

(54) RADIOLABELED COMPOUNDS

(71) Applicant: TAKEDA PHARMACEUTICAL COMPANY LIMITED, Osaka (JP)

(72) Inventors: Tatsuki Koike, Kanagawa (JP); Shuhei Ikeda, Kanagawa (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days. days.

(21) Appl. No.: 15/316,937

(22) PCT Filed: Jun. 8, 2015

(86) PCT No.: PCT/JP2015/067100
§ 371 (c)(1),
(2) Date: Dec. 7, 2016

(87) PCT Pub. No.: WO2015/190613
PCT Pub. Date: Dec. 17, 2015

(65) Prior Publication Data
US 2017/0114042 A1    Apr. 27, 2017

Related U.S. Application Data

(60) Provisional application No. 62/009,526, filed on Jun. 9, 2014.

(51) Int. Cl.
| | | |
|---|---|---|
| *A61K 31/506* | (2006.01) | |
| *C07D 401/14* | (2006.01) | |
| *A61K 51/04* | (2006.01) | |
| *C07D 401/04* | (2006.01) | |
| *C07D 405/14* | (2006.01) | |
| *C07D 417/14* | (2006.01) | |

(52) U.S. Cl.
CPC ........ *C07D 401/14* (2013.01); *A61K 51/0455* (2013.01); *A61K 51/0459* (2013.01); *C07D 401/04* (2013.01); *C07D 405/14* (2013.01); *C07D 417/14* (2013.01); *C07B 2200/05* (2013.01)

(58) Field of Classification Search
CPC .. A61K 31/506; C07D 403/12; C07D 473/00; C07D 473/16; C07D 473/24; C07D 473/30; C07D 473/32; C07D 473/34; C07D 473/38; C07D 473/40; C07D 487/04; C12N 9/1205; C12N 9/99; C12Y 207/01137
See application file for complete search history.

(56) References Cited

U.S. PATENT DOCUMENTS

| | | | | |
|---|---|---|---|---|
| 9,169,243 | B2 * | 10/2015 | Notte | A61K 31/4439 |
| 9,598,398 | B2 * | 3/2017 | Koike | C07D 403/12 |
| 9,624,170 | B2 * | 4/2017 | Koike | C07D 403/04 |
| 9,643,957 | B2 * | 5/2017 | Koike | C07D 403/12 |
| 2009/0029949 | A1 * | 1/2009 | Parrill-Baker | G06F 19/706 514/120 |
| 2011/0312941 | A1 * | 12/2011 | Batt | C07D 487/04 514/215 |
| 2013/0090341 | A1 | 4/2013 | Koike et al. | |
| 2014/0088118 | A1 | 3/2014 | Koike et al. | |
| 2014/0088146 | A1 | 3/2014 | Koike et al. | |
| 2014/0228373 | A1 | 8/2014 | Koike et al. | |
| 2015/0266872 | A1 | 9/2015 | Koike et al. | |
| 2015/0315209 | A1 * | 11/2015 | Koike | C07D 401/14 514/210.16 |
| 2015/0376205 | A1 | 12/2015 | Koike et al. | |
| 2016/0024049 | A1 | 1/2016 | Koike et al. | |
| 2016/0052897 | A1 | 2/2016 | Koike et al. | |
| 2016/0318922 | A1 * | 11/2016 | Notte | A61K 31/4439 |

FOREIGN PATENT DOCUMENTS

| | | | | |
|---|---|---|---|---|
| CA | 2 894 492 | | 6/2014 | |
| WO | WO 2004078732 A1 * | | 9/2004 | ........... C07D 207/34 |
| WO | 2010/110400 | | 9/2010 | |
| WO | 2013/054822 | | 4/2013 | |
| WO | 2014/061676 | | 4/2014 | |
| WO | 2014/092100 | | 6/2014 | |
| WO | 2014/163161 | | 10/2014 | |
| WO | 2014/163162 | | 10/2014 | |

OTHER PUBLICATIONS

International Search Report dated Aug. 20, 2015 in International (PCT) Application No. PCT/JP2015/067100.

* cited by examiner

*Primary Examiner* — Alexander R Pagano
(74) *Attorney, Agent, or Firm* — Wenderoth, Lind & Ponack, L.L.P.

(57) ABSTRACT

The present invention provides radiolabeled compounds useful as radiotracers for quantitative imaging of CH24H in mammals. The compound of the present invention is represented by the formula (I): wherein each symbol is as defined in the specification.

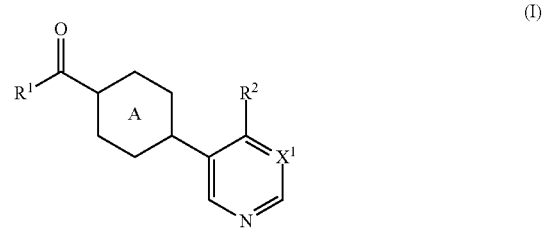

20 Claims, 1 Drawing Sheet
(1 of 1 Drawing Sheet(s) Filed in Color)

SEQUENCE LISTING

```
<160> NUMBER OF SEQ ID NOS: 2

<210> SEQ ID NO 1
<211> LENGTH: 26
<212> TYPE: DNA
<213> ORGANISM: Artificial
<220> FEATURE:
<223> OTHER INFORMATION: PCR primer

<400> SEQUENCE: 1
gccccggagc catgagcccc gggctg                                        26

<210> SEQ ID NO 2
<211> LENGTH: 26
<212> TYPE: DNA
<213> ORGANISM: Artificial
<220> FEATURE:
<223> OTHER INFORMATION: PCR primer

<400> SEQUENCE: 2
gtcctgcctg gaggccccct cagcag                                        26
```

RADIOLABELED COMPOUNDS

TECHNICAL FIELD

The invention relates generally to novel radiolabeled compounds and to their use as radiotracers for determination of the binding occupancy of a cholesterol 24-hydroxylase (in the present specification, sometimes to be abbreviated as "CH24H") enzyme ligand at the CH24H enzyme or for diagnostic imaging.

BACKGROUND OF THE INVENTION

Noninvasive, nuclear imaging techniques can be used to obtain basic and diagnostic information about the physiology and biochemistry of a variety of living subjects including experimental animals, normal humans and patients. These techniques rely on the use of sophisticated imaging instrumentation that is capable of detecting radiation emitted from radiotracers administered to such living subjects. The information obtained can be reconstructed to provide planar and tomographic images that reveal distribution of the radiotracer as a function of time. Use of appropriately designed radiotracers can result in images which contain information on the structure, function and most importantly, the physiology and biochemistry of the subject. Much of this information cannot be obtained by other means. The radiotracers used in these studies are designed to have defined behaviors in vivo which permit the determination of specific information concerning the physiology or biochemistry of the subject or the effects that various diseases or drugs have on the physiology or biochemistry of the subject. Currently, radiotracers are available for obtaining useful information concerning such things as cardiac function, myocardial blood flow, lung perfusion, liver function, brain blood flow, tumor imaging, regional brain glucose and oxygen metabolism.

Compounds can be labeled with either positron or gamma emitting radionuclides. For imaging, the most commonly used positron emitting (PET) radionuclides are $^{11}C$, $^{18}F$, $^{15}O$ and $^{13}N$, all of which are accelerator produced, and have half lives of 20, 110, 2 and 10 minutes, respectively. Since the half-lives of these radionuclides are so short, it is only feasible to use them at institutions that have an accelerator on site or very close by for their production, thus limiting their use. Several gamma emitting radiotracers are available which can be used by essentially any hospital in the U.S. and in most hospitals worldwide. The most widely used of these are $^{99m}TC$, $^{201}Tl$ and $^{123}I$.

In the last two decades, one of the most active areas of nuclear medicine research has been the development of receptor imaging radiotracers. These tracers bind with high affinity and specificity to selective receptors and neuroreceptors. Successful examples include radiotracers for imaging the following receptor or transporter systems: estrogen, muscarinic, serotonin, dopamine, opiate, neuropeptide-Y, cannabinoid-1 and neurokinin-1.

Alzheimer's disease is a progressive neurodegenerative disease characterized by the deposition of amyloid β protein (Aβ), accumulation of phosphorylated tau in a nerve cell (neurofibrillary tangle), and nerve cell death. In recent years, the number of patients with Alzheimer's disease is increasing because of aging, but an effective treatment method has not been developed as yet. The therapeutic drugs for Alzheimer's disease which are currently used in the medical practice are mainly acetylcholinesterase (AchE) inhibitors. While AchE inhibitors is confirmed to provide a certain level of usefulness, since they are used with the aim of supplementing decreased acetylcholine, the treatment with AchE inhibitor is merely a symptomatic therapy. Thus, the prompt development of a basic remedy and prophylactic drug has been strongly desired.

It has been clarified that the presence of allele ε4 of apolipoprotein E (ApoE) controlling the cholesterol metabolism is a strong risk factor of Alzheimer's disease (Science, vol. 261, 921-923, 1993). After this finding, the correlation between plural gene polymorphisms playing a role in the expression of protein controlling the cholesterol metabolism and the onset frequency of Alzheimer's disease has been shown, suggesting the correlation between the cholesterol metabolism and Alzheimer's disease (Neurobiol. Aging, vol. 24, 421-426, 2003; Mol. Psychiatry, vol. 8, 635-638, 2003). Moreover, it has been reported that a polymorphism in the gene of Cyp46 (same as "cholesterol 24-hydroxylase (CH24H)"), which is cholesterol oxidase specifically expressed in the brain, is a risk factor of Alzheimer's disease (Neurosci. Lett., vol. 328, pages 9-12, 2002). Furthermore, it has also been reported that Cyp46 (CH24H) is expressed in the vicinity of deposited amyloid in Alzheimer's disease patients (J. Biol. Chem., vol. 279, pages 34674-34681, 2004), 24S-hydroxycholesterol (24-HC), which is a metabolite thereof, increases in the brain spinal cord fluid (CSF) of Alzheimer's disease patients (Neurosci. Lett., vol. 324, pages 83-85, 2002; Neurosci. Lett., vol. 397, pages 83-87, 2006), 24-HC induces cell death of SH-SY5Y cell, which is a human neuroblast line (Brain Res., vol. 818, pages 171-175, 1999), and rats in which 24-HC was injected into the lateral cerebral ventricle showed impaired short-term memory, which is commonly observed in Alzheimer's disease, suggesting that hippocampal neurons were damaged by 24-HC (Neuroscience, vol. 164, pages 398-403, 2009). These findings suggest that Cyp46 (CH24H) is deeply involved in the pathology of Alzheimer's disease. Therefore, a compound that inhibits the Cyp46 (CH24H) activity (i.e., Cyp46 (CH24H) inhibitor) suppresses neuronal cell death, increase in Aβ, intracerebral inflammation and the like observed in Alzheimer's disease, by decreasing intracerebral 24-HC, and is promising as a therapeutic or prophylactic drug showing not only an improvement of symptoms but also a suppression of progression. Moreover, it has been reported that an AchE inhibitor clinically used as a therapeutic drug for Alzheimer's disease shows an improvement effect on memory disorders induced by Aβ in mouse (British Journal of Pharmacology, vol. 149, pages 998-1012, 2006). Thus, a Cyp46 (CH24H) inhibitor is promising as a new therapeutic or prophylactic drug for Alzheimer's disease.

As a concept of the preclinical stage of Alzheimer's disease, a mild cognitive impairment has been proposed, and about half of those having this disorder is said to progress into the Alzheimer's disease in the future. In recent years, it has been reported that 24-HC increases not only in patients with Alzheimer's disease but also in CSF of patients with mild cognitive impairment (Neurosci. Lett., vol. 397, pages 83-87, 2006). This finding suggests that Cyp46 (CH24H) is involved in the pathology of mild cognitive impairment, and therefore, a Cyp46 (CH24H) inhibitor is promising as a new therapeutic drug for Alzheimer's disease or a prophylactic drug for the progression into the Alzheimer's disease.

In recent years, moreover, it has been reported that 24-HC in the blood increases before expression of the symptom in an autoimmune encephalomyelitis model, which is an animal model of multiple sclerosis which is one of the demyelination diseases in the central nervous system (J. Neurosci.

Res., vol. 85, pages 1499-1505, 2007). Multiple sclerosis is often developed in younger people of about 30 years old, and scarcely developed in the elderly of 60 years or older. It has also been reported that 24-HC in the blood increases in multiple sclerosis patients aged from 21 to 50 (Neurosci. Lett., vol. 331, pages 163-166, 2002). These findings suggest that Cyp46 (CH24H) is involved in the pathology of multiple sclerosis, and therefore, a Cyp46 (CH24H) inhibitor is promising as a new therapeutic or prophylactic drug for multiple sclerosis.

Traumatic brain injury (also referred to as TBI in the present specification) is a condition having an extremely harmful influence on the personal health, for which no effective cure has been established. In the repair process following tissue damage by TBI, reconstruction of neuronal cell membrane and distribution of intracerebral cholesterol along with the growth of glial cell are suggested to be activated (Proc. Natl. Acad. Sci. USA, vol. 102, pages 8333-8338, 2005). In a rat TBI model, an enhanced expression of Cyp46 (CH24H) after trauma has been reported (J. Neurotrauma, vol. 25, pages 1087-1098, 2008). Moreover, it has also been reported that 24-HC is injurious to neuronal cells (Brain Res., vol. 818, pages 171-175, 1999). Therefore, a Cyp46 (CH24H) inhibitor is promising as a new therapeutic or prophylactic drug for TBI.

As a pathological significance of 24-HC in neurodegenerative diseases, an inflammatory gene expression-enhancing action in neuronal cells has been reported (NeuroReport, vol. 16, pages 909-913, 2005). In addition, it is suggested that an intracerebral inflammation reaction accompanied by activation of glial cell is a pathological change characteristic of neurodegenerative diseases (Glia, vol. 50, pages 427-434, 2005). In recent years, an effectiveness of therapy by suppression of intracerebral inflammation has also been reported for neurodegenerative diseases such as Huntington's disease, Parkinson's disease and amyotrophic lateral sclerosis and the like (Mol. Neurodegeneration, vol. 4, pages 47-59, 2009). Furthermore, 24-HC has recently been suggested to be an endogenous activator of the N-methyl-d-aspartate (NMDA) receptor, whose over-activation is thought play a key role in the glutamate toxicity (J. Neurosci., vol. 33, pages 17290-17300, 2013). Therefore, with a mechanism to regulate intracerebral inflammation and/or glutamatergic transmission, pharmacological reduction of 24-HC by the inhibition of Cyp46 (CH24H) is promising as a new therapeutic or prophylactic drug for neurological diseases such as Huntington's disease, Parkinson's disease, cerebral infarction, glaucoma, amyotrophic lateral sclerosis, epilepsy syndromes and the like.

Glaucoma is the main cause of blindness, and is considered to be a serious social problem. However, there is no effective cure of a normal intraocular pressure type-visual field constriction, which is the major symptom of the disease. In recent years, it has been reported that gene polymorphisms of Cyp46 (CH24H) associated with high value of 24-HC in blood is related to the risk of the onset of glaucoma (Invest. Ophthalmol. Vis. Sci., vol. 50, pages 5712-5717, 2009). Thus, a Cyp46 (CH24H) inhibitor is promising as a therapeutic or prophylactic drug for glaucoma.

Seizure is a disorder that convulsively occurs with abnormal electrical excitation of neuronal cell in the brain. Seizure is one of the characteristic clinical findings of Alzheimer's disease (Epilepsia, vol. 47, pages 867-872, 2006), and the relationship between epilepsy and onset of Alzheimer's disease has been indicated (Epilepsia, vol. 52, Supplement 1, pages 39-46, 2011). It has been reported that seizure occurs with high frequency in APP/PS1 double transgenic mouse which is one of the Alzheimer's disease models due to Aβ overexpression (J. Neurosci., vol. 29, pages 3453-3462, 2012). Furthermore, since hippocampus astrocytes induce the expression of Cyp46 (CH24H) in a kainic acid lesion rat model, which is one of the epilepsy models, the relationship between this enzyme and pathology of epilepsy has been indicated (J. Neurol., vol. 65, pages 652-663, 2006). It has been reported that a therapeutic drug for seizure, carbamazepine, shows an improving effect on short-term memory in Y-maze test in an epileptic spasm mouse model (J. Neurol. Neurosurg. Psychiatry, vol. 48, pages 459-468, 1985). Therefore, a CH24H inhibitor, which shows an improving effect on short-term memory in a model animal showing an epileptic symptom, is promising as a novel therapeutic drug or prophylaxis drug for spasm, epilepsy, and the like.

Since schizophrenia shows a variety of psychological symptoms such as hallucination, delusion, excitation, manic-depressive state and the like, therapeutic drugs therefor have been developed with various approaches. In recent years, it has been pointed out that changes in the cholesterol metabolism are involved in the abnormality of neural activity seen in schizophrenia (J. Psychiatry Neurosci., vol. 36, pages 47-55, 2011). Since cytotoxic factors such as oxidative stress also contribute to the pathology of schizophrenia, neuronal cell toxicity of 24-HC may aggravate the symptoms (Psychoneuroendocrinology, vol. 28, pages 83-96, 2003). Therefore, a Cyp46 (CH24H) inhibitor that inhibits metabolizing cholesterol to 24-HC in the brain is promising as a therapeutic or prophylactic drug for schizophrenia.

Striatum (caudate, putamen) is reportedly a brain region high in the level of CH24H protein expression in primates in comparison with the globus pallidus, brainstem and cerebellum (Neurosci Bull., vol. 26, pages 197-204, 2010).

Neurodegenerative diseases such as Parkinson's disease, Huntington's disease, amyotrophic lateral sclerosis and Alzheimer's disease are related to dysfunction in striatum (Neuroimaging Clin. N. Am., vol. 22, pages 57-65, 2012; Can. J. Neurol. Sci. vol 13, pages 546-558, 1986; Acta. Neurol. Scand. Suppl., vol. 51, pages 139-150, 1972; Ann. Neurol., vol. 74, pages 20-38, 2013). Psychiatric disorders such as depression, schizophrenia and anxiety disorders, and other neurological disorders as epilepsy, ischemia and stroke are also related to these area (Dis. Nerv. Syst., vol. 33, pages 711-719, 1972; Dev. Cogn. Neurosci., vol. 8, pages 65-76, 2014; PLoS. One., vol. 8 pages e69905, 2013)

Under pathological condition, glial induction of CH24H was detected by means of immunohistochemistry with CH24H-specific antibody in Alzheimer's disease and traumatic brain injury (J. Biol. Chem., vol. 279, pages 34674-34681, 2004; Neurosci. Lett., vol. 314, pages 45-48, 2001); Histochem. Cell Biol., vol. 134, pages 159-169, 2010). These studies indicate the importance of on-site detection of CH24H by a methodology like histology or tomography. Experimental kainite-induced excitotoxicity also induced its expression in astrocytes in parallel with the increased 24-HC levels (J. Neuropathol. Exp. Neurol., vol. 65, pages 652-663, 2006). In contrast to the neuronal expression, the glial expression of CH24H is thought to be pathological response (Brain Res., vol. 818, pages 171-175, 1999). Therefore, CH24H could possibly play a role in brain diseases which are accompanied by glial activation such as epilepsy, glaucoma, multiple sclerosis, neuropathic pain, traumatic brain injury, spinal cord injury, migraine, stroke, Parkinson's disease, Huntington disease amyotrophic lateral sclerosis and detection of altered CH24H expression could lead to a diagnostic application for these diseases by such means as histological, radiological or biochemical analyses.

PET (Positron Emission Tomography) radiotracers and imaging technology may provide a powerful method for clinical evaluation and dose selection of CH24H inhibitors, and for diagnostic imaging with respect to any of the disorders associated with CH24H, such as epilepsy, neurodegenerative disease (e.g., Alzheimer's disease, mild cognitive disorder, Huntington's disease, Parkinson's disease, multiple sclerosis, amyotrophic lateral sclerosis, traumatic brain injury, cerebral infarction, glaucoma and the like), schizophrenia and the like. Thus, the invention herein is directed to radiolabeled CH24H inhibitors that would be useful for exploratory and diagnostic imaging applications, both in vitro and in vivo, and for competition studies using radiolabeled and unlabeled CH24H inhibitors.

As a CH24H inhibitor, the following compounds have been known.

Patent Document 1 discloses the following compound:

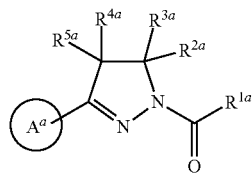

(Ia)

wherein each symbol is as defined in the document.

Patent Document 2 discloses the following compound:

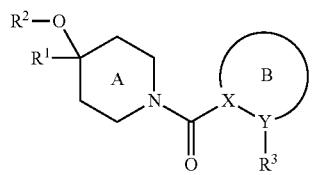

(I)

wherein each symbol is as defined in the document.

Patent Document 3 discloses the following compound:

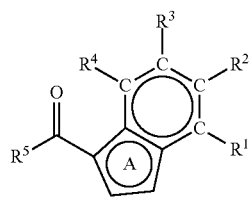

(I)

wherein each symbol is as defined in the document.

Patent Document 4 discloses the following compound:

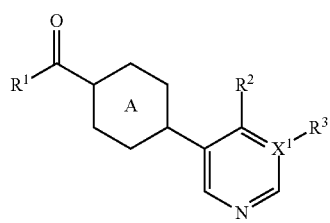

(I)

wherein each symbol is as defined in the document.

Patent Document 5 discloses the following compound:

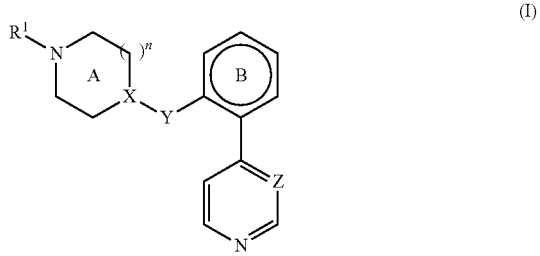

(I)

wherein each symbol is as defined in the document.

Patent Document 6 discloses the following compound:

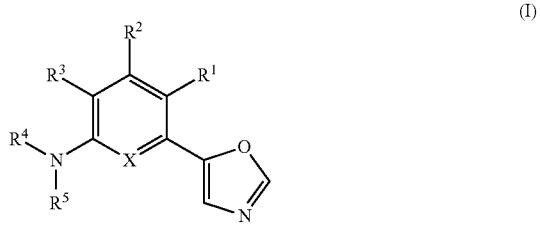

(I)

wherein each symbol is as defined in the document.

None of these documents do not disclose nor teach that the radiolabeled compound of the present invention is useful as a PET radiotracer.

DOCUMENT LIST

Patent Document

Patent Document 1: WO 2010/110400 A1
Patent Document 2: WO 2013/054822 A1
Patent Document 3: WO 2014/061676 A1
Patent Document 4: WO 2014/092100 A1
Patent Document 5: WO 2014/163161 A1
Patent Document 6: WO 2014/163162 A1

SUMMARY OF THE INVENTION

Problems to be Solved by the Invention

The present invention aims to provide novel radiolabeled compounds useful as radiotracers for quantitative imaging of CH24H in mammals.

Means of Solving the Problems

The present inventors have conducted intensive studies in an attempt to solve the aforementioned problems and found that the compounds represented by the below-mentioned formula (I) are useful as radiotracers for quantitative imaging of CH24H in mammals. Further studies made by the present inventors based on these findings have resulted in the completion of the present invention.

Accordingly, the present invention relates to

[1] A compound represented by the formula (I):

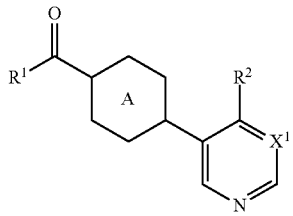

(I)

wherein
R¹ is
(1) a 3- to 8-membered monocyclic non-aromatic heterocyclic group substituted by 1 to 3 radiolabeled halogen atoms, or
(2) an amino group mono- or di-substituted by substituent(s) selected from
    (a) a $C_{1-6}$ alkyl group substituted by 1 to 3 radiolabeled halogen atoms, and
    (b) a radiolabeled $C_{1-6}$ alkyl group,
and optionally further substituted by a substituent selected from
    (c) a $C_{1-6}$ alkyl group substituted by 1 to 3 halogen atoms,
    (d) a $C_{1-6}$ alkyl group optionally substituted by $C_{6-14}$ aryl group(s) optionally substituted by 1 to 3 halogen atoms,
    (e) a $C_{3-8}$ cycloalkyl group, and
    (f) a 3- to 8-membered monocyclic non-aromatic heterocyclic group;
R² is
(1) a $C_{6-14}$ aryl group optionally substituted by 1 to 3 halogen atoms, or
(2) a 5- or 6-membered monocyclic aromatic heterocyclic group optionally substituted by 1 to 3 substituents selected from
    (a) a halogen atom,
    (b) a $C_{1-6}$ alkyl group, and
    (c) a $C_{3-8}$ cycloalkyl group;
    X¹ is CH or N; and
    Ring A is

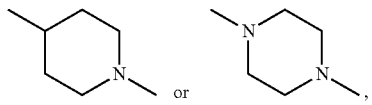

or a salt thereof (in the present specification, to be referred as compound (I)).

[2] The compound or salt of the above-mentioned [1], wherein R¹ is
(1) a 3- to 8-membered monocyclic non-aromatic heterocyclic group substituted by one radiolabeled halogen atom, or
(2) an amino group substituted by one substituent selected from
    (a) a $C_{1-6}$ alkyl group substituted by one radiolabeled halogen atom, and
    (b) a radiolabeled $C_{1-6}$ alkyl group,
and further substituted by one substituent selected from
    (c) a $C_{1-6}$ alkyl group optionally substituted by $C_{6-14}$ aryl group(s) optionally substituted by 1 to 3 halogen atoms,
    (d) a $C_{3-8}$ cycloalkyl group, and
    (e) a 3- to 8-membered monocyclic non-aromatic heterocyclic group.

[3] The compound or salt of the above-mentioned [1] or [2], wherein R¹ is a 3- to 8-membered monocyclic non-aromatic heterocyclic group substituted by one radiolabeled halogen atom.

[4] The compound or salt of any of the above-mentioned [1] to [3], wherein
R¹ is
(1) an azetizinyl group or a pyrrolidinyl group, each substituted by 1 to 3 radiolabeled halogen atoms, or
(2) an amino group mono- or di-substituted by substituent(s) selected from
    (a) a $C_{1-6}$ alkyl group substituted by 1 to 3 radiolabeled halogen atoms, and
    (b) a radiolabeled $C_{1-6}$ alkyl group,
and optionally further substituted by a substituent selected from
    (c) a $C_{1-6}$ alkyl group substituted by 1 to 3 halogen atoms,
    (d) a $C_{1-6}$ alkyl group optionally substituted by phenyl group(s) optionally substituted by 1 to 3 halogen atoms,
    (e) a $C_{3-8}$ cycloalkyl group,
    (f) a tetrahydropyranyl group, and
    (g) a tetrahydrofuryl group;
R² is
(1) a phenyl group optionally substituted by 1 to 3 halogen atoms, or
(2) a pyrazolyl group or a thiazolyl group, each optionally substituted by 1 to 3 substituents selected from
    (a) a halogen atom,
    (b) a $C_{1-6}$ alkyl group, and
    (c) a $C_{3-8}$ cycloalkyl group;
    X¹ is CH or N; and
    Ring A is

[5] The compound or salt of any of the above-mentioned [1] to [4], wherein
R¹ is
(1) an azetizinyl group or a pyrrolidinyl group, each substituted by one radiolabeled halogen atom, or
(2) an amino group substituted by one substituent selected from
    (a) a $C_{1-6}$ alkyl group substituted by one radiolabeled halogen atom, and
    (b) a radiolabeled $C_{1-6}$ alkyl group,
and further substituted by one substituent selected from (c) a $C_{1-6}$ alkyl group optionally substituted by phenyl group(s) optionally substituted by 1 to 3 halogen atoms,
(d) a $C_{3-8}$ cycloalkyl group,
(e) a tetrahydropyranyl group, and
(f) a tetrahydrofuryl group;
$R^2$ is
(1) a phenyl group optionally substituted by 1 to 3 halogen atoms, or
(2) a pyrazolyl group or a thiazolyl group, each optionally substituted by 1 to 3 substituents selected from
  (a) a halogen atom,
  (b) a $C_{1-6}$ alkyl group, and
  (c) a $C_{3-8}$ cycloalkyl group;
    $X^1$ is CH or N; and
    Ring A is

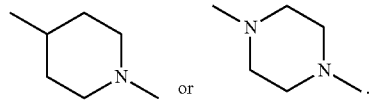 or 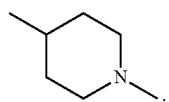

[6] The compound or salt of any of the above-mentioned [1] to [5], wherein
$R^1$ is an azetizinyl group or a pyrrolidinyl group, each substituted by one radiolabeled halogen atom;
$R^2$ is
(1) a phenyl group optionally substituted by 1 to 3 halogen atoms, or
(2) a pyrazolyl group or a thiazolyl group, each optionally substituted by 1 to 3 substituents selected from
  (a) a halogen atom,
  (b) a $C_{1-6}$ alkyl group, and
  (c) a $C_{3-8}$ cycloalkyl group;
    $X^1$ is CH or N; and
    Ring A is

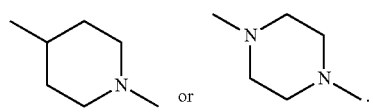 or 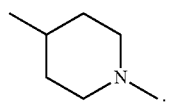

[7] The compound or salt of the above-mentioned [5], wherein $R^1$ is
(1) an azetizinyl group or a pyrrolidinyl group, each substituted by one $^{18}F$, or
(2) an amino group substituted by one substituent selected from
  (a) a $C_{1-6}$ alkyl group substituted by one $^{18}F$, and
  (b) a $C_1=6$ alkyl group radiolabeled by one $^{11}C$,
and further substituted by one substituent selected from
  (c) a $C_{1-6}$ alkyl group optionally substituted by phenyl group(s) optionally substituted by 1 to 3 halogen atoms,
  (d) a $C_{3-8}$ cycloalkyl group,
  (e) a tetrahydropyranyl group, and
  (f) a tetrahydrofuryl group.
[8] The compound or salt of the above-mentioned [6], wherein $R^1$ is an azetizinyl group or a pyrrolidinyl group, each substituted by one $^{18}F$.

[9] The compound or salt of any of the above-mentioned [1] to [8], wherein
$R^1$ is an azetizinyl group or a pyrrolidinyl group, each substituted by one $^{18}F$;
$R^2$ is
(1) a phenyl group optionally substituted by 1 to 3 halogen atoms, or
(2) a pyrazolyl group or a thiazolyl group, each optionally substituted by 1 to 3 substituents selected from
  (a) a halogen atom,
  (b) a $C_{1-6}$ alkyl group, and
  (c) a $C_{3-8}$ cycloalkyl group;
    $X^1$ is CH or N; and
    Ring A is

[9'] The compound or salt of any of the above-mentioned [1] to [9], wherein Ring A is

[10'] (3-[$^{18}F$]fluoroazetidin-1-yl) (1-(4-(4-fluorophenyl)pyrimidin-5-yl)piperidin-4-yl)methanone or a salt thereof, (1-(4-(4-chloro-1H-pyrazol-1-yl)pyridin-3-yl)piperidin-4-yl) (3-[$^{18}F$]fluoroazetidin-1-yl)methanone or a salt thereof, or (1-(4-(4-bromo-1H-pyrazol-1-yl)pyridin-3-yl)piperidin-4-yl) (3-[$^{18}F$]fluoroazetidin-1-yl)methanone or a salt thereof.
[10] (3-[$^{18}F$]Fluoroazetidin-1-yl) (1-(4-(4-fluorophenyl)pyrimidin-5-yl)piperidin-4-yl)methanone or a salt thereof.
[11] (1-(4-(4-Chloro-1H-pyrazol-1-yl)pyridin-3-yl)piperidin-4-yl) (3-[$^{18}F$]fluoroazetidin-1-yl)methanone or a salt thereof.
[12] (1-(4-(4-Bromo-1H-pyrazol-1-yl)pyridin-3-yl)piperidin-4-yl) (3-[$^{18}F$]fluoroazetidin-1-yl)methanone or a salt thereof.
[13] A method for quantitative imaging of cholesterol 24-hydroxylase in a mammal, which comprises administering to the mammal in need of such imaging an effective amount of the compound or salt of any of the above-mentioned [1] to [12], and obtaining an image useful for quantifying cholesterol 24-hydroxylase in the mammal using positron emission tomography.
[14] A method for quantitative imaging of cholesterol 24-hydroxylase in the brain in a mammal, which comprises administering to the mammal in need of such imaging an effective amount of the compound or salt of any of the above-mentioned [1] to [12], and obtaining an image useful for quantifying cholesterol 24-hydroxylase in the brain in the mammal using positron emission tomography.
[15] A method for diagnostic imaging of epilepsy or neurodegenerative disease associated with cholesterol 24-hydroxylase dysfunction in the brain in a mammal, which comprises administering to the mammal in need of such diagnostic imaging an effective amount of the compound or salt of any of the above-mentioned [1] to [12], and obtaining an image useful for quantifying cholesterol 24-hydroxylase in the brain in the mammal using positron emission tomography.

[16] The method of the above-mentioned [15], wherein the neurodegenerative disease is Alzheimer's disease, mild cognitive disorder, Huntington's disease, Parkinson's disease or multiple sclerosis.

[17] A method for the quantification of cholesterol 24-hydroxylase occupancy by a test compound or a salt thereof in mammalian tissue, which comprises contacting such mammalian tissue with an effective amount of the compound or salt of any of the above-mentioned [1] to [12], contacting such mammalian tissue with the test compound or a salt thereof and quantifying the cholesterol 24-hydroxylase using positron emission tomography.

[18] A composition comprising the compound or salt of any of the above-mentioned [1] to [12].

[19] Use of the compound or salt of any of the above-mentioned [1] to [12], for imaging a tissue, cells or a host, in vitro or in vivo.

[20] A method of imaging a tissue, cells or a host, which comprises contacting the compound or salt of any of the above-mentioned [1] to [12], with or administering to a tissue, cells or a host, and imaging the tissue, cells or host with a PET imaging system.

[21] The compound or salt of any of the above-mentioned [1] to [12], which is for use of quantitative imaging of cholesterol 24-hydroxylase.

Effect of the Invention

According to the present invention, novel radiolabeled compounds useful as radiotracers for quantitative imaging of CH24H in mammals can be provided.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

Figure 1:
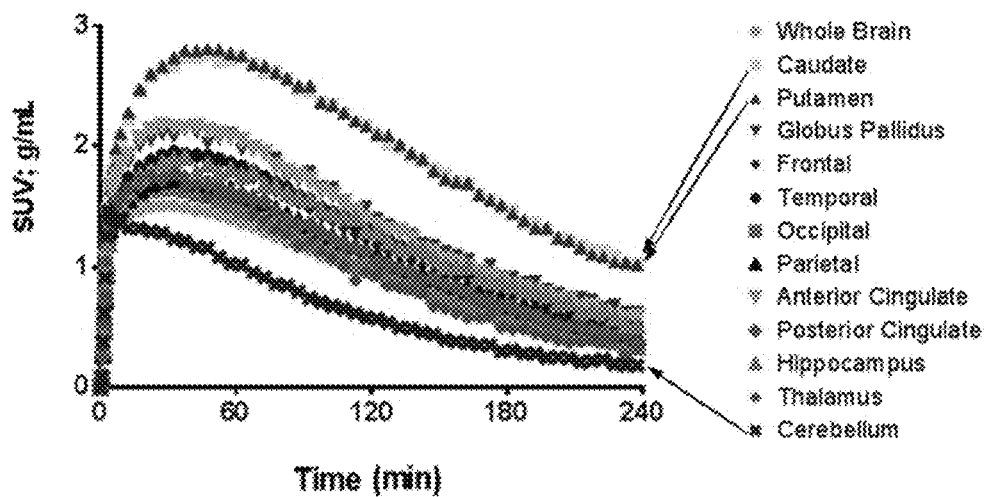
FIG. 1 shows time activity curves (TAC) of regional brain uptake of Example 1.

The present invention will be explained in detail below.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group, optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following substituent group A. [substituent group A]

(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),

(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the aforementioned substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkyl-phosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted amino group include an amino group, a mono- or di-(optionally halogenated $C_{1-6}$ alkyl)amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl)amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl)amino group (e.g., N-acetyl-N-methylamino) and a ($C_{1-6}$ alkyl) ($C_{6-14}$ aryl-carbonyl)amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from substituent group A".

Preferable examples of the optionally substituted silyl group include a tri-$C_{1-6}$ alkylsilyl group (e.g., trimethylsilyl, tert-butyl(dimethyl)silyl).

Each symbol of the formula (I) is explained below.
$R^1$ is
(1) a 3- to 8-membered monocyclic non-aromatic heterocyclic group (e.g., azetidinyl, pyrrolidinyl) substituted by 1 to 3 radiolabeled halogen atoms (e.g., $^{18}F$), or
(2) an amino group mono- or di-substituted by substituent(s) selected from
   (a) a $C_{1-6}$ alkyl group (e.g., ethyl) substituted by 1 to 3 radiolabeled halogen atoms (e.g., $^{18}F$), and
   (b) a radiolabeled $C_{1-6}$ alkyl group (e.g., $^{11}CH_3$—),
and optionally further substituted by a substituent selected from
   (c) a $C_{1-6}$ alkyl group substituted by 1 to 3 halogen atoms,
   (d) a $C_{1-6}$ alkyl group (e.g., methyl) optionally substituted by $C_{6-14}$ aryl group(s) (e.g., phenyl) optionally substituted by 1 to 3 halogen atoms (e.g., a fluorine atom),
   (e) a $C_{3-8}$ cycloalkyl group (e.g., cyclopropyl), and
   (f) a 3- to 8-membered monocyclic non-aromatic heterocyclic group (e.g., tetrahydropyranyl, tetrahydrofuryl).

In the present specification, examples of the "radiolabeled halogen atom" include $^{18}F$, $^{125}I$, $^{82}Br$, $^{123}I$, $^{131}I$, $^{75}Br$, $^{77}Br$ and the like.

In the present specification, examples of the "radiolabeled $C_{1-6}$ alkyl group" include a $C_{1-6}$ alkyl group having 1 or more $^{11}C$ and/or $^{14}C$.

The "$C_{1-6}$ alkyl group" in the "$C_{1-6}$ alkyl group substituted by 1 to 3 radiolabeled halogen atoms", the "$C_{1-6}$ alkyl group substituted by a radiolabeled halogen atom", the "$C_{1-6}$ alkyl group substituted by one $^{18}$F", the "radiolabeled $C_{1-6}$ alkyl group" and the "$C_{1-6}$ alkyl group radiolabeled by one $^{11}$C" may optionally be labeled with $^2$H (also written as D).

Examples of the "$C_{1-6}$ alkyl group substituted by 1 to 3 radiolabeled halogen atoms", the "$C_{1-6}$ alkyl group substituted by a radiolabeled halogen atom" and the "$C_{1-6}$ alkyl group substituted by one $^{18}$F" include $^{18}$FCH$_2$—, $^{18}$FCD$_2$-, $^{18}$FCH$_2$CH$_2$—, $^{18}$FCD$_2$CD$_2$- and the like.

Examples of the "radiolabeled $C_{1-6}$ alkyl group" and the "$C_{1-6}$ alkyl group radiolabeled by one $^{11}$C" include $^{11}$CH$_3$—, $^{11}$CD$_3$-, $^{11}$CD$_3$CH$_2$— and the like.

The "3- to 8-membered monocyclic non-aromatic heterocyclic group" of the "3- to 8-membered monocyclic non-aromatic heterocyclic group substituted by 1 to 3 radiolabeled halogen atoms" is preferably a 3- to 8-membered (preferably 4- or 5-membered) monocyclic non-aromatic nitrogen-containing heterocyclic group, more preferably a 3- to 8-membered (preferably 4- or 5-membered) saturated cyclylamino group.

$R^1$ is preferably
(1) a 3- to 8-membered (preferably 4- or 5-membered) monocyclic non-aromatic heterocyclic group (preferably a 3- to 8-membered (preferably 4- or 5-membered) monocyclic non-aromatic nitrogen-containing heterocyclic group (e.g., azetidinyl, pyrrolidinyl), more preferably a 3- to 8-membered (preferably 4- or 5-membered) saturated cyclylamino group (e.g., azetidin-1-yl, pyrrolidin-1-yl)) substituted by 1 to 3 radiolabeled halogen atoms (e.g., $^{18}$F), or
(2) an amino group mono- or di-substituted by substituent(s) selected from
  (a) a $C_{1-6}$ alkyl group (e.g., ethyl) substituted by 1 to 3 radiolabeled halogen atoms (e.g., $^{18}$F), and
  (b) a radiolabeled $C_{1-6}$ alkyl group (e.g., $^{11}$CH$_3$—),
and optionally further substituted by a substituent selected from
  (c) a $C_{1-6}$ alkyl group (e.g., methyl) optionally substituted by $C_{6-14}$ aryl group(s) (e.g., phenyl) optionally substituted by 1 to 3 halogen atoms (e.g., a fluorine atom),
  (d) a $C_{3-8}$ cycloalkyl group (e.g., cyclopropyl), and
  (e) a 3- to 8-membered monocyclic non-aromatic heterocyclic group (e.g., tetrahydropyranyl, tetrahydrofuryl).

$R^1$ is more preferably
(1) a 3- to 8-membered (preferably 4- or 5-membered) monocyclic non-aromatic heterocyclic group (preferably a 3- to 8-membered (preferably 4- or 5-membered) monocyclic non-aromatic nitrogen-containing heterocyclic group (e.g., azetidinyl, pyrrolidinyl), more preferably a 3- to 8-membered (preferably 4- or 5-membered) saturated cyclylamino group (e.g., azetidin-1-yl, pyrrolidin-1-yl)) substituted by one radiolabeled halogen atom (e.g., $^{18}$F), or
(2) an amino group substituted by one substituent selected from
  (a) a $C_{1-6}$ alkyl group (e.g., ethyl) substituted by one radiolabeled halogen atom (e.g., $^{18}$F), and
  (b) a radiolabeled $C_{1-6}$ alkyl group (e.g., $^{11}$CH$_3$—),
and further substituted by one substituent selected from
  (c) a $C_{1-6}$ alkyl group (e.g., methyl) optionally substituted by $C_{6-14}$ aryl group(s) (e.g., phenyl) optionally substituted by 1 to 3 halogen atoms (e.g., a fluorine atom),
  (d) a $C_{3-8}$ cycloalkyl group (e.g., cyclopropyl), and
  (e) a 3- to 8-membered monocyclic non-aromatic heterocyclic group (e.g., tetrahydropyranyl, tetrahydrofuryl).

In another embodiment, $R^1$ is preferably
(1) an azetizinyl group (preferably azetidin-1-yl) or a pyrrolidinyl group (preferably pyrrolidin-1-yl), each substituted by 1 to 3 radiolabeled halogen atoms (e.g., $^{18}$F), or
(2) an amino group mono- or di-substituted by substituent(s) selected from
  (a) a $C_{1-6}$ alkyl group (e.g., ethyl) substituted by 1 to 3 radiolabeled halogen atoms (e.g., $^{18}$F), and
  (b) a radiolabeled $C_{1-6}$ alkyl group (e.g., $^{11}$CH$_3$—),
and optionally further substituted by a substituent selected from
  (c) a $C_{1-6}$ alkyl group substituted by 1 to 3 halogen atoms,
  (d) a $C_{1-6}$ alkyl group (e.g., methyl) optionally substituted by phenyl group(s) optionally substituted by 1 to 3 halogen atoms (e.g., a fluorine atom),
  (e) a $C_{3-8}$ cycloalkyl group (e.g., cyclopropyl),
  (f) a tetrahydropyranyl group, and
  (g) a tetrahydrofuryl group.

$R^1$ is more preferably a 3- to 8-membered (preferably 4- or 5-membered) monocyclic non-aromatic heterocyclic group (preferably a 3- to 8-membered (preferably 4- or 5-membered) monocyclic non-aromatic nitrogen-containing heterocyclic group (e.g., azetidinyl, pyrrolidinyl), more preferably a 3- to 8-membered (preferably 4- or 5-membered) saturated cyclylamino group (e.g., azetidin-1-yl, pyrrolidin-1-yl)) substituted by one radiolabeled halogen atom (e.g., $^{18}$F).

In another embodiment, $R^1$ is more preferably
(1) an azetizinyl group (preferably azetidin-1-yl) or a pyrrolidinyl group (preferably pyrrolidin-1-yl), each substituted by one radiolabeled halogen atom (e.g., $^{18}$F), or
(2) an amino group substituted by one substituent selected from
  (a) a $C_{1-6}$ alkyl group (e.g., ethyl) substituted by one radiolabeled halogen atom (e.g., $^{18}$F), and
  (b) a radiolabeled $C_{1-6}$ alkyl group (e.g., $^{11}$CH$_3$—),
and further substituted by one substituent selected from
  (c) a $C_{1-6}$ alkyl group (e.g., methyl) optionally substituted by phenyl group(s) optionally substituted by 1 to 3 halogen atoms (e.g., a fluorine atom),
  (d) a $C_{3-8}$ cycloalkyl group (e.g., cyclopropyl),
  (e) a tetrahydropyranyl group, and
  (f) a tetrahydrofuryl group.

$R^1$ is further more preferably an azetizinyl group (preferably azetidin-1-yl) or a pyrrolidinyl group (preferably pyrrolidin-1-yl), each substituted by one radiolabeled halogen atom (e.g., $^{18}$F).

In another embodiment, $R^1$ is further more preferably
(1) an azetizinyl group (preferably azetidin-1-yl) or a pyrrolidinyl group (preferably pyrrolidin-1-yl), each substituted by one $^{18}$F, or
(2) an amino group substituted by one substituent selected from
  (a) a $C_{1-6}$ alkyl group (e.g., ethyl) substituted by one $^{18}$F, and
  (b) a $C_{1-6}$ alkyl group radiolabeled by one $^{11}$C (e.g., $^{11}$CH$_3$—),
and further substituted by one substituent selected from
  (c) a $C_{1-6}$ alkyl group (e.g., methyl) optionally substituted by phenyl group(s) optionally substituted by 1 to 3 halogen atoms (e.g., a fluorine atom),
  (d) a $C_{3-8}$ cycloalkyl group (e.g., cyclopropyl),
  (e) a tetrahydropyranyl group, and
  (f) a tetrahydrofuryl group.

$R^1$ is still more preferably an azetizinyl group (preferably azetidin-1-yl) or a pyrrolidinyl group (preferably pyrrolidin-1-yl), each substituted by one $^{18}$F.

$R^1$ is particularly preferably an azetizinyl group (preferably azetidin-1-yl) substituted by one $^{18}F$.

$R^2$ is
(1) a $C_{6-14}$ aryl group (e.g. phenyl) optionally substituted by 1 to 3 halogen atoms (e.g., a fluorine atom), or
(2) a 5- or 6-membered monocyclic aromatic heterocyclic group (e.g. pyrazolyl, thiazolyl) optionally substituted by 1 to 3 substituents selected from
   (a) a halogen atom (e.g., a chlorine atom, a bromine atom),
   (b) a $C_{1-6}$ alkyl group (e.g., methyl), and
   (c) a $C_{3-8}$ cycloalkyl group (e.g., cyclopropyl).

The above-mentioned "5- or 6-membered monocyclic aromatic heterocyclic group" is preferably a 5- or 6-membered monocyclic nitrogen-containing aromatic heterocyclic group (e.g. pyrazolyl, thiazolyl).

$R^2$ is preferably
(1) a phenyl group optionally substituted by 1 to 3 halogen atoms (e.g., a fluorine atom), or
(2) a 5- or 6-membered monocyclic nitrogen-containing aromatic heterocyclic group (e.g. pyrazolyl, thiazolyl) optionally substituted by 1 to 3 substituents selected from
   (a) a halogen atom (e.g., a chlorine atom, a bromine atom),
   (b) a $C_{1-6}$ alkyl group (e.g., methyl), and
   (c) a $C_{3-8}$ cycloalkyl group (e.g., cyclopropyl).

$R^2$ is more preferably
(1) a phenyl group optionally substituted by 1 to 3 halogen atoms (e.g., a fluorine atom), or
(2) a pyrazolyl group or a thiazolyl group, each optionally substituted by 1 to 3 substituents selected from
   (a) a halogen atom (e.g., a chlorine atom, a bromine atom),
   (b) a $C_{1-6}$ alkyl group (e.g., methyl), and
   (c) a $C_{3-8}$ cycloalkyl group (e.g., cyclopropyl).

$R^2$ is further more preferably
(1) a phenyl group substituted by one halogen atom (e.g., a fluorine atom), or
(2) a pyrazolyl group substituted by one halogen atom (e.g., a chlorine atom, a bromine atom).

$X^1$ is CH or N.

Ring A is

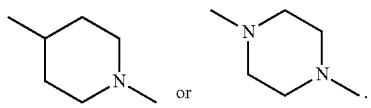

Ring A is preferably

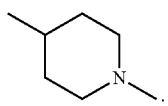

Preferable examples of compound (I) include the following compounds.

[Compound A]
Compound (I) wherein
$R^1$ is
(1) a 3- to 8-membered (preferably 4- or 5-membered) monocyclic non-aromatic heterocyclic group (preferably a 3- to 8-membered (preferably 4- or 5-membered) monocyclic non-aromatic nitrogen-containing heterocyclic group (e.g., azetidinyl, pyrrolidinyl), more preferably a 3- to 8-membered (preferably 4- or 5-membered) saturated cyclylamino group (e.g., azetidin-1-yl, pyrrolidin-1-yl)) substituted by 1 to 3 radiolabeled halogen atoms (e.g., $^{18}F$), or
(2) an amino group mono- or di-substituted by substituent(s) selected from
   (a) a $C_{1-6}$ alkyl group (e.g., ethyl) substituted by 1 to 3 radiolabeled halogen atoms (e.g., $^{18}F$), and
   (b) a radiolabeled $C_{1-6}$ alkyl group (e.g., $^{11}CH_3$—),
and optionally further substituted by a substituent selected from
   (c) a $C_{1-6}$ alkyl group (e.g., methyl) optionally substituted by $C_{6-14}$ aryl group(s) (e.g., phenyl) optionally substituted by 1 to 3 halogen atoms (e.g., a fluorine atom),
   (d) a $C_{3-8}$ cycloalkyl group (e.g., cyclopropyl), and
   (e) a 3- to 8-membered monocyclic non-aromatic heterocyclic group (e.g., tetrahydropyranyl, tetrahydrofuryl);

$R^2$ is
(1) a $C_{6-14}$ aryl group (e.g. phenyl) optionally substituted by 1 to 3 halogen atoms (e.g., a fluorine atom), or
(2) a 5- or 6-membered monocyclic aromatic heterocyclic group (e.g. pyrazolyl, thiazolyl) optionally substituted by 1 to 3 substituents selected from
   (a) a halogen atom (e.g., a chlorine atom, a bromine atom),
   (b) a $C_{1-6}$ alkyl group (e.g., methyl), and
   (c) a $C_{3-8}$ cycloalkyl group (e.g., cyclopropyl);

$X^1$ is CH or N; and

Ring A is

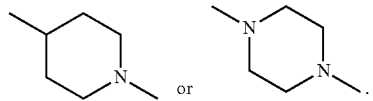

[Compound B]
Compound (I) wherein
$R^1$ is
(1) a 3- to 8-membered (preferably 4- or 5-membered) monocyclic non-aromatic heterocyclic group (preferably a 3- to 8-membered (preferably 4- or 5-membered) monocyclic non-aromatic nitrogen-containing heterocyclic group (e.g., azetidinyl, pyrrolidinyl), more preferably a 3- to 8-membered (preferably 4- or 5-membered) saturated cyclylamino group (e.g., azetidin-1-yl, pyrrolidin-1-yl)) substituted by one radiolabeled halogen atom (e.g., $^{18}F$), or
(2) an amino group substituted by one substituent selected from
   (a) a $C_{1-6}$ alkyl group (e.g., ethyl) substituted by one radiolabeled halogen atom (e.g., $^{18}F$), and
   (b) a radiolabeled $C_{1-6}$ alkyl group (e.g., $^{11}CH_3$—),
and further substituted by one substituent selected from
   (c) a $C_{1-6}$ alkyl group (e.g., methyl) optionally substituted by $C_{6-14}$ aryl group(s) (e.g., phenyl) optionally substituted by 1 to 3 halogen atoms (e.g., a fluorine atom),
   (d) a $C_{3-8}$ cycloalkyl group (e.g., cyclopropyl), and
   (e) a 3- to 8-membered monocyclic non-aromatic heterocyclic group (e.g., tetrahydropyranyl, tetrahydrofuryl);

$R^2$ is
(1) a $C_{6-14}$ aryl group (e.g. phenyl) optionally substituted by 1 to 3 halogen atoms (e.g., a fluorine atom), or
(2) a 5- or 6-membered monocyclic aromatic heterocyclic group (e.g. pyrazolyl, thiazolyl) optionally substituted by 1 to 3 substituents selected from (a) a halogen atom (e.g., a chlorine atom, a bromine atom),
(b) a $C_{1-6}$ alkyl group (e.g., methyl), and
(c) a $C_{3-8}$ cycloalkyl group (e.g., cyclopropyl);
$X^1$ is CH or N; and
Ring A is

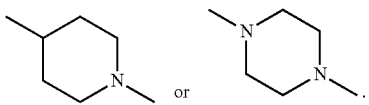

[Compound C]
Compound (I) wherein
$R^1$ is a 3- to 8-membered (preferably 4- or 5-membered) monocyclic non-aromatic heterocyclic group (preferably a 3- to 8-membered (preferably 4- or 5-membered) monocyclic non-aromatic nitrogen-containing heterocyclic group (e.g., azetidinyl, pyrrolidinyl), more preferably a 3- to 8-membered (preferably 4- or 5-membered) saturated cyclylamino group (e.g., azetidin-1-yl, pyrrolidin-1-yl)) substituted by one radiolabeled halogen atom (e.g., $^{18}F$);
$R^2$ is
(1) a $C_{6-14}$ aryl group (e.g. phenyl) optionally substituted by 1 to 3 halogen atoms (e.g., a fluorine atom), or
(2) a 5- or 6-membered monocyclic aromatic heterocyclic group (e.g. pyrazolyl, thiazolyl) optionally substituted by 1 to 3 substituents selected from
    (a) a halogen atom (e.g., a chlorine atom, a bromine atom),
    (b) a $C_{1-6}$ alkyl group (e.g., methyl), and
    (c) a $C_{3-8}$ cycloalkyl group (e.g., cyclopropyl);
$X^1$ is CH or N; and
Ring A is

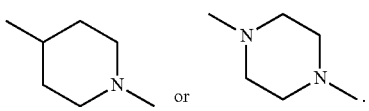

[Compound D]
Compound (I) wherein
$R^1$ is
(1) a 3- to 8-membered (preferably 4- or 5-membered) monocyclic non-aromatic heterocyclic group (preferably a 3- to 8-membered (preferably 4- or 5-membered) monocyclic non-aromatic nitrogen-containing heterocyclic group (e.g., azetidinyl, pyrrolidinyl), more preferably a 3- to 8-membered (preferably 4- or 5-membered) saturated cyclylamino group (e.g., azetidin-1-yl, pyrrolidin-1-yl)) substituted by one radiolabeled halogen atom (e.g., $^{18}F$), or
(2) an amino group substituted by one substituent selected from
    (a) a $C_{1-6}$ alkyl group (e.g., ethyl) substituted by one radiolabeled halogen atom (e.g., $^{18}F$), and
    (b) a radiolabeled $C_{1-6}$ alkyl group (e.g., $^{11}CH_3-$),
and further substituted by one substituent selected from
    (c) a $C_{1-6}$ alkyl group (e.g., methyl) optionally substituted by $C_{6-14}$ aryl group(s) (e.g., phenyl) optionally substituted by 1 to 3 halogen atoms (e.g., a fluorine atom),
    (d) a $C_{3-8}$ cycloalkyl group (e.g., cyclopropyl), and
    (e) a 3- to 8-membered monocyclic non-aromatic heterocyclic group (e.g., tetrahydropyranyl, tetrahydrofuryl);

$R^2$ is
(1) a $C_{6-14}$ aryl group (e.g. phenyl) optionally substituted by 1 to 3 halogen atoms (e.g., a fluorine atom), or
(2) a 5- or 6-membered monocyclic nitrogen-containing aromatic heterocyclic group (e.g. pyrazolyl, thiazolyl) optionally substituted by 1 to 3 substituents selected from
    (a) a halogen atom (e.g., a chlorine atom, a bromine atom),
    (b) a $C_{1-6}$ alkyl group (e.g., methyl), and
    (c) a $C_{3-8}$ cycloalkyl group (e.g., cyclopropyl);
$X^1$ is CH or N; and
Ring A is

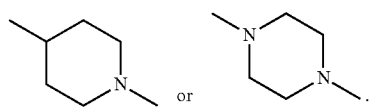

[Compound E]
Compound (I) wherein
$R^1$ is a 3- to 8-membered (preferably 4- or 5-membered) monocyclic non-aromatic heterocyclic group (preferably a 3- to 8-membered (preferably 4- or 5-membered) monocyclic non-aromatic nitrogen-containing heterocyclic group (e.g., azetidinyl, pyrrolidinyl), more preferably a 3- to 8-membered (preferably 4- or 5-membered) saturated cyclylamino group (e.g., azetidin-1-yl, pyrrolidin-1-yl)) substituted by one radiolabeled halogen atom (e.g., $^{18}F$);
$R^2$ is
(1) a $C_{6-14}$ aryl group (e.g. phenyl) optionally substituted by 1 to 3 halogen atoms (e.g., a fluorine atom), or
(2) a 5- or 6-membered monocyclic nitrogen-containing aromatic heterocyclic group (e.g. pyrazolyl, thiazolyl) optionally substituted by 1 to 3 substituents selected from
    (a) a halogen atom (e.g., a chlorine atom, a bromine atom),
    (b) a $C_{1-6}$ alkyl group (e.g., methyl), and
    (c) a $C_{3-8}$ cycloalkyl group (e.g., cyclopropyl);
$X^1$ is CH or N; and
Ring A is

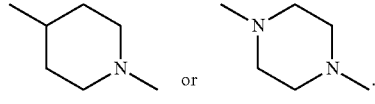

[Compound F]
Compound (I) wherein
$R^1$ is
(1) an azetizinyl group (preferably azetidin-1-yl) or a pyrrolidinyl group (preferably pyrrolidin-1-yl), each substituted by 1 to 3 radiolabeled halogen atoms (e.g., $^{18}F$), or
(2) an amino group mono- or di-substituted by substituent(s) selected from
    (a) a $C_{1-6}$ alkyl group (e.g., ethyl) substituted by 1 to 3 radiolabeled halogen atoms (e.g., $^{18}F$), and
    (b) a radiolabeled $C_{1-6}$ alkyl group (e.g., $^{11}CH_3-$),
and optionally further substituted by a substituent selected from
    (c) a $C_{1-6}$ alkyl group substituted by 1 to 3 halogen atoms,
    (d) a $C_{1-6}$ alkyl group (e.g., methyl) optionally substituted by phenyl group(s) optionally substituted by 1 to 3 halogen atoms (e.g., a fluorine atom),
    (e) a $C_{3-8}$ cycloalkyl group (e.g., cyclopropyl), (f) a tetrahydropyranyl group, and
(g) a tetrahydrofuryl group;
R² is
(1) a phenyl group optionally substituted by 1 to 3 halogen atoms (e.g., a fluorine atom), or
(2) a pyrazolyl group or a thiazolyl group, each optionally substituted by 1 to 3 substituents selected from
  (a) a halogen atom (e.g., a chlorine atom, a bromine atom),
  (b) a $C_{1-6}$ alkyl group (e.g., methyl), and
  (c) a $C_{3-8}$-cycloalkyl group (e.g., cyclopropyl);
X¹ is CH or N; and
Ring A is

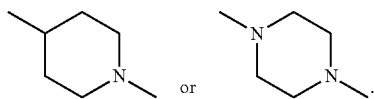

[Compound G]
Compound (I) wherein
R¹ is
(1) an azetizinyl group (preferably azetidin-1-yl) or a pyrrolidinyl group (preferably pyrrolidin-1-yl), each substituted by one radiolabeled halogen atom (e.g., ¹⁸F), or
(2) an amino group substituted by one substituent selected from
  (a) a $C_{1-6}$ alkyl group (e.g., ethyl) substituted by one radiolabeled halogen atom (e.g., ¹⁸F), and
  (b) a radiolabeled $C_{1-6}$ alkyl group (e.g., ¹¹CH₃—),
and further substituted by one substituent selected from
  (c) a $C_{1-6}$ alkyl group (e.g., methyl) optionally substituted by phenyl group(s) optionally substituted by 1 to 3 halogen atoms (e.g., a fluorine atom),
  (d) a $C_{3-8}$ cycloalkyl group (e.g., cyclopropyl),
  (e) a tetrahydropyranyl group, and
  (f) a tetrahydrofuryl group;
R² is
(1) a phenyl group optionally substituted by 1 to 3 halogen atoms (e.g., a fluorine atom), or
(2) a pyrazolyl group or a thiazolyl group, each optionally substituted by 1 to 3 substituents selected from
  (a) a halogen atom (e.g., a chlorine atom, a bromine atom),
  (b) a $C_{1-6}$ alkyl group (e.g., methyl), and
  (c) a $C_{3-8}$ cycloalkyl group (e.g., cyclopropyl);
X¹ is CH or N; and
Ring A is

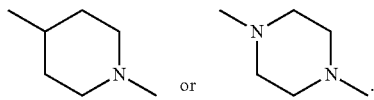

[Compound H]
Compound (I) wherein
R¹ is an azetizinyl group (preferably azetidin-1-yl) or a pyrrolidinyl group (preferably pyrrolidin-1-yl), each substituted by one radiolabeled halogen atom (e.g., ¹⁸F);
R² is
(1) a phenyl group optionally substituted by 1 to 3 halogen atoms (e.g., a fluorine atom), or
(2) a pyrazolyl group or a thiazolyl group, each optionally substituted by 1 to 3 substituents selected from
  (a) a halogen atom (e.g., a chlorine atom, a bromine atom),
  (b) a $C_{1-6}$ alkyl group (e.g., methyl), and
  (c) a $C_{3-8}$ cycloalkyl group (e.g., cyclopropyl);
X¹ is CH or N; and
Ring A is

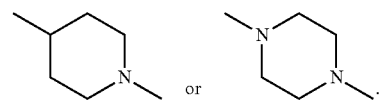

[Compound I]
Compound (I) wherein
R¹ is
(1) an azetizinyl group (preferably azetidin-1-yl) or a pyrrolidinyl group (preferably pyrrolidin-1-yl), each substituted by one ¹⁸F, or
(2) an amino group substituted by one substituent selected from
  (a) a $C_{1-6}$ alkyl group (e.g., ethyl) substituted by one ¹⁸F, and
  (b) a $C_{1-6}$ alkyl group radiolabeled by one ¹¹C (e.g., ¹¹CH₃—),
and further substituted by one substituent selected from
  (c) a $C_{1-6}$ alkyl group (e.g., methyl) optionally substituted by phenyl group(s) optionally substituted by 1 to 3 halogen atoms (e.g., a fluorine atom),
  (d) a $C_{3-8}$ cycloalkyl group (e.g., cyclopropyl),
  (e) a tetrahydropyranyl group, and
  (f) a tetrahydrofuryl group;
R² is
(1) a phenyl group optionally substituted by 1 to 3 halogen atoms (e.g., a fluorine atom), or
(2) a pyrazolyl group or a thiazolyl group, each optionally substituted by 1 to 3 substituents selected from
  (a) a halogen atom (e.g., a chlorine atom, a bromine atom),
  (b) a $C_{1-6}$ alkyl group (e.g., methyl), and
  (c) a $C_{3-8}$ cycloalkyl group (e.g., cyclopropyl);
X¹ is CH or N; and
Ring A is

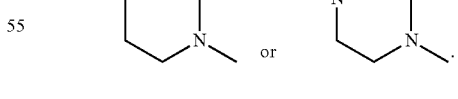

[Compound J]
Compound (I) wherein
R¹ is an azetizinyl group (preferably azetidin-1-yl) or a pyrrolidinyl group (preferably pyrrolidin-1-yl), each substituted by one ¹⁸F;
R² is
(1) a phenyl group optionally substituted by 1 to 3 halogen atoms (e.g., a fluorine atom), or (2) a pyrazolyl group or a thiazolyl group, each optionally substituted by 1 to 3 substituents selected from
  (a) a halogen atom (e.g., a chlorine atom, a bromine atom),
  (b) a $C_{1-6}$ alkyl group (e.g., methyl), and
  (c) a $C_{3-8}$ cycloalkyl group (e.g., cyclopropyl);
$X^1$ is CH or N; and
Ring A is

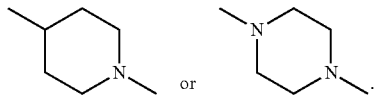

[Compound K]
Compound (I) wherein
$R^1$ is an azetizinyl group (preferably azetidin-1-yl) or a pyrrolidinyl group (preferably pyrrolidin-1-yl), each substituted by one $^{18}F$;
$R^2$ is
(1) a phenyl group optionally substituted by 1 to 3 halogen atoms (e.g., a fluorine atom), or
(2) a pyrazolyl group or a thiazolyl group, each optionally substituted by 1 to 3 substituents selected from
  (a) a halogen atom (e.g., a chlorine atom, a bromine atom),
  (b) a $C_{1-6}$ alkyl group (e.g., methyl), and
  (c) a $C_{3-8}$ cycloalkyl group (e.g., cyclopropyl);
$X^1$ is CH or N; and
Ring A is

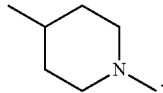

[Compound L]
Compound (I) wherein
$R^1$ is an azetizinyl group (preferably azetidin-1-yl) substituted by one $^{18}F$;
$R^2$ is
(1) a phenyl group substituted by one halogen atom (e.g., a fluorine atom), or
(2) a pyrazolyl group substituted by one halogen atom (e.g., a chlorine atom, a bromine atom).
$X^1$ is CH or N; and
Ring A is

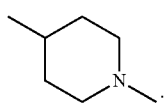

[Compound M-1]
(3-[$^{18}F$]fluoroazetidin-1-yl) (1-(4-(4-fluorophenyl)pyrimidin-5-yl)piperidin-4-yl)methanone
[Compound M-2]
(1-(4-(4-chloro-1H-pyrazol-1-yl)pyridin-3-yl)piperidin-4-yl) (3-[$^{18}F$]fluoroazetidin-1-yl)methanone
[Compound M-3]
(1-(4-(4-bromo-1H-pyrazol-1-yl)pyridin-3-yl)piperidin-4-yl) (3-[$^{18}F$]fluoroazetidin-1-yl)methanone
When the compound (I) is a salt, for example, metal salts, ammonium salts, salts with organic bases, salts with inorganic acids, salts with organic acids, salts with basic or acidic amino acids can be included. Preferable examples of metal salts, for example, include alkali metal salts such as sodium salts, potassium salts and the like; alkali earth metal salts such as calcium salts, magnesium salts, barium salts and the like; and aluminum salts. Preferable examples of salts with organic bases include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of salts with inorganic acids include salts with hydrochloric acid, hydrobromic acid, nitric acid, sulfuric acid, phosphoric acid and the like. Preferable examples of salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of salts with basic amino acids include salts with arginine, lysine, ornithine and the like. Preferable examples of salts with acidic amino acids include salts with aspartic acid, glutamic acid and the like. Among them, salts that are pharmacologically acceptable are preferable. For example, in the case when acidic functional group are present in the compound, for example, inorganic salts including alkali metal salts (e.g., sodium salts, etc.) and alkali earth metal salts (e.g., calcium salts, magnesium salts, barium salts, etc.) and ammonium salts are preferable. In contrast, in the case when basic functional group are present in the compound, for example, salts with inorganic acids such as hydrochloric acid, hydrobromic acid, nitric acid, sulfuric acid, phosphoric acid, etc. or salts with organic acid such as acetic acid, phthalic acid, fumaric acid, oxalic acid, tartaric acid, maleic acid, citric acid, succinic acid, methanesulfonic acid, p-toluenesulfonic acid, etc. are preferable.

If the compound (I) includes isomers such as tautomers, optical isomers, steric isomers, reverse isomers and rotational isomers, one of the other isomers or mixture are also included in the compound of the present invention. Further, if the compound (I) has an optical isomer, the optical isomer separated from the racemate is included in the compound (I).

The compound (I) can be obtained in the crystal form. Either single crystalline form or crystalline mixture can be included in the compound (I).

The compound of the formula (I) can be a pharmaceutically acceptable co-crystal or a co-crystal salt. The term "co-crystal" or "co-crystal salt" as used herein means a crystalline material composed of two or more unique solids at room temperature, each of which has distinctive physical characteristics such as structure, melting point, and heats of fusion, hygroscopicity, solubility, and stability. A co-crystal or a co-crystal salt can be obtained according to a per se known co-crystallization method.

The compound (I) can be provided as a solvate (for example, hydrate) or as a non-solvate and both are included in the compound (I).

The compounds labeled with isotopes (e.g., $^2H$ (also written as D), $^3H$ (also written as T), $^{11}C$, $^{14}C$, $^{18}F$, $^{35}S$, $^{125}I$, etc.) are also included in the compound (I).

[Manufacturing Methods]

The compound of the present invention and the starting compounds can be produced by a method known per se, for example, by method shown in the following scheme and the like. In the following, the "room temperature" generally means 0-40° C. and, unless otherwise specified, each symbol in the chemical formulas described in the schemes is as defined above. In the formulas, each compound includes salts, and examples of such salt include those similar to the salts of the compound of the present invention and the like. The compound obtained in each step can be used directly as the reaction mixture or as a crude product for the next reaction. It can also be isolated from a reaction mixture by a conventional method, and can be easily purified by a separation means such as recrystallization, distillation, chromatography and the like. When the compound in the formula is commercially available, a commercially available product can also be used directly. When each ring in the formula (I) has a substituent, the corresponding precursor also has a similar substituent.

When the starting compound has an amino group, a carboxyl group, a hydroxy group or a heterocyclic group, these groups may be protected by a protecting group generally used in peptide chemistry and the like. By removing the protecting group as necessary after the reaction, the objective compound can be obtained. The protection and deprotection can be performed according to a method known per se, for example, the method described in "Protective Groups in Organic Synthesis, 3rd Ed", John Wiley and Sons, Inc. (1999) (Theodora W. Greene, Peter G. M. Wuts). Preferable examples of the protecting group include a tert-butylcarbamate group, a benzylcarbamate group, a benzyl group, a methyl group, an ethyl group, a tert-butyl and the like.

Examples of the "leaving group" for $LG^1$ to $LG^5$ include a halogen atom (e.g., a fluorine atom, a chlorine atom, a bromine atom, an iodine atom etc.), $C_{1-6}$ alkylsulfonyloxy (e.g., methanesulfonyloxy, ethanesulfonyloxy, trifluoromethanesulfonyloxy etc.), $C_{1-6}$ alkylsulfonyl (e.g., methanesulfonyl, ethanesulfonyl etc.), $C_{6-14}$ arylsulfonyloxy (e.g., phenylsulfonyloxy, 4-methylbenzene-1-sulfonyloxy etc.), $C_{6-14}$ arylsulfonyl (e.g., phenylsulfonyl, 4-methylbenzene-1-sulfonyl etc.) and the like. In addition, a substituent capable of converting to a leaving group is encompassed in $LG^1$-$LG^5$, and it can be converted to a leaving group according to a reaction known per se in a desired step. For example, when $LG^1$-$LG^5$ is a methylsulfanyl group, it is converted to a methanesulfonyl group by oxidation reaction.

The following each step can be performed without solvent, or by dissolving or suspending starting material compound in a suitable solvent prior to the reaction. In this case, solvent may be used alone, or two or more kinds of these solvents may be mixed in an appropriate ratio and used. Specific examples of the solvent used for the production method of the compound of the present invention include the followings.
alcohols: methanol, ethanol, 1-propanol, 2-propanol, tert-butyl alcohol, tert-amyl alcohol, 2-methoxyethanol etc.
ethers: diethyl ether, diisopropyl ether, diphenyl ether, tetrahydrofuran, 1,4-dioxane, 1,2-dimethoxyethane etc. aromatic hydrocarbons: benzene, chlorobenzene, toluene, xylene etc.
saturated hydrocarbons: cyclohexane, hexane etc.
amides: N,N-dimethylformamide, N,N-dimethylacetamide, hexamethylphosphoric triamide, N-methylpyrrolidone etc.
halogenated hydrocarbons: dichloromethane, chloroform, carbon tetrachloride, 1,2-dichloroethane etc.
nitriles: acetonitrile, propionitrile etc.
sulfoxides: dimethylsulfoxide etc.
organic bases: triethylamine, pyridine, lutidine etc.
acid anhydrides: acetic anhydride etc.
organic acids: formic acid, acetic acid, propionic acid, trifluoroacetic acid, methanesulfonic acid etc.
inorganic acids: hydrochloric acid, sulfuric acid etc.
esters: methyl acetate, ethyl acetate, butyl acetate etc.
ketones: acetone, methyl ethyl ketone etc.
water Specific examples of the base or acid scavenger used for the production method of the compound of the present invention include the followings.
inorganic bases: sodium hydroxide, potassium hydroxide, magnesium hydroxide etc.
basic salts: sodium carbonate, potassium carbonate, cesium carbonate, calcium carbonate, sodium hydrogen carbonate etc. organic bases: triethylamine, diisopropylethylamine, tributylamine, cyclohexyldimethylamine, pyridine, lutidine, 4-dimethylaminopyridine, N,N-dimethylaniline, N-methylpiperidine, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene, imidazole etc.
metal alkoxides: sodium methoxide, sodium ethoxide, potassium tert-butoxide etc.
alkali metal hydrides: sodium hydride, potassium hydride etc.
metal amides: sodium amide, lithiumdiisopropylamide, lithiumhexamethyldisilazide etc.
organic lithium reagents: methyllithium, n-butyllithium, sec-butyllithium, tert-butyllithium etc.

Specific examples of the acid or acid catalyst used for the production method of the compound of the present invention include the followings.
inorganic acids: hydrochloric acid, sulfuric acid, nitric acid, hydrobromic acid, phosphoric acid etc.
organic acids: acetic acid, trifluoroacetic acid, oxalic acid, phthalic acid, fumaric acid, tartaric acid, maleic acid, citric acid, succinic acid, methanesulfonic acid, p-toluenesulfonic acid, 10-camphorsulfonic acid etc.
Lewis acid: boron trifluoride ether complex, zinc iodide, anhydrous aluminum chloride, anhydrous zinc chloride, anhydrous iron chloride etc.

Compound (I) can be produced according to Production Method A.

Unless otherwise specified, each symbol in the general formulas in the schemes is as defined above.

Each $R^a$ is a hydrogen atom or an optionally substituted $C_{1-6}$ alkyl group. When each $R^a$ is an optionally substituted $C_{1-6}$ alkyl group, two $R^a$ in combination optionally form a ring such as 4,4,5,5-tetramethyl-1,3,2-dioxaborolane and the like.

$R^3$ is an optionally substituted hydrocarbon group, an optionally substituted heterocyclic group or a hydrogen atom.

$X^2$ is an optionally substituted carbon atom or a nitrogen atom.

$X^3$ is an oxygen atom or a sulfur atom.

The "$C_{1-6}$ alkyl group" of the "optionally substituted $C_{1-6}$ alkyl group" for $R^a$ optionally has 1 to 5 (preferably 1 to 3) substituents at substitutable position(s). Examples of the substituent include substituents selected from the aforementioned substituent group A. When the number of the substituents is plural, the respective substituents may be the same or different.

The "carbon atom" of the "optionally substituted carbon atom" for $X^2$ optionally has 1 or 2 substituents. Examples of the substituent include substituents selected from the aforementioned substituent group A. When the number of the substituents is plural, the respective substituents may be the same or different.

[Production Method A]

(Scheme 1)

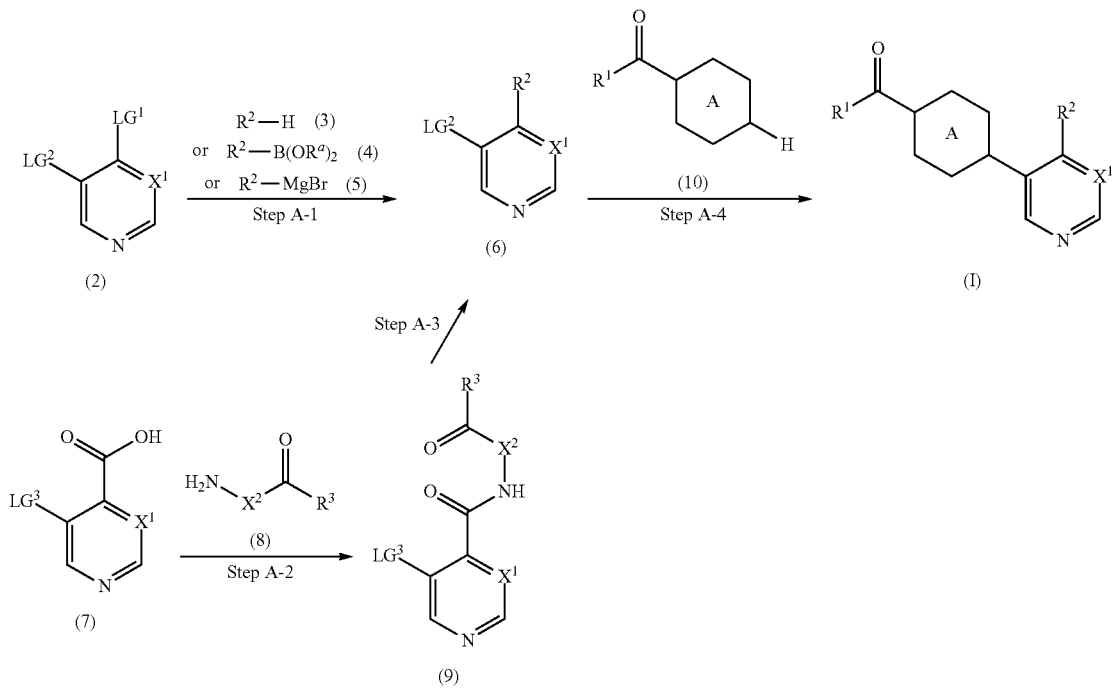

(Step A-1)

Compound (6) can be produced by reacting compound (2) with compound (3), or compound (2) with compound (4), or compound (2) with compound (5). The reaction is carried out using compound (2) and compound (3), or compound (2) and compound (4), or compound (2) and compound (5) in the presence of an acid catalyst, a base or a metal catalyst. Examples of the acid catalyst include organic acids and the like. The acid catalyst is used in an amount of about 0.05 to 2 mol, per 1 mol of compound (2). Examples of the base include basic salts, organic bases, alkali metal hydrides, organic lithium reagents and the like. The base is used in an amount of about 1 to 20 mol per 1 mol of compound (2). Examples of the metal catalyst include palladium compounds [e.g.: palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), [1,1-bis(diphenylphosphino)ferrocene]dichloropalladium(II), a complex of palladium(II) acetate and 1,1'-bis(diphenylphosphino)ferrocene, and the like], copper compounds [e.g.: copper(I) iodide, copper(I) bromide and the like] and the like. The metal catalyst is used in an amount of about 0.000001 to 10 mol, per 1 mol of compound (2). The metal catalyst can be used together with a phosphine ligand [e.g.: triphenylphosphine, 4,5-bis(diphenylphosphino)-9,9-dimethylxanthene, tri-tert-butylphosphine, tri-tert-butylphosphine tetrafluoroborate and the like] or an amine ligand [e.g.: 8-methylquinolin-1-ol, 1,10-phenanthroline, 1,2-diaminocyclohexane, N,N'-dimethyl-1,2-ethanediamine and the like]. The phosphine ligand or amine ligand is used in an amount of about 0.01 to 5 mol, per 1 mol of compound (2). Compound (3), compound (4) or compound (5) is used in an amount of about 0.8 to 10 mol, per 1 mol of compound (2).

When the reaction is carried out using a metal catalyst, the reaction is preferably carried out in the presence of a base. Examples of the base include inorganic bases, basic salts and the like. The base is used in an amount of about 1 to 20 mol per 1 mol of compound (2). When the reaction is carried out using a metal catalyst unstable to oxygen, for example, the reaction is preferably carried out under inert gas such as argon gas, nitrogen gas and the like. This reaction is advantageously carried out in a solvent inert to the reaction. The solvent is not particularly limited as long as the reaction proceeds. Preferable examples thereof include alcohols, ethers, aromatic hydrocarbons, saturated hydrocarbons, amides, halogenated hydrocarbons, nitriles, esters, sulfoxides, water, mixed solvents thereof and the like. While the reaction time varies depending on the kind of the reagent and solvent to be used, it is generally 1 min to 200 hr. The reaction temperature is preferably 0 to 200° C. In addition, microwave may be irradiated to promote the reaction. Compound (2), compound (3), compound (4) and compound (5) may be a commercially available product, or can also be produced according to a method known per se or a method analogous thereto.

Compound (6) wherein $R^2$ is

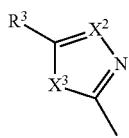

can also be produced from compound (7) according to a sequence reaction step of Step A-2 to Step A-3.

(Step A-2)

Compound (9) can be produced by subjecting compound (7) to condensation with compound (8). The condensation reaction is carried out by reacting compound (7) or a reactive derivative thereof with compound (8). Examples of the reactive derivative include acid halides such as acid chlorides, acid bromides and the like; acid amides with pyrazole, imidazole, benzotriazole and the like; mixed anhydride with acetic acid, propionic acid, butyric acid and the like; acid azides; activated esters such as diethoxyphosphoric acid ester, diphenoxyphosphoric acid ester, p-nitrophenyl ester, 2,4-dinitrophenyl ester, cyanomethyl ester, pentachlorophenyl ester, an ester with N-hydroxysuccinimide, an ester with N-hydroxyphthalimide, an ester with 1-hydroxybenzotriazole, an ester with 6-chloro-1-hydroxybenzotriazole, an ester with 1-hydroxy-1H-2-pyridone, and the like; activated thio esters such as 2-pyridylthio ester, 2-benzothiazolylthio ester and the like, and the like. Alternatively, instead of use of the reactive derivative, compound (7) may be directly reacted with compound (8) in the presence of a suitable condensing agent. Examples of the condensing agent include N,N'-disubstituted carbodiimides such as N,N'-dicyclohexyl carbodiimide, 1-ethyl-3-(3-dimethylaminopropyl)carbodiimide (WSC) hydrochloride and the like; azolides such as N,N'-carbonyldiimidazole and the like; dehydrating agents such as N-ethoxycarbonyl-2-ethoxy-1,2-dihydroquinoline, phosphorus oxychloride, alkoxy acethylene and the like; 2-halogeno pyridinium salts such as 2-chloromethylpyridinium iodide, 2-fluoro-1-methylpyridinium iodide and the like; phosphorylcyanides-such as diethylphosphorylcyanide and the like; 2-(7-azabenzotriazol-1-yl)-1,1,3,3-tetramethyluronium hexafluorophosphate (HATU), O-(7-azabenzotriazole-1-yl)-N,N,N',N'-tetramethyluronium tetrafluoroborate (TATU) and the like. The reaction is considered to proceed via a reactive derivative of compound (7) by using a condensing agent. Compound (8) is generally used in an amount of about 0.8 to 5 mol, per 1 mol of compound (7) or a reactive derivative thereof. This reaction is advantageously carried out in a solvent inert to the reaction. The solvent is not particularly limited as long as the reaction proceeds. Preferable examples thereof include ethers, aromatic hydrocarbons, saturated hydrocarbons, amides, halogenated hydrocarbons, nitriles, sulfoxides, aromatic organic bases, mixed solvent thereof and the like. In addition, when an acidic substance is generated due to the reaction, the reaction can be carried out in the presence of an acid scavenger to remove the acidic substance from the reaction system. Examples of the acid scavenger include basic salts, organic bases and the like. In addition, for example, basic salts, organic bases and the like can also be used to promote the reaction. While the reaction time varies depending on the kind of the reagent and solvent to be used, it is generally 1 min to 72 hr. The reaction temperature is preferably 0 to 100° C. Compound (7) and compound (8) may be a commercially available product, or can also be produced according to a method known per se or a method analogous thereto.

(Step A-3)

Compound (6) can be produced by treating compound (9) with an acid or a dehydrating agent. Examples of the acid include organic acids, inorganic acids and the like. The acid is used in an amount of about 1 to 50 mol per 1 mol of compound (9). Examples of the dehydrating agent include phosphorus oxychloride, methyl carbamate-N-(triethylammonium sulfonyl) (Burgess reagent) and the like. The dehydrating agent is used in an amount of about 1 to 10 mol per 1 mol of compound (9). Where desired, the reaction can also be carried out in the presence of a sulfidizing agent. Examples of the sulfidizing agent include 2,4-bis(4-methoxyphenyl)-1,3,2,4-dithiadiphosphetane-2,4-disulfide (Lawesson's reagent) and the like. The sulfidizing agent is used in an amount of about 1 to mol per 1 mol of compound (9). This reaction is advantageously carried out in a solvent inert to the reaction. The solvent is not particularly limited as long as the reaction proceeds. Preferable examples thereof include ethers, aromatic hydrocarbons, saturated hydrocarbons, amides, halogenated hydrocarbons, nitriles, sulfoxides, aromatic organic bases, mixed solvent thereof and the like. In addition, when an acidic substance is generated due to the reaction, the reaction can be carried out in the presence of an acid scavenger to remove the acidic substance from the reaction system. Examples of the acid scavenger include basic salts, organic bases and the like. In addition, for example, basic salts, organic bases and the like can also be used to promote the reaction. While the reaction time varies depending on the kind of the reagent and solvent to be used, it is generally 1 min to 72 hr. The reaction temperature is preferably 0 to 150° C.

(Step A-4)

Compound (I) can be produced by reacting compound (6) with compound (10). The reaction is carried out in the same manner as in the method in Step A-1. Compound (10) may be a commercially available product, or can also be produced according to a method known per se or a method analogous thereto.

Compound (13), compound (15) or compound (20) can be produced from compound (6) according to Production Method B.

$R^4$ and $R^6$ are each an optionally substituted hydrocarbon group.

$R^5$ and $R^7$ are each a hydrogen atom, a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-14}$ aralkyl group, a $C_{8-13}$ arylalkenyl group or a heterocyclic group (e.g., an aromatic heterocyclic group, a non-aromatic heterocyclic group), each of which is optionally substituted.

The "hydrocarbon group" of the "optionally substituted hydrocarbon group" for $R^4$ and $R^6$ optionally has 1 to 5 (preferably 1 to 3) substituents at substitutable position(s). Examples of the substituent include substituents selected from the aforementioned substituent group A. When the number of the substituents is plural, the respective substituents may be the same or different.

The "$C_{1-10}$ alkyl group", the "$C_{2-10}$ alkenyl group", the "$C_{3-10}$ cycloalkyl group", the "$C_{3-10}$ cycloalkenyl group", the "$C_{6-14}$ aryl group", the "$C_{7-14}$ aralkyl group", the "$C_{8-13}$ arylalkenyl group" or the "heterocyclic group" for $R^5$ and $R^7$ optionally has 1 to 5 (preferably 1 to 3) substituents at substitutable position(s). Examples of the substituent include substituents selected from the aforementioned substituent group A. When the number of the substituents is plural, the respective substituents may be the same or different.

[Production Method B]

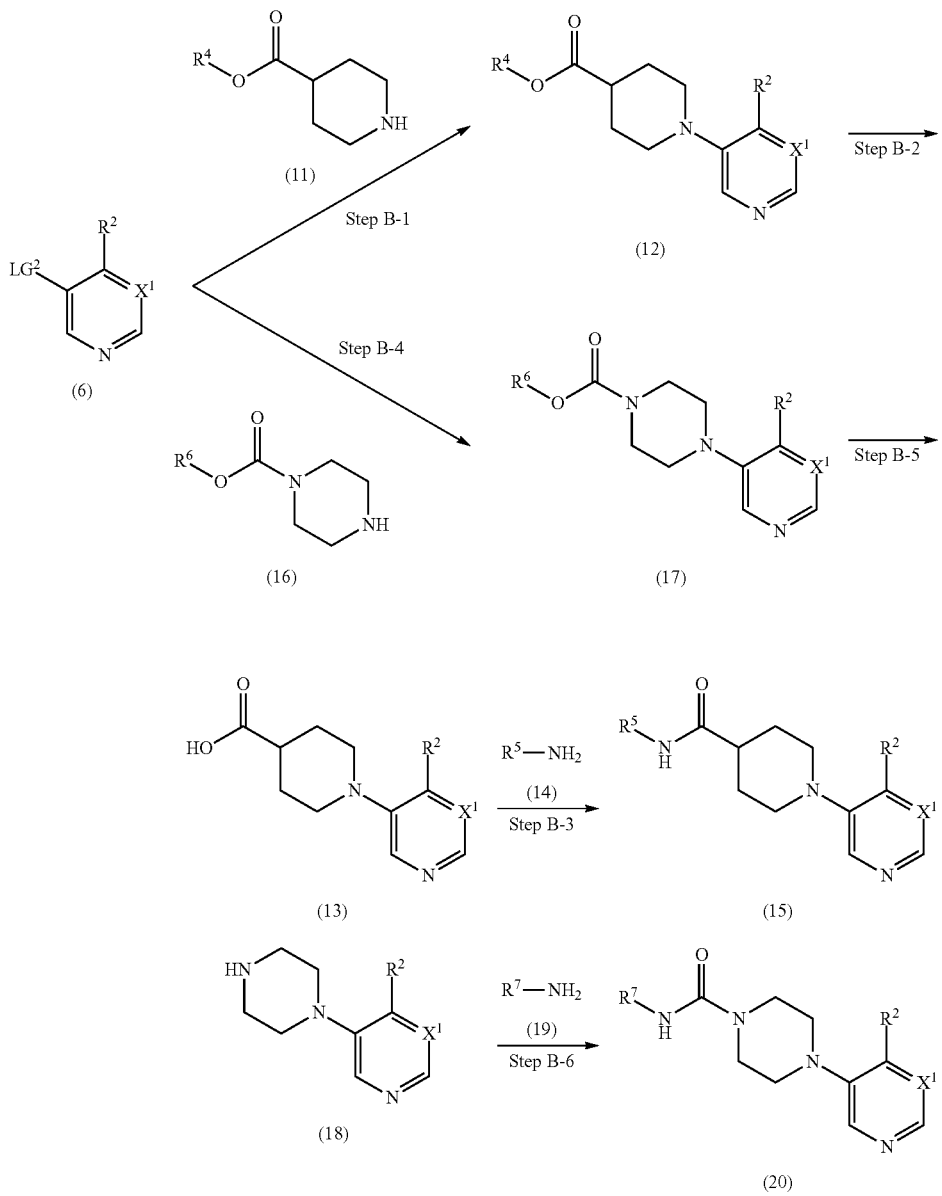

(Step B-1)
Compound (12) can be produced by reacting compound (6) with compound (11). The reaction is carried out in the same manner as in the method in Step A-1. Compound (11) may be a commercially available product, or can also be produced according to a method known per se or a method analogous thereto.

(Step B-2)
Compound (13) can be produced by subjecting compound (12) to hydrolysis. The hydrolysis reaction can be carried out using an inorganic base or an inorganic acid, under a reaction condition generally used for a hydrolysis reaction. It can be carried out according to a method known per se, for example, the method described in "Protective Groups in Organic Synthesis, 3rd Ed", Wiley-Interscience (1999) (Theodora W. Greene, Peter G. M. Wuts), or the like.

(Step B-3)
Compound (15) can be produced by subjecting compound (13) to condensation with compound (14). The reaction is carried out in the same manner as in the method in Step A-2. Compound (14) may be a commercially available product, or can also be produced according to a method known per se or a method analogous thereto.

(Step B-4)
Compound (17) can be produced by reacting compound (6) with compound (16). The reaction is carried out in the same manner as in the method in Step A-1. Compound (16) may be a commercially available product, or can also be produced according to a method known per se or a method analogous thereto.

(Step B-5)
Compound (18) can be produced by removing the carbamate group of compound (17). The removal of the carbamate group can be carried out according to a method known per se, for example, the method described in "Protective Groups in Organic Synthesis, 3rd Ed", Wiley-Interscience (1999) (Theodora W. Greene, Peter G. M. Wuts), or the like.

(Step B-6)

Compound (20) can be produced by subjecting compound (18) to condensation with compound (19). The reaction is carried out by reacting the reactive derivative of compound (18) with compound (19), by directly reacting compound (18) with compound (19) in the presence of a suitable condensing agent, or the like. Examples of the reactive derivative include carboxamide with imidazole and the like, and the like. Examples of the condensing agent include phosgenes such as phosgene, triphosgene and the like, azolides such as N,N'-carbonyldiimidazole and the like, and the like. The reaction is considered to proceed via a reactive derivative of compound (18) by using a condensing agent. Compound (19) is generally used in an amount of about 0.8 to 5 mol, per 1 mol of compound (18) or a reactive derivative thereof. This reaction is advantageously carried out in a solvent inert to the reaction. The solvent is not particularly limited as long as the reaction proceeds. Preferable examples thereof include ethers, aromatic hydrocarbons, saturated hydrocarbons, amides, halogenated hydrocarbons, nitriles, sulfoxides, aromatic organic bases, mixed solvent thereof and the like. In addition, when an acidic substance is generated due to the reaction, the reaction can be carried out in the presence of an acid scavenger to remove the acidic substance from the reaction system. Examples of the acid scavenger include basic salts, organic bases and the like. In addition, for example, basic salts, organic bases and the like can also be used to promote the reaction. While the reaction time varies depending on the kind of the reagent and solvent to be used, it is generally 1 min to 72 hr. The reaction temperature is preferably 0 to 100° C.

In compound (I), for example, compound (Ia), compound (Ib) or compound (Ic) can also be produced from compound (13), compound (15) or compound (20) respectively according to Production Method C.

$R^8$ is a radiolabeled $C_{1-6}$ alkyl group (e.g., $^{18}FCH_2-$, $^{18}FCD_2-$, $^{18}FCH_2CH_2-$, $^{18}FCD_2-CD_2-$, $^{11}CH_3-$, etc.).

"n" is 1, 2, or 3.

[Production Method C]

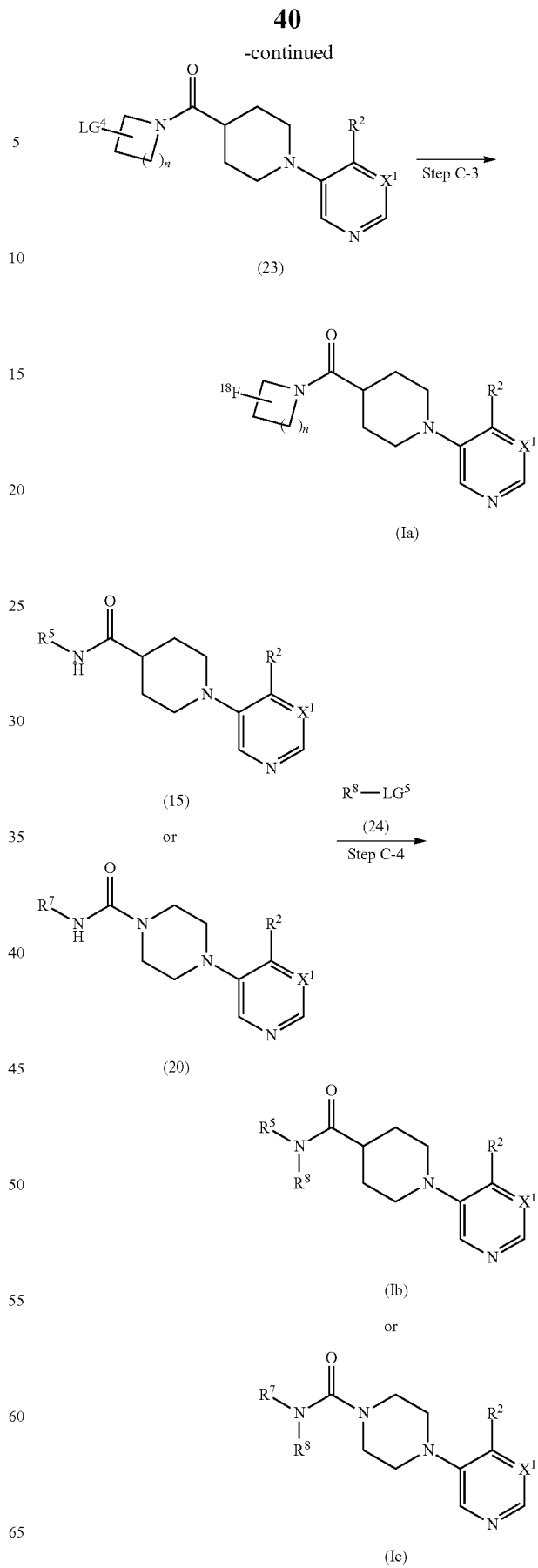

(Step C-1)

Compound (22) can be produced by subjecting compound (13) to condensation with compound (21). The reaction is carried out in the same manner as in the method in Step A-2. Compound (21) may be a commercially available product, or can also be produced according to a method known per se or a method analogous thereto.

(Step C-2)

Compound (23) can be produced by transforming the hydroxyl group of compound (22) into a suitable leaving group as defined above. This transformation can be carried out according to a method known per se, for example, the method described in "Comprehensive Organic Transformations, 2nd Ed", Wiley-Interscience (1999) (Richard C. Larock), or the like.

(Step C-3)

Compound (Ia) can be produced by reacting compound (23) with a nucleophilic radioactive fluorinating reagent, such as K[$^{18}$F]/Kryptofix-222 (trade name) or tetrabutyl ammonium salts incorporating radioactive fluoride under a condition known per se or a condition analogous thereto.

(Step C-4)

Compound (Ib) or Compound (Ic) can be produced by, reacting compound (15) or compound (20) with compound (24). The reaction is carried out in the presence of a base, such as potassium carbonate/Kryptofix-222 (trade name) or cesium carbonate under a condition known per se or a condition analogous thereto. Compound (24) can also be produced according to a method known per se or a method analogous thereto.

Compound (I) of the present invention obtained by the above methods can be purified by chromatography. In addition, compounds (I) can be isolated and purified by, for example, a general separation means such as recrystallization, distillation, chromatography and the like.

In any of the above-mentioned production methods and steps, when desired, compound (I) can be synthesized by a known protection and deprotection, acylation reaction, alkylation reaction, hydrogenation reaction, oxidation reaction, reduction reaction, carbon chain extension reaction, substituent exchange reaction and the like, which may be used alone or in a combination of two or more thereof.

As in the case of the compound (I), a prodrug of the compound (I) can be used. The prodrug of the compound (I) is a compound that is converted to a compound (I) by reactions using enzymes or gastric acid under physiological conditions in vivo. Namely, it includes a compound that is converted to a compound (I) by enzymatic oxidation, reduction and hydrolysis or a compound that is converted to a compound (I) by hydrolysis using gastric acid.

Prodrugs of the compound (I) include compounds wherein an amino group in the compound (I) is acylated, alkylated or phosphorylated (e.g., the amino group in the compound (I) is eicosanoylated, alanylated, pentylaminocarbonylated, (5-methyl-2-oxo-1, 3-dioxolen-4-yl) methoxycarbonylated, tetrahydrofuranylated, pyrrolidylmethylated, pivaloyloxymethylated or tert-butylated); the hydroxyl group in the compound (I) is acylated, alkylated, phosphorylated or borated (e.g., the hydroxyl group in the compound (I) is acetylated, palmitoylated, propanoylated, pivaloylated, succinylated, fumarylated, alanylated, dimethylaminomethylcarbonylated); the carboxyl group in the compound (I) is esterified or amidated (e.g., the carboxyl group in the compound (I) is ethyl-esterified, phenyl-esterified, carboxymethyl-esterified, dimethylaminomethyl-esterified, pivaloyloxymethyl-esterified, ethoxycarbonyloxyethyl-esterified, phthalidyl-esterified, (5-methyl-2-oxo-1,3-dioxolen-4-yl)methyl-esterified, cyclohexyloxycarbonylethyl-esterified, or methylamidated). These compounds can be produced from the compound (I) by the known methods. Prodrugs of the compound (I) can be converted to the compound (I) under the physiological conditions as described in "Development of Drugs" Vol. 7 Molecular Design published in 1990 by Hirokawa Shoten, page 163 to 198.

In an embodiment, the compounds of the present invention may be labeled as radiotracers for in vitro imaging. In another embodiment, the compounds of the invention may be prepared as Positron Emission Tomograph (PET) tracers for in vivo imaging and quantification of CH24H.

Suitable radionuclides that may be incorporated in the instant compounds include, but not limited, $^{3}$H (also written as T), $^{11}$C, $^{18}$F, $^{35}$S, $^{125}$I, $^{82}$Br, $^{123}$I, $^{131}$I, $^{75}$Br, $^{15}$O, $^{13}$N, $^{211}$At or $^{77}$Br. The radionuclide that is incorporated in the instant radiolabeled compounds will depend on the specific analytical or pharmaceutical application of that radiolabeled compound.

Thus, for in vitro imaging of CH24H and competition assays, compounds that incorporate $^{3}$H, $^{35}$S, $^{125}$I or $^{82}$Br will generally be most useful. For PET tracers, compounds that incorporate a radionuclide selected from $^{11}$C, $^{18}$F, $^{123}$I, $^{131}$I, $^{75}$Br, $^{76}$Br or $^{77}$Br are preferred. In certain applications incorporation of a chelating radionuclide such as Tc$^{99m}$ may also be useful. In other applications $^{18}$F may be preferable over $^{11}$C because with the longer half-life of $^{18}$F, imaging can be carried out long enough to allow a more specific signal to develop and improved conditions for quantification studies of target protein. Compounds can be radiolabeled with either positron or gamma emitting radionuclides.

Radiolabeled CH24H inhibitors, when labeled with the appropriate radionuclide, are potentially useful for a variety of in vitro and/or in vivo imaging applications. Specific examples of possible imaging applications include, but are not limited to, determining the location of, the relative activity of and/or quantifying CH24H, radioimmunoassays of CH24H inhibitors, and autoradiography to determine the distribution of CH24H in a mammal or an organ or tissue sample thereof. Using a fluorine-18 or carbon-11 labeled radiotracer that provides a CH24H-specific image in the brain and other tissues, the dose required to effectively inhibit the CH24H enzyme can be determined by the blockade of the PET radiotracer image in humans.

In a specific embodiment, the instant radiolabeled CH24H inhibitors when labeled with the positron emitting radionuclide, such as $^{11}$C, $^{18}$F, $^{15}$O and $^{13}$N, are useful for positron emission tomographic (PET) imaging of CH24H in the brain of living humans and experimental animals. These radiolabeled CH24H inhibitors may be used as research tools to study the interaction of unlabeled CH24H inhibitors with CH24H in vivo via competition between the unlabeled drug and the radiolabeled compound for binding to the enzyme. These types of quantitative studies are useful for determining the relationship between CH24H occupancy and the dose of unlabeled CH24H inhibitor, as well as for studying the duration of blockade of the enzyme by various doses of the unlabeled CH24H inhibitors. As a clinical tool, the radiolabeled CH24H inhibitors may be used to help define a clinically efficacious dose of a CH24H inhibitor. In animal experiments, the radiolabeled CH24H inhibitors can be used to provide information that is useful for choosing between potential drug candidates for selection for clinical development. The radiolabeled CH24H inhibitors may also be used to study the regional distribution and concentration of CH24H in the living human brain, as well as the brain of living experimental animals and in tissue samples. The radiolabeled CH24H inhibitors may also be used to study disease or pharmacologically related changes in CH24H concentrations.

In specific embodiments of the invention, PET tracers such as the present radiolabeled CH24H inhibitors and currently available PET technology can be used, but is not limited to, to obtain the following information: relationship between level of target occupancy by candidate CH24H inhibitors and clinical efficacy in patients; dose selection for clinical trials of CH24H inhibitors prior to initiation of long term clinical studies; comparative potencies of structurally novel CH24H inhibitors; investigating the influence of CH24H inhibitors on in vivo transporter affinity and density during the treatment of clinical targets with CH24H inhibitors and other agents; changes in the density and distribution of CH24H, for example, 1) during the active stage of a neurodegenerative disease or condition, 2) for the evaluation of efficacy during treatment, or 3) during remission; changes in CH24H expression and distribution in CNS disorders; imaging neurodegenerative disease when CH24H is upregulated; imaging neurodegenerative disease when CH24H is involved; and the like.

Isotopically-labeled compounds of formula (I) can generally be prepared by conventional techniques known to those skilled in the art or by processes analogous to those described in the accompanying Examples using appropriate isotopically-labeled reagents in place of the non-labeled reagent previously employed to produce radiolabeled derivatives.

The radiolabeled CH24H inhibitors of the present invention have utility in imaging CH24H or for diagnostic imaging with respect to any of the mentioned neurological and psychiatric disorders associated with CH24H dysfunction.

The present invention is also directed to a method for quantitative imaging of CH24H in a mammal which comprises administering to a mammal in need of such quantitative imaging an effective amount of the radiolabeled compound of the present invention.

The present invention is also directed to a method for quantitative imaging of tissues bearing CH24H in a mammal which comprises administering to a mammal in need of such quantitative imaging an effective amount of the radiolabeled compound of the present invention.

The present invention is also directed to a method for quantitative imaging of CH24H in tissues of a mammalian species which comprises administering to the mammalian species in need of such quantitative imaging an effective amount of the radiolabeled compound of the present invention.

The present invention is also directed to a method for quantitative imaging of CH24H in the brain in a mammal which comprises administering to a mammal in need of such quantitative imaging an effective amount of the radiolabeled compound of the present invention.

The present invention is further directed to a method for the detection or quantification of CH24H in mammalian tissue which comprises administering to a mammal in which such quantification is desired an effective amount of the radiolabeled compound of the present invention.

In a specific embodiment of the methods of the present invention, the mammal is a human.

The radiolabeled compound of the present invention is utility in imaging CH24H or for diagnostic imaging with respect to neurodegenerative disease (e.g., Alzheimer's disease, mild cognitive disorder, Huntington's disease, Parkinson's disease, multiple sclerosis, amyotrophic lateral sclerosis, Complications related to traumatic brain injury, Post concussive syndrome, Shaken Baby Syndrome, cerebral infarction, glaucoma, Hearing loss due to nerve degeneration, Spinal cord injury, frontotemporal dementia, Dementia with Lewy body and the like), epilepsy, schizophrenia, Seizure, Migraine, Hepatic Encephalopathy, Age-related Macular Degeneration, Pain (e.g., Neuropathic pain, Inflammatory pain), Obsessive-Compulsive Disorder, Anxiety disorder, Posttraumatic stress disorder, substance use disorder, Palatal myoclonus, Phantom pain, autism, Opioid dependence, systemic lupus erythematosus, AIDS-related dementia complex, major depressive disorder, Radiation somnolence syndrome and down syndrome in mammals (e.g., humans, cows, horses, dogs, cats, monkeys, mice, rats, etc. particularly in humans).

The compound of the present invention can be administered safely, as it is, or in a dosage form which is manufactured, alone or together, in suitable dosage unit formulations containing conventional non-toxic pharmaceutically acceptable carriers, adjuvants and vehicles appropriate for each route of administration, according to a per se known method for manufacturing pharmaceutical formulations (e.g., methods described in Japanese Pharmacopoeia) such as tablets (inclusive of sugar coated tablet, film coated tablet, sublingual tablet, orally disintegrable tablet, and buccal), pills, powders, granules, capsules (inclusive of soft capsule, and microcapsule), troches, syrups, liquid dosage forms, emulsions, controlled-release preparations (e.g., quick-release preparation, sustained-release preparation, sustained-release microcapsule), aerosols, films (e.g., orally disintegrable film, adhesive film for application to oral-cavity mucosa), injections (e.g., subcutaneous injection, intravenous injection, intramuscular injection, intraperitoneal injection, ICV, intracisternal injection), drip infusion, implant, percutaneous absorbent, ointment, lotion, patch, suppositories (e.g., rectal suppository, vaginal suppository), pellets, transnasal preparations, pulmonary preparations (inhalant), inhalation spray, eye drops and the like, in an oral or parenteral route (e.g., intravenous, intramuscular, subcutaneous, intraorgan, intranasal, intradermal, ophthalmic instillation, intracerebral, intrarectal, intravaginal, intraperitoneal, nasal, vaginal, rectal sublingual, directly to lesion).

Here, as a pharmaceutical acceptable carrier, common organic or inorganic carrier substances are used as formulation raw materials. Carriers are added as vehicles, lubricants, binders and disintegrants in the solid formulations; and as solubilizing agents, suspending agents, isotonization agents, buffers and soothing agents in the liquid formulations. If desired, formulation additives such as antiseptics, antioxidants, colorants, sweeteners, etc. can be used.

Favorable examples of the vehicles are as follows: lactose, sucrose, D-mannitol, D-sorbitol, starch, α-starch, dextrin, crystalline cellulose, low-substituted hydroxypropyl cellulose, sodium carboxymethylcellulose, gum Arabic, pullulan, light silicic anhydride, synthetic aluminum silicate and magnesium metasilicic aluminate.

Favorable examples of the lubricants include magnesium stearate, calcium stearate, talc and colloidal silica.

Favorable examples of the binders are as follows: α-starch, sucrose, gelatin, gum Arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropyl methyl cellulose and polyvinylpyrrolidone.

Favorable examples of the disintegrants are as follows: lactose, sucrose, starch, carboxymethylcellulose, calcium carboxymethylcellulose, croscarmellose sodium, sodium carboxymethyl starch, light silicic anhydride and low-substituted hydroxypropylcellulose.

Favorable examples of the solvents are as follows: water for injection, physiological saline, Linger solution, alcohol, propylene glycol, polyethylene glycol, sesame oil, corn oil, olive oil and cottonseed oil.

Favorable examples of the solubilizing agents are as follows: polyethylene glycol, propylene glycol, D-mannitol, trehalose, benzylbenzoate, ethanol, tris-aminomethane, cholesterol, triethanolamine, sodium carbonate, sodium citrate, sodium salicylate and sodium acetate.

Favorable examples of the suspending agents are as follows: surfactants such as stearyl triethanolamine, sodium lauryl sulfate, laurylamino propionic acid, lecithin, benzalkonium chloride, benzethonium chloride, and glycerin monostearate; hydrophilic polymers such as polyvinyl alcohol, polyvinyl pyrrolidone, sodium carboxymethylcellulose, methylcellulose, hydroxymethyl cellulose, hydroxyethyl cellulose and hydroxypropyl cellulose; polysorbates, and polyoxyethylene-hardened castor oil.

Favorable examples of the isotonization agents include sodium chloride, glycerin, D-mannitol, D-sorbitol and glucose.

Favorable examples of the buffers include buffer solutions of phosphates, acetates, carbonates and citrates.

Favorable examples of the soothing agents include benzyl alcohol.

Favorable examples of antiseptics include para-oxybenzoic acid esters, chlorobutanol, benzyl alcohol, phenethyl alcohol, dehydroacetic acid and sorbic acid.

Favorable examples of antioxidants include sulfites and ascorbates.

Favorable examples of the colorants include water soluble edible tar dyes (e.g., edible dyes such as Food Red No. 2 and No. 3, Food Yellow No. 4 and No. 5, Food Blue No. 1 and 2); water insoluble lake dyes (e.g., aluminum salts of the aforementioned water soluble edible tar dyes), natural dyes (e.g., β-carotene, chlorophyll, red iron oxide).

Favorable examples of the sweeteners include sodium saccharin, dipotassium glycyrrhizate, aspartame and stevia.

The medical compositions of the present invention can be manufactured by the common methods in the field of formulation technology, for example, methods listed in the Japanese pharmacopoeia. Specific manufacturing methods for formulations are described in detail below.

The content of the compound of the present invention in the medical compositions of the present invention varies based on the dosage forms, dosages of the compound of the present invention, etc. For example, the content approximately ranges from 0.01 to 100 wt % and preferably from 0.1 to 95 wt % relative to the entire amount of the composition.

All the compounds disclosed in the present application, WO 2013/054822 A1, WO 2014/061676 A1, WO 2014/092100 A1, WO 2014/163161 A1 and WO 2014/163162 A1 have a superior CH24H inhibitory action and can suppress nerve cell death, Aβ increase, intracerebral inflammation and the like.

Accordingly, all the compounds disclosed in the present application, WO 2013/054822 A1, WO 2014/061676 A1, WO 2014/092100 A1, WO 2014/163161 A1 and WO 2014/163162 A1 are useful for the prophylaxis, improvement of symptoms, suppression of progression or treatment of diseases involving enhanced function of CH24H, for example, neurodegenerative disease.

In the present specification, the "neurodegenerative disease" means a disease associated with denaturation of neural tissues.

Specific examples of the neurodegenerative disease include Alzheimer's disease, mild cognitive disorder, Huntington's disease, Parkinson's disease, multiple sclerosis, amyotrophic lateral sclerosis, complications related to traumatic brain injury, post concussive syndrome, shaken baby syndrome, cerebral infarction, glaucoma, hearing loss due to nerve degeneration, frontotemporal dementia, spinal cord injury, dementia with Lewy body, alcoholic dementia or other drug-related dementia, multiple system atrophy, Pick's disease, Niemann-Pick's disease, corticobasal degeneration, vascular dementia, motor neuron disease (MND), Creutzfeldt-Jakob disease or prion disease, cerebral palsy, progressive supranuclea palsy, multiple sclerosis, neuromyopathy and the like.

In addition, all the compounds disclosed in the present application, WO 2013/054822 A1, WO 2014/061676 A1, WO 2014/092100 A1, WO 2014/163161 A1 and WO 2014/163162 A1 are useful for the prophylaxis, improvement of symptoms, suppression of progression or treatment of diseases, for example, epilepsy, schizophrenia, seizure, migraine, hepatic encephalopathy, age-related macular degeneration, pain (e.g., neuropathic pain, inflammatory pain), obsessive-compulsive disorder, anxiety disorder, post-traumatic stress disorder, substance use disorder, palatal myoclonus, phantom pain, autism, opioid dependence, systemic lupus erythematosus, AIDS-related dementia complex, major depressive disorder, Radiation somnolence syndrome, depression, minor depressive disorder, bipolar depression, dysthymic disorder, affective disorder (e.g., seasonal affective disorder etc.), recurrent depression, postpartum depression, stress-related disorder, major depressive disorder associated with psychopathia (including delusional disorder and schizophrenia), mania or mixed mood episode, hypomanic mood episode, depressive episode accompanied by atypical characteristic, depressive episode accompanied by depressive characteristic, depressive episode accompanied by tensional characteristic, post-stroke depressive episode, delirium, dementia peripheral symptom (psychological symptom or behavior abnormality), anxiety, generalized anxiety disorder, anxiety syndrome, mood disorder, cyclothymic disorder, premenstrual dysphoric disorder, panic disorder, phobia, social phobia, social anxiety disorder, posttraumatic stress syndrome, posttraumatic stress disorder, paranoid personality disorder, schizoaffective disorder depressive or bipolar type, Tourette syndrome, autism, fragile X syndrome, Rett syndrome, adjustment disorder, bipolar disorder (including type I bipolar disorder and type II bipolar disorder), neurosis, schizophrenia (e.g., positive symptom, negative symptom, disorder of memory, paranoid schizophrenia, disorganized schizophrenia, catatonic schizophrenia, undifferentiated schizophrenia, residual schizophrenia), schizophreniform disorder, chronic fatigue syndrome, anxiety neurosis, obsessive-compulsive disorder, panic disorder, anxiety symptom, dysphoria, dysthymia, cyclothymia, nervous erethism, syncope, addiction, loss of sexual desire, attention-deficit hyperactivity disorder (ADHD), refractory major depression, treatment-resistant depression, psychotic disorder (e.g., short-term psychotic disorder, shared psychotic disorder), psychosis triggered by alcohol, amphetamine, cannabis, cocaine, hallucinatory drug, obesity, inhaled drug, opioid or phencyclidine, delusional disorder, Noonan syndrome, Angelman syndrome, Prader-Willi syndrome, Beckwith-Wiedemann syndrome, Silver-Russell syndrome, nodular sclerosis, Williams syndrome, Kallmann's syndrome, Rubinstein-Taybi syndrome, motility disorder, hypophrenia, paranoid tendency, amnestic disorder, mild cognitive impairment, learning disorder (e.g., reading disorder, mathematics disorder, disorder of written expression), age-associated cognitive and memory disorder [e.g., age-related memory disorder, senile dementia], sleep disorder [e.g., intrinsic sleep disorder (e.g., psycophysioloical insomnia etc), extrinsic sleep disorder, circadian rhythm disorder (e.g., time zone change syndrome (jet lag), shift work sleep disorder, irregular type sleep-wake pattern, sleep phase delay syndrome, advanced sleep phase syndrome, non-24-hour sleep-wake disorder etc.), parasomnia,
sleep disorder associated with internal medical or psychiatric disorder (e.g., chronic obstructive pulmonary disease, Alzheimer's disease, Parkinson's disease, vascular dementia, schizophrenia, depression, anxiety neurosis), stress-related insomnia, insomnia, insomnia neurosis, sleep apnea syndrome], respiratory depression due to anesthetic, traumatic disorder, neurodegenerative disease and the like, pain [e.g., psychogenic pain (somatoform disorder, pain disorder, somatization disorder, hypochondriasis, conversion disorder, chronic pain associated with depression), inflammatory pain, peripheral neuropathic pain, central neuropathic pain, neuropathic pain, acute pain, intractable pain, cancerous continuous pain, cancerous breakthrough pain, cancerous pain, continuous pain, body pain, breakthrough pain, chronic pain, tenderness, general pain, dull pain, dermatalgia, irradiating pain, pain, post-thoracotomy pain syndrome], deafness [e.g., Kanamycin deafness, streptomycin deafness, toxic deafness, senile deafness, idiopathic bilateral sensorineural hearing loss, sudden deafness, acquired deaf mutism, genetic deafness, organic deafness, high-tone sensorineural hearing loss, occupational hearing loss, occupational deafness, low-tone sensorineural hearing loss], stroke, age-related macular degeneration, oculopalatal tremor, anorexia nervosa, eating disorder, anorexia nervosa, bulimia, other eating disorder, alcoholism, alcohol misuse, alcohol amnestic disorder, alcohol paranoia, alcohol preference, alcohol withdrawal, alcoholic insanity, alcohol poisoning, alcoholic jealousy, alcoholic mania, alcohol-dependent psychiatric disorder, alcoholic psychosis, pharmacophilia, pharmacophobia, pharmacomania, drug abuse, drug dependence, drug withdrawal, stress-related headache, tension headache, diabetic neuropathy, obesity, diabetes, muscle spasm, Meniere's disease, dysautonomia, alopecia, glaucoma, hypertension, cardiac disease, tachycardia, congestive heart failure, hyperventilation, asthma bronchiale, apnea, sudden infant death syndrome, inflammatory disease, allergic disease, impotence, climacteric disorder, infertility, cancer, immune deficiency syndrome due to HIV infection, immune deficiency syndrome due to stress, cerebrospinal meningitis, acromegaly, incontinence, metabolic syndrome, osteoporosis, peptic ulcer, irritable bowel syndrome, inflammatory bowel disease, ulcerous colitis, Crohn's disease, stress gastrointestinal disorder, nervous vomiting, peptic ulcer, diarrhea, constipation, postoperative ileus and the like in mammals (e.g., humans, cows, horses, dogs, cats, monkeys, mice, rats, etc. particularly in humans) and the like.

When all the compounds disclosed in the present application, WO 2013/054822 A1, WO 2014/061676 A1, WO 2014/092100 A1, WO 2014/163161 A1 and WO 2014/163162 A1 are applied to each of the above-mentioned diseases, it can be used in an appropriate combination with a medicament or a treatment method generally employed for the disease.

Examples of the medicament (hereinafter to be abbreviated as "concomitant drug") to be used in combination with all the compounds disclosed in the present application, WO 2013/054822 A1, WO 2014/061676 A1, WO 2014/092100 A1, WO 2014/163161 A1 and WO 2014/163162 A1 include acetylcholine esterase inhibitors (e.g., donepezil, rivastigmine, galanthamine, zanapezil etc.), antidementia agents (e.g., memantine), inhibitors of β amyloid protein production, secretion, accumulation, coagulation and/or deposition, β secretase inhibitors (e.g., 6-(4-biphenyl)methoxy-2-[2-(N,N-dimethylamino)ethyl]tetralin, 6-(4-biphenyl)methoxy-2-(N,N-dimethylamino)methyltetralin, 6-(4-biphenyl)methoxy-2-(N,N-dipropylamino)methyltetralin, 2-(N,N-dimethylamino)methyl-6-(4'-methoxybiphenyl-4-yl)methoxytetralin, 6-(4-biphenyl)methoxy-2-[2-(N,N-diethylamino)ethyl]tetralin, 2-[2-(N,N-dimethylamino)ethyl]-6-(4'-methylbiphenyl-4-yl)methoxytetralin, 2-[2-(N,N-dimethylamino)ethyl]-6-(4'-methoxybiphenyl-4-yl)methoxytetralin, 6-(2',4'-dimethoxybiphenyl-4-yl)methoxy-2-[2-(N,N-dimethylamino)ethyl]tetralin, 6-[4-(1,3-benzodioxol-5-yl)phenyl]methoxy-2-[2-(N,N-dimethylamino)ethyl]tetralin, 6-(3',4'-dimethoxybiphenyl-4-yl)methoxy-2-[2-(N,N-dimethylamino)ethyl]tetralin, an optically active form thereof, a salt thereof and a hydrate thereof, OM99-2 (WO01/00663)), γ secretase inhibitory agent, β amyloid protein coagulation inhibitory agent (e.g., PTI-00703, ALZHEMED (NC-531), PPI-368 (JP-A-11-514333), PPI-558 (JP-A-2001-500852), SKF-74652 (Biochem. J. (1999), 340(1), 283-289)), β amyloid vaccine, β amyloid degrading enzyme and the like, cerebral function activators (e.g., aniracetam, nicergoline), other therapeutic drug for Parkinson's disease [(e.g., dopamine receptor agonists (e.g., L-DOPA, bromocriptine, pergolide, talipexole, pramipexole, cabergoline, amantadine), a monoamine oxidase (MAO) inhibitors (e.g., deprenyl, Selgiline (selegiline), remacemide, riluzole), anticholinergic agents (e.g., trihexyphenidyl, biperiden), COMT inhibitors (e.g., entacapone)], therapeutic drug for amyotropic lateral sclerosis (e.g., riluzole etc., neurotrophic factor), therapeutic drug for abnormal behavior wandering and the like due to the progress of dementia (e.g., sedative drug, antianxiety drug), apoptosis inhibitors (e.g., CPI-1189, IDN-6556, CEP-1347), neuronal differentiation or regeneration promoters (e.g., leteprinim, xaliproden (SR-57746-A), SB-216763, Y-128, VX-853, prosaptide, 5,6-dimethoxy-2-[2,2,4,6,7-pentamethyl-3-(4-methylphenyl)-2,3-dihydro-1-benzofuran-5-yl]isoindoline, 5,6-dimethoxy-2-[3-(4-isopropylphenyl)-2,2,4,6,7-pentamethyl-2,3-dihydro-1-benzofuran-5-yl]isoindoline, 6-[3-(4-isopropylphenyl)-2,2,4,6,7-pentamethyl-2,3-dihydro-1-benzofuran-5-yl]-6,7-dihydro-5H-[1,3]dioxolo[4,5-f]isoindole and optically active forms, salts and hydrates thereof), antidepressants (e.g., desipramine, amitriptyline, imipramine, tramadol), antiepilepsy drug (e.g., lamotrigine), antianxiety drugs (e.g., benzodiazepine), non-steroidal anti-inflammatory drugs (e.g., meloxicam, tenoxicam, indomethacin, ibuprofen, celecoxib, rofecoxib, aspirin, indomethacin), disease-modifying anti-rheumatic drugs (DMARDs), anti-cytokine drugs (e.g., TNF inhibitor MAP kinase inhibitor), steroidal drugs (e.g., dexamethasone, hexestrol, cortisone acetate), therapeutic agents for incontinence or frequent urination (e.g., flavoxate hydrochloride, oxybutynin hydrochloride, propiverine hydrochloride), phosphodiesterase inhibitors (e.g., sildenafil (citrate)), dopamine agonists (e.g., apomorphine etc.), antiarrhythmics (e.g., mexiletine), sex hormones or derivatives thereof (e.g., progesterone, estradiol, estradiol benzoate), therapeutic agents for osteoporosis (e.g., alfacalcidol, calcitriol, elcatonin, calcitonin salmon, estriol, ipriflavone, disodium pamidronate, sodium alendronate hydrate, disodium incadronate), parathyroid hormone (PTH), calcium receptor antagonists, therapeutic drugs for insomnia (e.g., benzodiazepine medicament, non-benzodiazepine medicament, melatonin agonist), therapeutic drugs for schizophrenia (e.g., typical antipsychotic agents such as haloperidol and the like; atypical antipsychotic agents such as clozapine, olanzapine, risperidone, aripiprazole and the like; medicament acted on metabotropic glutamate receptor or ionic channel-conjugated glutamate receptor; phosphodiesterase inhibitor) and the like.

In addition, a combined use with a transplantation method of neural stem cell or neural precursor cell prepared from embryonic stem cell or nervous tissue, or fetal neural tissue, and a combined use with a pharmaceutical agent such as an immunosuppressant after the transplantation and the like.

Furthermore, all the compounds disclosed in the present application, WO 2013/054822 A1, WO 2014/061676 A1, WO 2014/092100 A1, WO 2014/163161 A1 and WO 2014/163162 A1 may be used in combination with the following concomitant drugs.

(1) Therapeutic Agent for Diabetes

For example, insulin preparations (e.g., animal insulin preparation extracted from the pancreas of bovine, swine; human insulin preparation genetically synthesized using *Escherichia coli*, yeast; zinc insulin; protamine zinc insulin; insulin fragment or derivatives (e.g., INS-1), oral insulin preparation), insulin sensitizer (e.g., pioglitazone or a salt thereof (preferably hydrochloride), rosiglitazone or a salt thereof (preferably maleate), Tesaglitazar, Ragaglitazar, Muraglitazar, Edaglitazone, Metaglidasen, Naveglitazar, AMG-131, THR-0921), α-glucosidase inhibitor (e.g., voglibose, acarbose, miglitol, emiglitate), biguanide (e.g., metformin, buformin or a salt thereof (e.g., hydrochloride, fumarate, succinate)), insulin secretagogue [sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or calcium salt hydrate thereof, glucose-dependent insulin secretagogue (e.g., [(3S)-6-({2',6'-dimethyl-4'-[3-(methylsulfonyl)propoxy]biphenyl-3-yl}methoxy)-2,3-dihydro-1-benzofuran-3-yl]acetic acid or a salt thereof)], dipeptidyl peptidase IV inhibitor (e.g., Alogliptin, Vildagliptin, Sitagliptin, Saxagliptin, T-6666, TS-021), β3 agonist (e.g., AJ-9677), GPR40 agonist, GLP-1 receptor agonist [e.g., GLP-1, GLP-1MR agent, NN-2211, AC-2993 (exendin-4), BIM-51077, Aib(8,35)hGLP-1(7,37)NH$_2$, CJC-1131], amylin agonist (e.g., pramlintide), phosphotyrosine phosphatase inhibitors (e.g., sodium vanadate), gluconeogenesis inhibitor (e.g., glycogen phosphorylase inhibitor glucose-6-phosphatase inhibitors, glucagon antagonists), SGLUT (sodium-glucose cotransporter) inhibitor (e.g., T-1095), 11β-hydroxysteroid dehydrogenase inhibitor (e.g., BVT-3498), adiponectin or an agonist thereof, IKK inhibitor (e.g., AS-2868), leptin resistance improving drugs, somatostatin receptor agonists, glucokinase activators (e.g., Ro-28-1675), GIP (Glucose-dependent insulinotropic peptide) and the like.

(2) Therapeutic Agents for Diabetic Complications

For example, aldose reductase inhibitors (e.g., tolrestat, epalrestat, zenarestat, zopolrestat, minalrestat, fidarestat, CT-112), neurotrophic factor and an increasing agent thereof (e.g., NGF, NT-3, BDNF, neurotrophic factors and increasing drugs described in WO01/14372 (e.g., 4-(4-chlorophenyl)-2-(2-methyl-1-imidazolyl)-5-[3-(2-methylphenoxy)propyl]oxazole)), nerve regeneration promoting agent (e.g., Y-128), PKC inhibitor (e.g., ruboxistaurin mesylate), AGE inhibitor (e.g., ALT946, pimagedine, pyratoxanthine, N-phenacylthiazolium bromide (ALT766), ALT-711, EXO-226, Pyridorin, pyridoxamine), active oxygen scavengers (e.g., thioctic acid), cerebral vasodilator (e.g., tiapuride, mexiletine), somatostatin receptor agonists (e.g., BIM23190), apoptosis signal regulating kinase-1 (ASK-1) inhibitor and the like can be mentioned.

(3) Therapeutic Agent for Hyperlipidemia

For example, statin compound (e.g., pravastatin, simvastatin, lovastatin, atorvastatin, fluvastatin, rosuvastatin, pitavastatin, or a salt thereof (e.g., sodium salt, calcium salt)), squalene synthase inhibitors (e.g., lapaquistat acetate or a salt thereof), fibrate compound (e.g., bezafibrate, clofibrate, simfibrate, clinofibrate), ACAT inhibitor (e.g., Avasimibe, Eflucimibe), anion exchange resin (e.g., colestyramine), probucol, nicotinic acid drug (e.g., nicomol, niceritrol), ethyl icosapentate, phytosterol (e.g., soysterol, gamma oryzanol) and the like.

(4) Antihypertensive Agent

For example, angiotensin converting enzyme inhibitor (e.g., captopril, enalapril, delapril), angiotensin II antagonist (e.g., candesartan cilexetil, losartan, eprosartan, valsartan, telmisartan, irbesartan, tasosartan, 1-[[2'-(2,5-dihydro-5-oxo-4H-1,2,4-oxadiazol-3-yl)biphenyl-4-yl]methyl]-2-ethoxy-1H-benzimidazole-7-carboxylic acid, Azilsartan, Azilsartan medoxomil), calcium antagonist (e.g., manidipine, nifedipine, amlodipine, efonidipine, nicardipine), potassium channel opener (e.g., levcromakalim, L-27152, AL 0671, NIP-121), clonidine and the like.

(5) Antiobesity Agent

For example, central-acting antiobesity agent (e.g., dexfenfluramine, fenfluramine, phentermine, sibutramine, amfepramone, dexamphetamine, mazindol, phenylpropanolamine, clobenzorex; MCH receptor antagonists (e.g., SB-568849; SNAP-7941; compounds described in WO01/82925 and WO01/87834); neuropeptide Y antagonist (e.g., CP-422935); cannabinoid receptor antagonists (e.g., SR-141716, SR-147778); ghrelin antagonist; 11β-hydroxysteroid dehydrogenase inhibitor (e.g., BVT-3498)), pancreatic lipase inhibitors (e.g., orlistat, cetilistat), β3 agonist (e.g., AJ-9677, AZ40140), anorectic peptides (e.g., leptin, CNTF (ciliary neurotrophic factor)), cholecystokinin agonist (e.g., lintitript, FPL-15849), anorexigenic agent (e.g., P-57) and the like.

(6) Diuretic

For example, xanthine derivative (e.g., theobromine sodium salicylate, theobromine calcium salicylate), thiazide preparation (e.g., ethiazide, cyclopenthiazide, trichloromethyazide, hydrochlorothiazide, hydroflumethiazide, benzylhydrochlorothiazide, penflutizide, polythiazide, methyclothiazide), antialdosterone preparation (e.g., spironolactone, triamterene), carbonic anhydrase inhibitors (e.g., acetazolamide), chlorobenzenesulfonamide agent (e.g., chlortalidone, mefruside, indapamide), azosemide, isosorbide, ethacrynic acid, piretanide, bumetanide, furosemide and the like.

(7) Chemotherapeutic Agent

For example, alkylating agents (e.g., cyclophosphamide, ifosfamide), metabolic antagonists (e.g., methotrexate, 5-fluorouracil or derivative thereof), antitumor antibiotics (e.g., mitomycin, adriamycin), plant-derived antitumor agents (e.g., vincristine, vindesine, Taxol), cisplatin, carboplatin, etoposide and the like. Of these, Furtulon and Neo-Furtulon, which are 5-fluorouracil derivatives, and the like are preferable.

(8) Immunotherapeutic Agent

For example, microorganism or bacterial components (e.g., muramyl dipeptide derivative, Picibanil), polysaccharides having immunity potentiating activity (e.g., lentinan, schizophyllan, krestin), cytokines obtained by genetic engineering techniques (e.g., interferon, interleukin (IL)), colony stimulating factors (e.g., granulocyte colony stimulating factor erythropoietin) and the like, with preference given to interleukins such as IL-1, IL-2, IL-12 and the like.

(9) Antithrombotic Agent

For example, heparin (e.g., heparin sodium, heparin calcium, dalteparin sodium), warfarin (e.g., warfarin potassium), anti-thrombin drug (e.g., argatroban), thrombolytic agent (e.g., urokinase, tisokinase, alteplase, nateplase, monteplase, pamiteplase), platelet aggregation inhibitor (e.g., ticlopidine hydrochloride, cilostazol, ethyl icosapentate, beraprost sodium, sarpogrelate hydrochloride) and the like.

(10) Cachexia Improving Medicament

For example, cyclooxygenase inhibitors (e.g., indomethacin etc.) [Cancer Research, Vol. 49, pages 5935-5939, 1989], progesterone derivatives (e.g., megestrol acetate) [Journal of Clinical Oncology, Vol. 12, pages 213-225, 1994], glucosteroids (e.g., dexamethasone etc.), metoclopramide agents, tetrahydrocannabinol agents (publications are all as mentioned above), fat metabolism improving agents (e.g., eicosapentaenoic acid etc.) [British Journal of Cancer, Vol. 68, pages 314-318, 1993], growth hormones, IGF-1, or antibodies to a cachexia-inducing factor such as TNF-α, LIF, IL-6, oncostatin M and the like.

Two or more kinds of the above-mentioned concomitant drugs may be used in combination at an appropriate ratio.

It is also possible to apply all the compounds disclosed in the present application, WO 2013/054822 A1, WO 2014/061676 A1, WO 2014/092100 A1, WO 2014/163161 A1 and WO 2014/163162 A1 to each of the above-mentioned diseases in combination with a biologic (e.g., antibody, vaccine preparation etc.), or as a combination therapy in combination with gene therapy method and the like.

Examples of the antibody and vaccine preparation include vaccine preparation to angiotensin II, vaccine preparation to CETP, CETP antibody, TNFα antibody and antibody to other cytokine, amyloid β vaccine preparation, type 1 diabetes vaccine (e.g., DIAPEP-277 manufactured by Peptor Ltd.), anti-HIV antibody, HIV vaccine preparation and the like, antibody or vaccine preparation to cytokine, renin-angiotensin enzyme and a product thereof, antibody or vaccine preparation to enzyme or protein involved in blood lipid metabolism, antibody or vaccine to enzyme or protein involved in blood coagulation or fibrinolytic system, antibody or vaccine preparation to protein involved in saccharometabolism or insulin resistance and the like.

In addition, a combined use with a biological preparation involved in a growth factor such as GH, IGF and the like is possible.

Examples of the gene therapy method include a treatment method using a gene relating to cytokine, renin-angiotensin enzyme and a product thereof, G protein, G protein conjugated receptor and its phosphorylation enzyme, a treatment method using a DNA decoy such as NFκB decoy and the like, a treatment method using an antisense, a treatment method using a gene relating to an enzyme or protein involved in blood lipid metabolism (e.g., gene relating to metabolism, excretion or absorption of cholesterol or triglyceride or HDL-cholesterol or blood phospholipid), a treatment method using a gene relating to an enzyme or protein involved in angiogenesis therapy targeting obstruction of peripheral vessel and the like (e.g., growth factors such as HGF, VEGF etc.), a treatment method using a gene relating to a protein involved in saccharometabolism or insulin resistance, an antisense to cytokine such as TNF and the like, and the like.

In addition, it is possible to use in combination with various organ regeneration methods such as heart regeneration, kidney regeneration, pancreas regeneration, blood vessel regeneration and the like or cell transplantation therapy utilizing bone marrow cell (myelomonocytic cell, myeloid stem cell) or an artificial organ utilizing tissue engineering (e.g., artificial blood vessel and cardiac muscle cell sheet).

The time of administration of all the compounds disclosed in the present application, WO 2013/054822 A1, WO 2014/061676 A1, WO 2014/092100 A1, WO 2014/163161 A1 and WO 2014/163162 A1 and that of the concomitant drug are not limited, and they may be administered simultaneously or in a staggered manner to the administration subject. Furthermore, all the compounds disclosed in the present application, WO 2013/054822 A1, WO 2014/061676 A1, WO 2014/092100 A1, WO 2014/163161 A1 and WO 2014/163162 A1 and the concomitant drug may be administered as two kinds of preparations containing each active ingredient, or a single preparation containing both active ingredients.

The dose of the concomitant drug can be appropriately determined based on the dose employed in clinical situations. The mixing ratio of all the compounds disclosed in the present application, WO 2013/054822 A1, WO 2014/061676 A1, WO 2014/092100 A1, WO 2014/163161 A1 and WO 2014/163162 A1 and a concomitant drug can be appropriately determined depending on the administration subject, administration route, target disease, symptom, combination and the like. When the subject of administration is human, for example, a concomitant drug can be used in 0.01-100 parts by weight relative to 1 part by weight of all the compounds disclosed in the present application, WO 2013/054822 A1, WO 2014/061676 A1, WO 2014/092100 A1, WO 2014/163161 A1 and WO 2014/163162 A1.

When the compounds of the invention are radiolabeled and/or are used as PET tracers, it is preferable that administration be done intravenously. Radiotracers labeled with positron emitting radionuclides are generally administered via intravenous injection within one hour of their synthesis due to the short half-life of the radionuclides involved, which is typically 20 and 110 minutes for $^{11}$C and $^{18}$F, respectively. When the radiolabeled CH24H inhibitors of the invention are administered to a human subject, the amount required for imaging will normally be determined by the prescribing physician with the dosage generally varying according to the quantity of emission from the radionuclide used. Those with ordinary skill in the art would appreciate that in most instances, an effective amount will be the amount of compound sufficient to produce emissions in the range of from about 1-5 mCi. The mass associated with a PET tracer is in the form of the natural isotope, for example, $^{12}$C for an $^{11}$C PET tracer and $^{19}$F for an $^{18}$F PET tracer, respectively. This mass comprises from about 0.1 g to about 50 g of a radiolabeled CH24H inhibitor in order to avoid significant inhibition of CH24H.

The following illustrative procedure may be utilized when performing PET imaging studies on patients in a clinical setting. The human subject is either unmedicated or premedicated with unlabeled CH24H inhibitor or other pharmacological intervention some time prior to the day of the experiment and is fasted for at least 12 hours allowing water intake ad libitum. A 20 G two inch venous catheter is inserted into the contralateral ulnar vein for radiotracer administration. Administration of the PET tracer is often timed to coincide with time of maximum ($T_{max}$) or minimum ($T_{min}$) of CH24H inhibitor (or other compound of intervention) concentration in the blood.

The human subject is positioned in the PET camera and a tracer dose of [$^{18}$F] Compound (I) is administered via i.v. catheter. Either arterial or venous blood samples are taken at appropriate time intervals throughout the PET scan in order to analyze and quantitate the fraction of unmetabolized [$^{18}$F](Compound (I)) in plasma. Images are acquired for up to 240 minutes. Within ten minutes of the injection of radiotracer and at the end of the imaging session, 1 ml blood samples are obtained for determining the plasma concentration of any unlabeled CH24H inhibitor (or other compound of intervention) which may have been administered before the PET tracer.

Tomographic images are obtained through image reconstruction. For determining the distribution of radiotracer, regions of interest (ROIs) are drawn on the reconstructed image including, but not limited to, the striatum, cerebellum and other specific brain regions or areas of the central nervous system. Radiotracer uptakes over time in these regions are used to generate time activity curves (TAC), including those obtained in the absence of any intervention or in the presence of CH24H inhibitors or other compound of intervention at the various dosing paradigms examined. Data are expressed as radioactivity per unit time per unit volume (μCi/cc/mCi injected dose). TAC data are processed with various methods well-known in the field to yield quantitative parameters, such as Binding Potential (BP), that are proportional to the density of unoccupied CH24H. Inhibition of CH24H is then calculated based on the change of BP in the presence of CH24H inhibitors at the various dosing paradigms as compared to the BP in the unmedicated state. Inhibition curves are generated by plotting the above data vs the dose (concentration) of CH24H inhibitors. The $ID_{50}$ values are obtained by curve fitting the dose-rate/inhibition curves with the following equation:

$$B = A_0 - A_0 * I/(ID_{50} + I) + NS$$

where B is the %-Dose/g of radiotracer in tissues for each dose of clinical candidate, $A_0$ is the specifically bound radiotracer in a tissue in the absence of CH24H inhibitors, I is the injected dose of inhibitor, $ID_{50}$ is the dose of compound which inhibits 50% of specific radiotracer binding to CH24H, and NS is the amount of non-specifically bond radiotracer.

The subject compounds are further useful in a method for the prevention, treatment, control, amelioration, or reduction of risk of the diseases, disorders and conditions noted herein. The dose of the active ingredient in the composition may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets being adhered to by the patient, concurrent medication, and other factors which those skilled in the art will recognize. Generally, dosage levels between 0.01 to 10 mg/kg of body weight daily are administered to the patient, e.g., humans and elderly humans. The dosage range will generally be about 0.5 mg to 1.0 g per patient pet day which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 mg of the active ingredient, such as, 1, 5, 10, 15, 20, 25, 50, 75, 100, 150, 200, 250, 300, 400, 500, 600, 750, 800, 900, and 1000 mg of the active ingredient for the symptomatic adjustment of the dosage to the patient to be treated. The compounds may be administered on a regimen of 1 to 4 times per day, preferably in a regimen of once or twice per day.

The compounds of the following examples had activity in inhibiting the human CH24H enzyme as described in the biological assay that follows, generally with an $IC_{50}$ of less than about 1 μM. Many of the compounds within the present invention had activity in inhibiting the human CH24H enzyme in the aforementioned assay, generally with an $IC_{50}$ of less than about 0.1 μM. Such a result is indicative of the intrinsic activity of the compounds in use as inhibitors of the CH24H enzyme. In general, one of ordinary skill in the art would appreciate that a substance is considered to effectively inhibit CH24H activity if it has an $IC_{50}$ of less than or about 1 μM, preferably less than or about 0.1 μM.

The CH24H $IC_{50}$ is a measure of the ability of the test compound to inhibit the action of the CH24H enzyme. To determine the selectivity of the test compounds for CH24H, inhibitory activities of the compound were determined for other CNS (central nerve system) related receptors and enzymes such as Adenosine A2B, Adrenergic β1, Adrenergic β2, Adrenergic β3, Angiotensin AT2, Bradykinin B1, Cannabinoid CB1, Carbonic Anhydrase II, Acetyl Cholinesterase, Cyclooxygenase (COX-1), Cyclooxygenase (COX-2), Dopamine D1, Dopamine D2L, Dopamine D3, Dopamine D4.2, GABA B1A, GABA B1B, Histamine H1, Histamine H2, Imidazoline I2 (Central), MAO A, MAO B, Muscarinic M1, Muscarinic M2, Muscarinic M3, Opiate κ (OP2, KOP), Opiate μ (OP3; MOP), Metalloproteinase, Phosphodiesterase 4 (PDE4), Phosphodiesterase 5 (PDE5), 5-HT2B, NK2, NK3, Dopamine transporter, Norepinephrine transporter, Serotonin transporter (SERT), Vasopressin V1A. The compounds of the following examples had activity in inhibiting CNS related receptors and enzymes as described in the selectivity assay that follows, generally with less than 50% inhibition at 10 μM. Such a result is indicative of the selectivity of the compounds in use as radiotracers for quantitative imaging of CH24H. In general, one of ordinary skill in the art would appreciate that a substance is considered to be effectively used for quantitative imaging of CH24H if it has an activity in inhibiting other CNS related receptors and enzymes with less than 50% at 10 μM.

The compounds of the present invention exhibit superior BBB (Brain-Blood Barrier) penetration. In addition, all the compounds disclosed in the present application, WO 2013/054822 A1, WO 2014/061676 A1, WO 2014/092100 A1, WO 2014/163161 A1 and WO 2014/163162 A1 exhibit preferably 1-10%, more preferably 2-4% at the % ID values which is calculated as total radioactivity in the brain (MBq)× 100/Injected radioactivity (MBq). The compounds of present invention exhibit high specific binding to striatum (caudate and putamen) which is CH24H rich region. In addition, the washout from nonspecific region (e.g., cerebellum) in brain shows faster than that from specific region (e.g., caudate, putamen), making them more attractive as potential PET radioligands. Since all the compounds disclosed in the present application, WO 2013/054822 A1, WO 2014/061676 A1, WO 2014/092100 A1, WO 2014/163161 A1 and WO 2014/163162 A1 show efficacy exhibition, they are useful as PET radioligands of CH24H.

EXAMPLES

The present invention will be explained in detail below with reference to the reference examples, embodiments, formulation examples and experimental examples. Since these are simply examples, the present invention will not be limited to these examples and the present invention can be modified in the range not deviating from the scope of the present invention.

In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, NH means use of aminopropylsilane-bound silica gel. In HPLC (high performance liquid chromatography), C18 means use of octadecyl-bound silica gel. The ratios of elution solvents are volume mixing ratios, unless otherwise specified.

The abbreviations used in the specification mean the following.
THF: tetrahydrofuran
DMF: N,N-dimethylformamide
DMA: N,N-dimethylacetamide
DMSO: dimethyl sulfoxide
$[M+H]^+$: molecular ion peak
M: mol concentration
IPE: diisopropyl ether
HATU: 2-(7-azabenzotriazol-1-yl)-1,1,3,3-tetramethyluronium hexafluorophosphate
HPLC: high-performance liquid chromatography
DIPEA: N,N-diisopropylethylamine
NMP: N-methyl-2-pyrrolidone $^1$H NMR (proton nuclear magnetic resonance spectrum) was measured by Fourier-transform type NMR. For the analysis, ACD/SpecManager (trade name) and the like were used. Peaks with very mild protons such as a hydroxy group, an amino group and the like are not described.

MS (mass spectrum) was measured by LC/MS (liquid chromatography mass spectrometer). As API (Atmospheric Pressure Ionization), ESI (Electro Spray Ionization) method, or APCI (Atmospheric Pressure Chemical Ionization) method was used. The data indicates those found. Generally, a molecular ion peak is observed. In the case of a compound having a tert-butoxycarbonyl group (-Boc), a peak after elimination of a tert-butoxycarbonyl group or tert-butyl group may be observed as a fragment ion. In the case of a compound having a hydroxy group (—OH), a peak after elimination of $H_2O$ may be observed as a fragment ion. In the case of a salt, a molecular ion peak or fragment ion peak of free form is generally observed.

The elemental analysis value (Anal.) shows Calculated value (Calcd) and Found value (Found).

REFERENCE EXAMPLES

Reference Example 1

N-cyclopropyl-1-(4-(4-fluorophenyl)pyrimidin-5-yl)-N-methylpiperidine-4-carboxamide A) ethyl 1-(2-(4-fluorophenyl)-2-oxoethyl)piperidine-4-carboxylate To a mixture of ethyl piperidine-4-carboxylate (8.0 g) and potassium carbonate (9.6 g) in acetonitrile (90 mL) was added dropwise 2-chloro-1-(4-fluorophenyl)ethanone (8.0 g) in acetonitrile (60 mL) at room temperature. The mixture was stirred at the same temperature overnight. The reaction mixture was concentrated in vacuo, diluted with water and extracted with ethyl acetate. The extract was washed with brine, dried over sodium sulfate, filtered and concentrated in vacuo to give the title compound (13 g).
MS (API+), found: 294.1.

B) ethyl 1-(4-(4-fluorophenyl)pyrimidin-5-yl)piperidine-4-carboxylate

A mixture of ethyl 1-(2-(4-fluorophenyl)-2-oxoethyl)piperidine-4-carboxylate (13 g) and DMF-DMA (82 mL) was refluxed overnight. The mixture was concentrated in vacuo. The mixture was dissolved into n-butanol (40 mL) and DIPEA (40 mL). Formamidine acetate (16 g) was added to the mixture and the mixture was stirred at 100° C. overnight. The mixture was diluted with water and extracted with ethyl acetate. The extract was washed with water and brine, dried over magnesium sulfate, filtered and concentrated in vacuo. The residue was purified by silica gel column chromatography (ethyl acetate/hexane) to give the title compound (9.9 g).
MS (API+), found: 330.1.

C) 1-(4-(4-fluorophenyl)pyrimidin-5-yl)piperidine-4-carboxylic acid

To a mixture of ethyl 1-(4-(4-fluorophenyl)pyrimidin-5-yl)piperidine-4-carboxylate (9.9 g) in THF (80 mL) and methanol (20 mL) was added 2M aqueous sodium hydroxide solution (30 mL) at room temperature. After being stirred at the same temperature for 1.5 hr, the mixture was concentrated in vacuo, diluted with water and neutralized with 2M hydrochloric acid. The resulting solid was collected and dried in vacuo to give the title compound (8.3 g).
MS (API+), found: 302.1.

D) N-cyclopropyl-1-(4-(4-fluorophenyl)pyrimidin-5-yl)-N-methylpiperidine-4-carboxamide A mixture of 1-(4-(4-fluorophenyl)pyrimidin-5-yl)piperidine-4-carboxylic acid (0.10 g), N-methylcyclopropanamine (28 mg), HATU (0.15 g), DIPEA (0.15 mL) and DMF (2.0 mL) was stirred at room temperature for 4 hr. To the mixture was added water, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and the obtained solid was crystallized from ethyl acetate/heptane to give the title compound (94 mg).

$^1$H NMR (300 MHz, CDCl$_3$) δ 0.70-0.81 (2H, m), 0.85-0.96 (2H, m), 1.65-1.77 (2H, m), 1.82-1.99 (2H, m), 2.62-2.75 (3H, m), 2.93 (3H, s), 3.02-3.17 (1H, m), 3.24-3.37 (2H, m), 7.13-7.22 (2H, m), 8.11-8.20 (2H, m), 8.42 (1H, s), 8.90 (1H, s).

Reference Example 2

(3-fluoroazetidin-1-yl) (1-(4-(4-fluorophenyl)pyrimidin-5-yl)piperidin-4-yl)methanone A mixture of 1-(4-(4-fluorophenyl)pyrimidin-5-yl)piperidine-4-carboxylic acid (0.10 g), 3-fluoroazetidine hydrochloride (0.056 g), HATU (0.16 g), DIPEA (0.23 mL) and DMF (2.0 mL) was stirred at room temperature for 18 hr. The mixture was diluted with ethyl acetate and water, and extracted with ethyl acetate. The organic layer was washed with water and brine, dried over anhydrous sodium sulfate, and the solvent was evaporated under reduced pressure. The residue was purified by silica gel column chromatography (NH, ethyl acetate/hexane), and triturated with diethyl ether to give the title compound (0.11 g).

$^1$H NMR (300 MHz, CDCl$_3$) δ 1.62-1.94 (4H, m), 2.18-2.31 (1H, m), 2.59-2.73 (2H, m), 3.21-3.34 (2H, m), 4.03-4.49 (4H, m), 5.18-5.46 (1H, m), 7.12-7.21 (2H, m), 8.09-8.17 (2H, m), 8.41 (1H, s), 8.90 (1H, s).

Reference Example 3

1-(4-(4-chloro-1H-pyrazol-1-yl)pyridin-3-yl)-N-methyl-N-(tetrahydro-2H-pyran-4-yl)piperidine-4-carboxamide A) 4-(4-chloro-1H-pyrazol-1-yl)-3-fluoropyridine A mixture of p-toluenesulfonic acid monohydrate (0.58 g), 4-chloro-3-fluoropyridine (2.0 g), 4-chloro-1H-pyrazole (1.7 g) and 2-propanol (10 mL) was irradiated with microwave at 130° C. for 2 hr. The mixture was allowed to be cooled to room temperature, saturated aqueous sodium bicarbonate solution was added thereto, and the mixture was extracted with ethyl acetate. The organic layer was washed with saturated brine, and dried over anhydrous sodium sulfate, and the solvent was evaporated under reduced pressure. The residue was purified by silica gel column chromatography (ethyl acetate/hexane) to give the title compound (2.2 g).

MS (API+), found: 198.2, 200.0.

B) ethyl 1-(4-(4-chloro-1H-pyrazol-1-yl)pyridin-3-yl)piperidine-4-carboxylate

A mixture of 4-(4-chloro-1H-pyrazol-1-yl)-3-fluoropyridine (3.4 g), ethyl piperidine-4-carboxylate (13 mL), potassium carbonate (7.1 g) and NMP (15 mL) was stirred at 180° C. for 4 hr. To the mixture was added water at 0° C., and the mixture was extracted with ethyl acetate. The organic layer was washed with water and saturated brine, and dried over anhydrous sodium sulfate, and the solvent was evaporated under reduced pressure. The residue was purified by silica gel column chromatography (ethyl acetate/hexane) to give the title compound (5.3 g).

$^1$H NMR (300 MHz, DMSO-d$_6$) δ 1.16-1.23 (3H, m), 1.56-1.74 (2H, m), 1.80-1.93 (2H, m), 2.37-2.46 (1H, m), 2.66-2.79 (2H, m), 2.89 (2H, dt, J=12.1, 3.2 Hz), 4.09 (2H, q, J=7.2 Hz), 7.52 (1H, d, J=4.9 Hz), 7.96 (1H, s), 8.36 (1H, d, J=4.9 Hz), 8.48 (1H, s), 8.77 (1H, s).

C) 1-(4-(4-chloro-1H-pyrazol-1-yl)pyridin-3-yl)piperidine-4-carboxylic acid

Ethyl 1-(4-(4-chloro-1H-pyrazol-1-yl)pyridin-3-yl)piperidine-4-carboxylate (5.3 g) was dissolved in THF (55 mL) and ethanol (20 mL), to the mixture was added 2M aqueous sodium hydroxide solution (12 mL), and the mixture was stirred overnight at room temperature. The mixture was neutralized with 1M hydrochloric acid (24 mL), and the precipitated solid was collected by filtration to give the title compound (4.0 g).

$^1$H NMR (300 MHz, DMSO-d$_6$) δ 1.55-1.71 (2H, m), 1.84 (2H, dd, J=13.3, 3.0 Hz), 2.25-2.39 (1H, m), 2.64-2.76 (2H, m), 2.89 (2H, dt, J=12.0, 3.3 Hz), 7.52 (1H, d, J=5.3 Hz), 7.96 (1H, s), 8.36 (1H, d, J=5.3 Hz), 8.48 (1H, s), 8.77 (1H, s), 12.27 (1H, brs).

D) 1-(4-(4-chloro-1H-pyrazol-1-yl)pyridin-3-yl)-N-methyl-N-(tetrahydro-2H-pyran-4-yl)piperidine-4-carboxamide A mixture of 1-(4-(4-chloro-1H-pyrazol-1-yl)pyridin-3-yl)piperidine-4-carboxylic acid (0.50 g), N-methyltetrahydro-2H-pyran-4-amine (0.16 g), HATU (0.81 g), triethylamine (0.91 mL) and DMF (8.2 mL) was stirred at room temperature for 3 hr. To the mixture was added water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (NH, ethyl acetate/hexane), and the obtained solid was crystallized from ethyl acetate/hexane to give the title compound (0.43 g).

$^1$H NMR (300 MHz, CDCl$_3$) δ 1.45-1.65 (2H, m), 1.65-2.11 (6H, m), 2.61 (1H, brs), 2.71-2.97 (5H, m), 3.13 (2H, d, J=11.7 Hz), 3.37-3.59 (2H, m), 3.94-4.16 (2H, m), 4.66-4.84 (1H, m), 7.59 (1H, s), 7.66 (1H, s), 8.40 (1H, s), 8.46 (1H, s), 8.59 (1H, s).

Reference Example 4

(3-fluoroazetidin-1-yl) (1-(4-(4-methyl-1H-pyrazol-1-yl)pyridin-3-yl)piperidin-4-yl)methanone A) 3-fluoro-4-(4-methyl-1H-pyrazol-1-yl)pyridine A mixture of p-toluenesulfonic acid monohydrate (0.83 g), 4-chloro-3-fluoropyridine (2.9 g), 4-methyl-1H-pyrazole (1.9 mL) and 2-propanol (14 mL) was irradiated with microwave at 130° C. for 2 hr. To the mixture was added saturated aqueous sodium bicarbonate solution, and the mixture was extracted with ethyl acetate. The organic layer was washed with water and saturated brine, and dried over anhydrous sodium sulfate, and the solvent was evaporated under reduced pressure. The residue was purified by silica gel column chromatography (ethyl acetate/hexane) to give the title compound (3.3 g).

$^1$H NMR (300 MHz, DMSO-d$_6$) δ 2.12 (3H, s), 7.76 (1H, s), 7.93 (1H, dd, J=7.0, 5.5 Hz), 8.18 (1H, dd, J=1.9, 0.8 Hz), 8.49 (1H, d, J=5.3 Hz), 8.74 (1H, d, J=4.2 Hz).

B) ethyl 1-(4-(4-methyl-1H-pyrazol-1-yl)pyridin-3-yl)piperidine-4-carboxylate

A mixture of 3-fluoro-4-(4-methyl-1H-pyrazol-1-yl)pyridine (2.5 g), ethyl piperidine-4-carboxylate (4.3 mL), potassium carbonate (5.8 g) and NMP (12 mL) was stirred at 180° C. for 7 hr. To the mixture was added ethyl piperidine-4-carboxylate (2.0 mL) at room temperature, and the mixture was stirred at 180° C. for 2 hr, and then overnight at room temperature. To the mixture was added water at 0° C., and the mixture was extracted with ethyl acetate. The organic layer was washed with water and saturated brine, and dried over anhydrous sodium sulfate, and the solvent was evaporated under reduced pressure. The residue was purified by silica gel column chromatography (ethyl acetate/hexane) to give the title compound (2.8 g).

MS (API+): [M+H]+ 315.2.

C) 1-(4-(4-methyl-1H-pyrazol-1-yl)pyridin-3-yl)piperidine-4-carboxylic acid

To a solution of ethyl 1-(4-(4-methyl-1H-pyrazol-1-yl)pyridin-3-yl)piperidine-4-carboxylate (1.2 g), THF (15 mL) and ethanol (5.0 mL) was added 2M aqueous sodium hydroxide solution (3.0 mL), and the mixture was stirred overnight at room temperature. The mixture was cooled to 0° C., and neutralized with 1M hydrochloric acid (6.0 mL). The precipitated solid was collected by filtration, and washed with water to give the title compound (0.84 g).

MS (API+): [M+H]+ 287.2.

D) (3-fluoroazetidin-1-yl) (1-(4-(4-methyl-1H-pyrazol-1-yl)pyridin-3-yl)piperidin-4-yl)methanone A mixture of 1-(4-(4-methyl-1H-pyrazol-1-yl)pyridin-3-yl)piperidine-4-carboxylic acid (60 mg), 3-fluoroazetidine hydrochloride (28 mg), HATU (96 mg), DIPEA (0.091 mL) and DMF (2.0 mL) was stirred at room temperature for 4 hr. To the mixture was added water, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and the obtained solid was crystallized from ethyl acetate/heptane to give the title compound (68 mg).

$^1$H NMR (300 MHz, CDCl$_3$) δ 1.67-1.99 (4H, m), 2.17 (3H, s), 2.20-2.33 (1H, m), 2.64-2.78 (2H, m), 3.07-3.19 (2H, m), 4.04-4.52 (4H, m), 5.19-5.48 (1H, m), 7.54 (1H, s), 7.60 (1H, d, J=5.3 Hz), 8.32-8.36 (2H, m), 8.39 (1H, s).

Reference Example 5

(1-(4-(4-chloro-1H-pyrazol-1-yl)pyridin-3-yl)piperidin-4-yl) (3-fluoroazetidin-1-yl)methanone A mixture of 1-(4-(4-chloro-1H-pyrazol-1-yl)pyridin-3-yl)piperidine-4-carboxylic acid (0.060 g), 3-fluoroazetidine hydrochloride (0.026 g), HATU (0.089 g), DIPEA (0.085 mL) and DMF (2.0 mL) was stirred at room temperature for 4 hr. The mixture was diluted with ethyl acetate and water, and extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and crystallized from ethyl acetate/heptane to give the title compound (0.062 g).

$^1$H NMR (300 MHz, CDCl$_3$) δ 1.69-2.01 (4H, m), 2.21-2.36 (1H, m), 2.68-2.81 (2H, m), 3.05-3.18 (2H, m), 4.03-4.53 (4H, m), 5.19-5.48 (1H, m), 7.59 (1H, d, J=5.3 Hz), 7.66 (1H, s), 8.39 (1H, d, J=5.3 Hz), 8.44 (1H, s), 8.56 (1H, s).

Reference Example 6

((3S)-3-fluoropyrrolidin-1-yl) (1-(4-(4-methyl-1H-pyrazol-1-yl)pyridin-3-yl)piperidin-4-yl)methanone A mixture of 1-(4-(4-methyl-1H-pyrazol-1-yl)pyridin-3-yl)piperidine-4-carboxylic acid (60 mg), (S)-3-fluoropyrrolidine hydrochloride (32 mg), HATU (96 mg), DIPEA (0.091 mL) and DMF (2.0 mL) was stirred at room temperature for 4 hr. To the mixture was added water, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and the obtained solid was crystallized from ethyl acetate/heptane to give the title compound (68 mg).

$^1$H NMR (300 MHz, CDCl$_3$) δ 1.68-2.10 (5H, m), 2.17 (3H, s), 2.20-2.56 (2H, m), 2.66-2.79 (2H, m), 3.09-3.20 (2H, m), 3.45-3.99 (4H, m), 5.14-5.44 (1H, m), 7.54 (1H, s), 7.61 (1H, d, J=5.3 Hz), 8.32-8.37 (2H, m), 8.40 (1H, s).

Reference Example 7

((3R)-3-fluoropyrrolidin-1-yl) (1-(4-(4-methyl-1H-pyrazol-1-yl)pyridin-3-yl)piperidin-4-yl)methanone A mixture of 1-(4-(4-methyl-1H-pyrazol-1-yl)pyridin-3-yl)piperidine-4-carboxylic acid (60 mg), (R)-3-fluoropyrrolidine hydrochloride (32 mg), HATU (96 mg), DIPEA (0.091 mL) and DMF (2.0 mL) was stirred at room temperature for 4 hr. To the mixture was added water, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and the obtained solid was crystallized from ethyl acetate/heptane to give the title compound (64 mg).

$^1$H NMR (300 MHz, CDCl$_3$) δ 1.70-2.15 (5H, m), 2.17 (3H, s), 2.21-2.56 (2H, m), 2.65-2.80 (2H, m), 3.08-3.20 (2H, m), 3.45-4.00 (4H, m), 5.15-5.43 (1H, m), 7.54 (1H, s), 7.61 (1H, d, J=5.3 Hz), 8.33-8.37 (2H, m), 8.40 (1H, s).

Reference Example 8

(1-(4-(4-chloro-1H-pyrazol-1-yl)pyridin-3-yl)piperidin-4-yl) ((3S)-3-fluoropyrrolidin-1-yl)methanone A mixture of 1-(4-(4-chloro-1H-pyrazol-1-yl)pyridin-3-yl)piperidine-4-carboxylic acid (0.060 g), (S)-3-fluoropyrrolidine hydrochloride (0.030 g), HATU (0.089 g), DIPEA (0.085 mL) and DMF (2.0 mL) was stirred at room temperature for 4 hr. The mixture was diluted with ethyl acetate and water, and extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and crystallized from ethyl acetate/heptane to give the title compound (0.064 g).

$^1$H NMR (300 MHz, CDCl$_3$) δ 1.72-2.58 (7H, m), 2.69-2.84 (2H, m), 3.08-3.20 (2H, m), 3.46-4.01 (4H, m), 5.13-

5.44 (1H, m), 7.60 (1H, d, J=5.3 Hz), 7.66 (1H, s), 8.39 (1H, d, J=5.3 Hz), 8.45 (1H, s), 8.59 (1H, s).

Reference Example 9

(1-(4-(4-chloro-1H-pyrazol-1-yl)pyridin-3-yl)piperidin-4-yl) ((3R)-3-fluoropyrrolidin-1-yl)methanone A mixture of 1-(4-(4-chloro-1H-pyrazol-1-yl)pyridin-3-yl)piperidine-4-carboxylic acid (60 mg), (R)-3-fluoropyrrolidine hydrochloride (30 mg), HATU (89 mg), DIPEA (0.085 mL) and DMF (2.0 mL) was stirred at room temperature for 2 hr. To the mixture was added water, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and the obtained solid was crystallized from ethyl acetate/heptane to give the title compound (63 mg).
$^1$H NMR (300 MHz, CDCl$_3$) δ 1.74-2.59 (7H, m), 2.69-2.84 (2H, m), 3.07-3.20 (2H, m), 3.45-3.99 (4H, m), 5.15-5.44 (1H, m), 7.60 (1H, d, J=5.3 Hz), 7.66 (1H, s), 8.39 (1H, d, J=5.3 Hz), 8.46 (1H, s), 8.59 (1H, s).

Reference Example 10

(1-(4-(4-fluorophenyl)pyrimidin-5-yl)piperidin-4-yl) ((3S)-3-fluoropyrrolidin-1-yl)methanone A mixture of 1-(4-(4-fluorophenyl)pyrimidin-5-yl)piperidine-4-carboxylic acid (0.060 g), (S)-3-fluoropyrrolidine hydrochloride (0.030 g), HATU (0.091 g), DIPEA (0.087 mL) and DMF (2.0 mL) was stirred at room temperature for 4 hr. The mixture was diluted with ethyl acetate and water, and extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and crystallized from ethyl acetate/heptane to give the title compound (0.059 g).
$^1$H NMR (300 MHz, CDCl$_3$) δ 1.66-2.54 (7H, m), 2.61-2.74 (2H, m), 3.25-3.36 (2H, m), 3.45-3.98 (4H, m), 5.14-5.41 (1H, m), 7.12-7.22 (2H, m), 8.11-8.18 (2H, m), 8.42 (1H, s), 8.90 (1H, s).

Reference Example 11

(1-(4-(4-fluorophenyl)pyrimidin-5-yl)piperidin-4-yl) ((3R)-3-fluoropyrrolidin-1-yl)methanone A mixture of 1-(4-(4-fluorophenyl)pyrimidin-5-yl)piperidine-4-carboxylic acid (60 mg), (R)-3-fluoropyrrolidine hydrochloride (30 mg), HATU (91 mg), DIPEA (0.087 mL) and DMF (2.0 mL) was stirred at room temperature for 4 hr. To the mixture was added water, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and the obtained solid was crystallized from ethyl acetate/heptane to give the title compound (60 mg).
$^1$H NMR (300 MHz, CDCl$_3$) δ 1.64-2.53 (7H, m), 2.61-2.75 (2H, m), 3.24-3.37 (2H, m), 3.46-3.98 (4H, m), 5.13-5.43 (1H, m), 7.12-7.21 (2H, m), 8.10-8.18 (2H, m), 8.42 (1H, s), 8.90 (1H, s).

Reference Example 12

1-(4-(4-fluorophenyl)pyrimidin-5-yl)-N-methyl-N-(tetrahydro-2H-pyran-4-yl)piperidine-4-carboxamide A mixture of 1-(4-(4-fluorophenyl)pyrimidin-5-yl)piperidine-4-carboxylic acid (60 mg), N-methyl-N-(tetrahydro-2H-pyran-4-yl)amine (28 mg), HATU (91 mg), DIPEA (0.087 mL) and DMF (2.0 mL) was stirred at room temperature for 4 hr. To the mixture was added water, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and the obtained solid was crystallized from ethyl acetate/heptane to give the title compound (68 mg).
$^1$H NMR (300 MHz, CDCl$_3$) δ 1.46-2.06 (8H, m), 2.48-2.77 (3H, m), 2.81-2.95 (3H, m), 3.21-3.57 (4H, m), 3.96-4.13 (2H, m), 4.62-4.84 (1H, m), 7.12-7.21 (2H, m), 8.10-8.19 (2H, m), 8.42 (1H, s), 8.90 (1H, s).

Reference Example 13

1-(4-(4-chloro-1H-pyrazol-1-yl)pyridin-3-yl)-N-methyl-N-((3S)-tetrahydrofuran-3-yl) piperidine-4-carboxamide A) 1-(4-(4-chloro-1H-pyrazol-1-yl)pyridin-3-yl)-N-((3S)-tetrahydrofuran-3-yl) piperidine-4-carboxamide A mixture of 1-(4-(4-chloro-1H-pyrazol-1-yl)pyridin-3-yl)piperidine-4-carboxylic acid (0.50 g), (S)-tetrahydrofuran-3-amine hydrochloride (0.20 g), HATU (0.81 g), triethylamine (0.91 mL) and DMF (5.4 mL) was stirred at room temperature for 3 hr. To the mixture was added water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (NH, ethyl acetate/hexane), and the obtained solid was crystallized from ethyl acetate/hexane to give the title compound (0.51 g).
$^1$H NMR (300 MHz, CDCl$_3$) δ 1.72-1.96 (5H, m), 2.10-2.37 (2H, m), 2.73 (2H, td, J=10.8, 4.2 Hz), 3.04-3.18 (2H, m), 3.67 (1H, dd, J=9.5, 2.3 Hz), 3.74-3.87 (2H, m), 3.89-4.00 (1H, m), 4.49-4.62 (1H, m), 5.71 (1H, d, J=7.2 Hz), 7.59 (1H, d, J=5.3 Hz), 7.66 (1H, d, J=0.8 Hz), 8.39 (1H, d, J=5.3 Hz), 8.44 (1H, s), 8.54 (1H, d, J=0.8 Hz).

B) 1-(4-(4-chloro-1H-pyrazol-1-yl)pyridin-3-yl)-N-methyl-N-((3S)-tetrahydrofuran-3-yl)piperidine-4-carboxamide To a mixture of 1-(4-(4-chloro-1H-pyrazol-1-yl)pyridin-3-yl)-N-((3S)-tetrahydrofuran-3-yl)piperidine-4-carboxamide (0.12 g) and DMF (2.0 mL) was added sodium hydride (60%, 19 mg) under ice-cooling, and the mixture was stirred for 30 min. To the mixture was added methyl iodide (0.030 mL), and the mixture was stirred for 1 hr under ice-cooling.

To the mixture were added saturated aqueous ammonium chloride solution, ethyl acetate and pyridine, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane) to give the title compound (0.094 g).

$^1$H NMR (300 MHz, CDCl$_3$) δ 1.71-2.03 (5H, m), 2.19-2.35 (1H, m), 2.53-3.02 (6H, m), 3.07-3.19 (2H, m), 3.60-3.85 (3H, m), 4.01-4.12 (1H, m), 5.30-5.44 (1H, m), 7.60 (1H, d, J=5.3 Hz), 7.66 (1H, s), 8.39 (1H, d, J=4.9 Hz), 8.45 (1H, s), 8.58 (1H, S).

Reference Example 14

1-(4-(4-chloro-1H-pyrazol-1-yl)pyridin-3-yl)-N-methyl-N-((3R)-tetrahydrofuran-3-yl)piperidine-4-carboxamide A) 1-(4-(4-chloro-1H-pyrazol-1-yl)pyridin-3-yl)-N-((3R)-tetrahydrofuran-3-yl)piperidine-4-carboxamide A mixture of 1-(4-(4-chloro-1H-pyrazol-1-yl)pyridin-3-yl)piperidine-4-carboxylic acid (0.50 g), (R)-tetrahydrofuran-3-amine hydrochloride (0.20 g), HATU (0.81 g), triethylamine (0.91 mL) and DMF (5.4 mL) was stirred at room temperature for 3 hr. To the mixture was added water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (NH, ethyl acetate/hexane), and the obtained solid was crystallized from ethyl acetate/hexane to give the title compound (0.50 g).

$^1$H NMR (300 MHz, CDCl$_3$) δ 1.69-1.97 (5H, m), 2.10-2.37 (2H, m), 2.73 (2H, td, J=10.8, 4.2 Hz), 3.05-3.17 (2H, m), 3.67 (1H, dd, J=9.5, 2.3 Hz), 3.73-3.87 (2H, m), 3.89-4.01 (1H, m), 4.55 (1H, ddt, J=7.6, 5.1, 2.4 Hz), 5.69 (1H, d, J=7.2 Hz), 7.59 (1H, d, J=5.3 Hz), 7.66 (1H, s), 8.39 (1H, d, J=5.3 Hz), 8.44 (1H, s), 8.54 (1H, d, J=0.8 Hz).

B) 1-(4-(4-chloro-1H-pyrazol-1-yl)pyridin-3-yl)-N-methyl-N-((3R)-tetrahydrofuran-3-yl)piperidine-4-carboxamide To a mixture of 1-(4-(4-chloro-1H-pyrazol-1-yl)pyridin-3-yl)-N-((3R)-tetrahydrofuran-3-yl)piperidine-4-carboxamide (0.12 g) and DMF (2.0 mL) was added sodium hydride (60%, 19 mg) under ice-cooling, and the mixture was stirred for 30 min. To the mixture was added methyl iodide (0.030 mL), and the mixture was stirred for 1 hr under ice-cooling. To the mixture were added saturated aqueous ammonium chloride solution, ethyl acetate and pyridine, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane) to give the title compound (0.092 g).

$^1$H NMR (300 MHz, CDCl$_3$) δ 1.70-2.03 (5H, m), 2.18-2.35 (1H, m), 2.53-3.04 (6H, m), 3.08-3.20 (2H, m), 3.60-3.85 (3H, m), 4.01-4.12 (1H, m), 5.31-5.43 (1H, m), 7.60 (1H, d, J=5.3 Hz), 7.66 (1H, s), 8.39 (1H, d, J=5.3 Hz), 8.45 (1H, s), 8.58 (1H, s).

Reference Example 15

1-(4-(4-fluorophenyl)pyrimidin-5-yl)-N-methyl-N-((3S)-tetrahydrofuran-3-yl) piperidine-4-carboxamide A) 1-(4-(4-fluorophenyl)pyrimidin-5-yl)-N-((3S)-tetrahydrofuran-3-yl) piperidine-4-carboxamide A mixture of 1-(4-(4-fluorophenyl)pyrimidin-5-yl)piperidine-4-carboxylic acid (0.30 g), (S)-tetrahydrofuran-3-amine hydrochloride (0.15 g), HATU (0.45 g), DIPEA (0.43 mL) and DMF (5.0 mL) was stirred at room temperature for 4 hr. To the mixture was added water, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and the Obtained solid was crystallized from ethyl acetate/heptane to give the title compound (0.32 g).

$^1$H NMR (300 MHz, CDCl$_3$) δ 1.70-1.87 (5H, m), 2.06-2.19 (1H, m), 2.22-2.36 (1H, m), 2.59-2.71 (2H, m), 3.21-3.34 (2H, m), 3.66 (1H, dd, J=9.4, 2.3 Hz), 3.74-3.85 (2H, m), 3.89-3.99 (1H, m), 4.47-4.60 (1H, m), 5.63 (1H, d, J=6.4 Hz), 7.12-7.21 (2H, m), 8.08-8.16 (2H, m), 8.41 (1H, s), 8.90 (1H, s).

B) 1-(4-(4-fluorophenyl)pyrimidin-5-yl)-N-methyl-N-((3S)-tetrahydrofuran-3-yl) piperidine-4-carboxamide To a mixture of 1-(4-(4-fluorophenyl)pyrimidin-5-yl)-N-((3S)-tetrahydrofuran-3-yl)piperidine-4-carboxamide (0.12 g) and DMF (2.0 mL) was added sodium hydride (60%, 19 mg) under ice-cooling, and the mixture was stirred for 30 min. To the mixture was added methyl iodide (0.034 mL), and the mixture was stirred for 2.5 hr under ice-cooling. To the mixture were added saturated aqueous ammonium chloride solution, ethyl acetate and pyridine, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and crystallized from ethyl acetate/heptane to give the title compound (0.091 g).

$^1$H NMR (300 MHz, CDCl$_3$) δ 1.66-2.03 (5H, m), 2.17-2.35 (1H, m), 2.46-2.75 (3H, m), 2.83-3.01 (3H, m), 3.23-3.35 (2H, m), 3.60-3.82 (3H, m), 4.00-4.12 (1H, m), 5.27-5.42 (1H, m), 7.12-7.22 (2H, m), 8.09-8.19 (2H, m), 8.42 (1H, s), 8.90 (1H, s).

Reference Example 16

1-(4-(4-fluorophenyl)pyrimidin-5-yl)-N-methyl-N-((3R)-tetrahydrofuran-3-yl)piperidine-4-carboxamide A) 1-(4-(4-fluorophenyl)pyrimidin-5-yl)-N-((3R)-tetrahydrofuran-3-yl)piperidine-4-carboxamide A mixture of 1-(4-(4-fluorophenyl)pyrimidin-5-yl)piperidine-4-carboxylic acid (0.30 g), (R)-tetrahydrofuran-3-amine hydrochloride (0.15 g), HATU (0.45 g), DIPEA (0.43 mL) and DMF (5.0 mL) was stirred at room temperature for 4 hr. To the mixture was added water, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and the obtained solid was crystallized from ethyl acetate/heptane to give the title compound (0.34 g).

$^1$H NMR (300 MHz, CDCl$_3$) δ 1.71-1.86 (5H, m), 2.04-2.18 (1H, m), 2.22-2.36 (1H, m), 2.59-2.71 (2H, m), 3.22-3.32 (2H, m), 3.62-3.69 (1H, m), 3.74-3.85 (2H, m), 3.89-3.99 (1H, m), 4.47-4.60 (1H, m), 5.63 (1H, d, J=7.5 Hz), 7.12-7.22 (2H, m), 8.06-8.17 (2H, m), 8.41 (1H, s), 8.90 (1H, s).

B) 1-(4-(4-fluorophenyl)pyrimidin-5-yl)-N-methyl-N-((3R)-tetrahydrofuran-3-yl)piperidine-4-carboxamide To a mixture of 1-(4-(4-fluorophenyl)pyrimidin-5-yl)-N-((3R)-tetrahydrofuran-3-yl)piperidine-4-carboxamide (0.12 g) and DMF (2.0 mL) was added sodium hydride (60%, 19 mg) under ice-cooling, and the mixture was stirred for 30 min. To the mixture was added methyl iodide (0.034 mL), and the mixture was stirred for 2.5 hr under ice-cooling. To the mixture were added saturated aqueous ammonium chloride solution, ethyl acetate and pyridine, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and crystallized from ethyl acetate/heptane to give the title compound (0.087 g).

$^1$H NMR (300 MHz, CDCl$_3$) δ 1.65-2.02 (5H, m), 2.16-2.36 (1H, m), 2.48-2.77 (3H, m), 2.84-3.02 (3H, m), 3.24-3.35 (2H, m), 3.60-3.81 (3H, m), 4.00-4.11 (1H, m), 5.29-5.41 (1H, m), 7.12-7.21 (2H, m), 8.10-8.19 (2H, m), 8.42 (1H, s), 8.90 (1H, s).

Reference Example 17

N-(2-fluoroethyl)-1-(4-(4-methyl-1H-pyrazol-1-yl)pyridin-3-yl)-N-(tetrahydro-2H-pyran-4-yl)piperidine-4-carboxamide A) 1-(4-(4-methyl-1H-pyrazol-1-yl)pyridin-3-yl)-N-(tetrahydro-2H-pyran-4-yl)piperidine-4-carboxamide A mixture of 1-(4-(4-methyl-1H-pyrazol-1-yl)pyridin-3-yl)piperidine-4-carboxylic acid (1.0 g), tetrahydro-2H-pyran-4-amine (0.36 mL), HATU (1.7 g), triethylamine (1.9 mL) and DMF (12 mL) was stirred at room temperature for 3 hr. To the mixture was added water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (NH, ethyl acetate/hexane), and the obtained solid was crystallized from ethyl acetate/hexane to give the title compound (0.78 g).

$^1$H NMR (300 MHz, CDCl$_3$) δ 1.35-1.54 (2H, m), 1.78-1.98 (6H, m), 2.06-2.21 (4H, m), 2.70 (2H, dt, J=11.7, 7.2 Hz), 3.12 (2H, d, J=12.1 Hz), 3.48 (2H, td, J=11.7, 2.3 Hz), 3.88-4.09 (3H, m), 5.37 (1H, d, J=7.6 Hz), 7.54 (1H, s), 7.60 (1H, d, J=5.3 Hz), 8.30-8.36 (2H, m), 8.39 (1H, s).

B) N-(2-fluoroethyl)-1-(4-(4-methyl-1H-pyrazol-1-yl)pyridin-3-yl)-N-(tetrahydro-2H-pyran-4-yl)piperidine-4-carboxamide To a mixture of 1-(4-(4-methyl-1H-pyrazol-1-yl)pyridin-3-yl)-N-(tetrahydro-2H-pyran-4-yl)piperidine-4-carboxamide (0.12 g) and DMF (2.0 mL) was added sodium hydride (60%, 19 mg), and the mixture was stirred for 30 min. To the mixture was added a solution of 2-fluoroethyl 4-methylbenzenesulfonate (0.11 g) in DMF (1.0 mL), and the mixture was stirred at room temperature for 16 hr. To the mixture was added saturated aqueous ammonium chloride solution, and the mixture was extracted with ethyl acetate. The organic layer was washed with water and saturated brine, and dried over anhydrous sodium sulfate, and the solvent was evaporated under reduced pressure. The residue was purified by silica gel column chromatography (ethyl acetate/hexane) to give the title compound (3.4 mg).

$^1$H NMR (300 MHz, CDCl$_3$) δ 1.61-2.04 (8H, m), 2.17 (3H, s), 2.56-2.85 (3H, m), 3.06-3.22 (2H, m), 3.38-3.89 (5H, m), 3.97-4.15 (2H, m), 4.35-4.74 (2H, m), 7.54 (1H, s), 7.61 (1H, d, J=5.3 Hz), 8.31-8.45 (3H, m).

Reference Example 18

N-(2-fluoroethyl)-1-(4-(4-methyl-1H-pyrazol-1-yl)pyridin-3-yl)-N-((3S)-tetrahydrofuran-3-yl)piperidine-4-carboxamide A) 1-(4-(4-methyl-1H-pyrazol-1-yl)pyridin-3-yl)-N-((3S)-tetrahydrofuran-3-yl) piperidine-4-carboxamide A mixture of 1-(4-(4-methyl-1H-pyrazol-1-yl)pyridin-3-yl)piperidine-4-carboxylic acid (1.0 g), (S)-tetrahydrofuran-3-amine hydrochloride (0.43 g), HATU (1.7 g), triethylamine (1.9 mL) and DMF (12 mL) was stirred at room temperature for 3 hr. To the mixture was added water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (NH, ethyl acetate/hexane), and the obtained solid was crystallized from ethyl acetate/hexane to give the title compound (0.82 g).

$^1$H NMR (300 MHz, CDCl$_3$) δ 1.72-1.92 (5H, m), 2.07-2.21 (4H, m), 2.22-2.38 (1H, m), 2.69 (2H, dt, J=11.7, 7.2 Hz), 3.12 (2H, d, J=12.1 Hz), 3.66 (1H, dd, J=9.5, 2.7 Hz), 3.74-3.87 (2H, m), 3.88-4.01 (1H, m), 4.47-4.61 (1H, m), 5.73 (1H, d, J=7.2 Hz), 7.54 (1H, s), 7.60 (1H, d, J=5.3 Hz), 8.31 (1H, d, J=0.8 Hz), 8.35 (1H, d, J=5.3 Hz), 8.39 (1H, s).

B) N-(2-fluoroethyl)-1-(4-(4-methyl-1H-pyrazol-1-yl)pyridin-3-yl)-N-((3S)-tetrahydrofuran-3-yl) piperidine-4-carboxamide To a mixture of 1-(4-(4-methyl-1H-pyrazol-1-yl)pyridin-3-yl)-N-((3S)-tetrahydrofuran-3-yl)piperidine-4-carboxamide (0.12 g) and DMF (2.0 mL) was added sodium hydride (60%, 20 mg), and the mixture was stirred for 30 min. To the mixture was added a solution of 2-fluoroethyl 4-methylbenzenesulfonate (0.11 g) in DMF (1.0 mL), and the mixture was stirred at room temperature for 16 hr. To the mixture was added saturated aqueous ammonium chloride solution, and the mixture was extracted with ethyl acetate. The organic layer was washed with water and saturated brine, and dried over anhydrous sodium sulfate, and the solvent was evaporated under reduced pressure. The residue was purified by silica gel column chromatography (ethyl acetate/hexane) to give the title compound (12 mg).

$^1$H NMR (300 MHz, CDCl$_3$) δ 1.70-2.06 (5H, m), 2.18 (3H, s), 2.23-2.41 (1H, m), 2.62-2.84 (3H, m), 3.06-3.22 (2H, m), 3.51-3.90 (5H, m), 4.03-4.14 (1H, m), 4.42-5.00 (3H, m), 7.54 (1H, s), 7.61 (1H, d, J=5.3 Hz), 8.31-8.43 (3H, m).

Reference Example 19

N-(2-fluoroethyl)-1-(4-(4-methyl-1H-pyrazol-1-yl)pyridin-3-yl)-N-((3R)-tetrahydrofuran-3-yl)piperidine-4-carboxamide A) 1-(4-(4-methyl-1H-pyrazol-1-yl)pyridin-3-yl)-N-((3R)-tetrahydrofuran-3-yl)piperidine-4-carboxamide A mixture of 1-(4-(4-methyl-1H-pyrazol-1-yl)pyridin-3-yl)piperidine-4-carboxylic acid (1.0 g), (R)-tetrahydrofuran-3-amine hydrochloride (0.43 g), HATU (1.7 g), triethylamine (1.9 mL) and DMF (12 mL) was stirred at room temperature for 3 hr. To the mixture was added water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (NH, ethyl acetate/hexane), and the obtained solid was crystallized from ethyl acetate/hexane to give the title compound (0.83 g).

$^1$H NMR (300 MHz, CDCl$_3$) δ 1.67-1.93 (5H, m), 2.05-2.37 (5H, m), 2.69 (2H, dt, J=12.0, 7.2 Hz), 3.12 (2H, d, J=11.7 Hz), 3.67 (1H, dd, J=9.5, 2.3 Hz), 3.73-3.87 (2H, m), 3.88-4.00 (1H, m), 4.55 (1H, dtd, J=7.6, 4.8, 2.8 Hz), 5.75 (1H, d, J=7.2 Hz), 7.54 (1H, s), 7.60 (1H, d, J=4.9 Hz), 8.31 (1H, s), 8.34 (1H, d, J=5.3 Hz), 8.39 (1H, s).

B) N-(2-fluoroethyl)-1-(4-(4-methyl-1H-pyrazol-1-yl)pyridin-3-yl)-N-((3R)-tetrahydrofuran-3-yl)piperidine-4-carboxamide To a mixture of 1-(4-(4-methyl-1H-pyrazol-1-yl)pyridin-3-yl)-N-((3R)-tetrahydrofuran-3-yl)piperidine-4-carboxamide (0.12 g) and DMF (2.0 mL) was added sodium hydride (60%, 20 mg), and the mixture was stirred for 30 min. To the mixture was added a solution of 2-fluoroethyl 4-methylbenzenesulfonate (0.11 g) in DMF (1.0 mL), and the mixture was stirred at room temperature for 16 hr. To the mixture was added saturated aqueous ammonium chloride solution, and the mixture was extracted with ethyl acetate. The organic layer was washed with water and saturated brine, and dried over anhydrous sodium sulfate, and the solvent was evaporated under reduced pressure. The residue was purified by silica gel column chromatography (ethyl acetate/hexane) to give the title compound (12 mg).

$^1$H NMR (300 MHz, CDCl$_3$) δ 1.70-2.04 (5H, m), 2.17 (3H, s), 2.22-2.39 (1H, m), 2.62-2.84 (3H, m), 3.07-3.22 (2H, m), 3.50-3.92 (5H, m), 4.03-4.14 (1H, m), 4.43-5.01 (3H, m), 7.54 (1H, s), 7.61 (1H, d, J=5.3 Hz), 8.31-8.44 (3H, m).

Reference Example 20

(1-(4-(4-bromo-1H-pyrazol-1-yl)pyridin-3-yl)piperidin-4-yl) (3-fluoroazetidin-1-yl)methanone A) 4-(4-bromo-1H-pyrazol-1-yl)-3-fluoropyridine A mixture of p-toluenesulfonic acid monohydrate (0.30 g), 4-chloro-3-fluoropyridine (1.0 g), 4-bromo-1H-pyrazole (1.3 g) and 2-propanol (5.0 mL) was irradiated with microwave at 130° C. for 2 hr. The mixture was allowed to be cooled to room temperature, saturated aqueous sodium bicarbonate solution was added thereto, and the mixture was extracted with ethyl acetate. The organic layer was washed with saturated brine, and dried over anhydrous sodium sulfate, and the solvent was evaporated under reduced pressure. The residue was purified by silica gel column chromatography (ethyl acetate/hexane) to give the title compound (1.5 g).

MS (API+), found: 242.0, 244.0.

B) ethyl 1-(4-(4-bromo-1H-pyrazol-1-yl)pyridin-3-yl)piperidine-4-carboxylate

A mixture of 4-(4-bromo-1H-pyrazol-1-yl)-3-fluoropyridine (3.0 g), ethyl piperidine-4-carboxylate (4.2 mL) and NMP (12 mL) was stirred at 180° C. for 4 hr. The mixture was purified by silica gel column chromatography (ethyl acetate/hexane), and washed with ethyl acetate/hexane to give the title compound (2.3 g).

$^1$H NMR (300 MHz, CDCl$_3$) δ 1.28 (3H, t, J=7.1 Hz), 1.73-1.91 (2H, m), 1.95-2.07 (2H, m), 2.35-2.50 (1H, m), 2.68-2.82 (2H, m), 2.99-3.13 (2H, m), 4.18 (2H, q, J=7.2 Hz), 7.58 (1H, d, J=5.1 Hz), 7.70 (1H, s), 8.39 (1H, d, J=5.1 Hz), 8.44 (1H, s), 8.58 (1H, s).

C) 1-(4-(4-bromo-1H-pyrazol-1-yl)pyridin-3-yl)piperidine-4-carboxylic acid

A mixture of ethyl 1-(4-(4-bromo-1H-pyrazol-1-yl)pyridin-3-yl)piperidine-4-carboxylate (1.2 g), 2M aqueous sodium hydroxide solution (2.4 mL), THF (4.0 mL) and ethanol (4.0 mL) was stirred at room temperature for 3 hr. The mixture was concentrated, and the residue was neutralized with 2M hydrochloric acid (2.4 mL). The precipitate was collected by filtration, washed with water, and dried under reduced pressure to give the title compound (1.1 g).

$^1$H NMR (300 MHz, DMSO-d$_6$) δ 1.54-1.72 (2H, m), 1.77-1.90 (2H, m), 2.26-2.41 (1H, m), 2.64-2.77 (2H, m), 2.83-2.95 (2H, m), 7.52 (1H, d, J=5.1 Hz), 7.96 (1H, s), 8.36 (1H, d, J=5.1 Hz), 8.48 (1H, s), 8.77 (1H, s), 12.26 (1H, s).

D) (1-(4-(4-bromo-1H-pyrazol-1-yl)pyridin-3-yl)piperidin-4-yl) (3-fluoroazetidin-1-yl)methanone A mixture of 1-(4-(4-bromo-1H-pyrazol-1-yl)pyridin-3-yl)piperidine-4-carboxylic acid (0.078 g), 3-fluoroazetidine hydrochloride (0.025 g), HATU (0.11 g), triethylamine (0.12 mL) and DMF (1.0 mL) was stirred at room temperature for 3 hr. To the mixture was added water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (NH, ethyl acetate/hexane), and crystallized from ethyl acetate/hexane to give the title compound (0.052 g).

$^1$H NMR (300 MHz, CDCl$_3$) δ 1.68-2.03 (4H, m), 2.17-2.37 (1H, m), 2.64-2.84 (2H, m), 3.03-3.19 (2H, m), 4.02-4.53 (4H, m), 5.15-5.49 (1H, m), 7.59 (1H, d, J=5.3 Hz), 7.69 (1H, s), 8.39 (1H, d, J=5.3 Hz), 8.44 (1H, s), 8.59 (1H, s).

Reference Example 21

(3-fluoroazetidin-1-yl) (1-(4-(5-methyl-1,3-thiazol-2-yl)pyridin-3-yl)piperidin-4-yl)methanone A) 3-fluoro-N-(2-hydroxypropyl)isonicotinamide A mixture of 3-fluoroisonicotine acid (4.5 g) and thionyl chloride (20 mL) was heated with reflux under nitrogen atmosphere for 4 hr. The mixture was concentrated under reduced pressure, and to the residue was added anhydrous THF (20 mL). To the mixture was added dropwise a mixture of 1-aminopropan-2-ol (2.9 g), DIPEA (12 mL) and THF (20 mL) at 0° C., and the mixture was stirred overnight at room temperature. The mixture was concentrated under reduced pressure, and to the residue was added THF. The insoluble substance was removed by filtration, and the filtrate was concentrated under reduced pressure. The residue was purified by silica gel column chromatography (methanol/ethyl acetate) to give the title compound (4.9 g).

MS (API+): [M+H]+ 199.1.

B) 3-fluoro-N-(2-oxopropyl)isonicotinamide

To a mixture of 3-fluoro-N-(2-hydroxypropyl)isonicotinamide (4.4 g), triethylamine (6.2 mL) and DMSO (70 mL) was added sulfur trioxide complex (7.0 g) at room temperature, and the mixture was stirred overnight. The mixture was concentrated under reduced pressure, and to the residue were added water and ethyl acetate. The mixture was basified with 1M aqueous sodium hydroxide solution, and extracted with ethyl acetate and THF. The organic layer was washed with saturated brine, and dried over anhydrous magnesium sulfate, and the solvent was evaporated under reduced pressure. The residue was purified by silica gel column chromatography (ethyl acetate/hexane) to give the title compound (1.9 g).

MS (API+): [M+H]+ 197.2.

C) 2-(3-fluoropyridin-4-yl)-5-methylthiazole

To a mixture of 3-fluoro-N-(2-oxopropyl)isonicotinamide (1.9 g) and toluene (30 mL) was added 2,4-bis(4-methoxyphenyl)-1,3-dithia-2,4-diphosphetane 2,4-disulfide (4.7 g), and the mixture was stirred at 110° C. for 1 hr. The mixture was concentrated under reduced pressure, and the residue was purified by silica gel column chromatography (NH, ethyl acetate/hexane) to give the title compound (1.0 g).

MS (API+): [M+H]+ 195.1.

D) ethyl 1-(4-(5-methylthiazol-2-yl)pyridin-3-yl)piperidine-4-carboxylate

A mixture of 2-(3-fluoropyridin-4-yl)-5-methylthiazole (500 mg), ethyl piperidine-4-carboxylate (610 mg), potassium carbonate (530 mg) and NMP (2.0 mL) was stirred overnight at 150° C. The mixture was allowed to be cooled to room temperature, and ethyl piperidine-4-carboxylate (2.0 mL) was added thereto. The mixture was stirred at 180° C. for 2 hr, and then overnight at room temperature. The mixture was allowed to be cooled to room temperature, water was added thereto, and the mixture was extracted with ethyl acetate. The organic layer was washed with saturated brine, and dried over anhydrous magnesium sulfate, and the solvent was evaporated under reduced pressure. The residue was purified by silica gel column chromatography (ethyl acetate/hexane) to give the title compound (780 mg).

MS (API+): [M+H]+ 332.2.

E) 1-(4-(5-methylthiazol-2-yl)pyridin-3-yl)piperidine-4-carboxylic acid

Ethyl 1-(4-(5-methylthiazol-2-yl)pyridin-3-yl)piperidine-4-carboxylate (770 mg) was dissolved in THF (5.0 mL) and methanol (2.0 mL), to the solution was added 2M aqueous sodium hydroxide solution (2.3 mL), and the mixture was stirred at room temperature for 2 hr. The mixture was neutralized with 1M hydrochloric acid (4.7 mL), and the precipitated solid was collected by filtration to give the title compound (480 mg).

MS (API+): [M+H]+ 304.1.

F) (3-fluoroazetidin-1-yl) (1-(4-(5-methyl-1,3-thiazol-2-yl)pyridin-3-yl) piperidin-4-yl)methanone A mixture of 1-(4-(5-methyl-1,3-thiazol-2-yl)pyridin-3-yl)piperidine-4-carboxylic acid (0.080 g), 3-fluoroazetidine hydrochloride (0.035 g), HATU (0.12 g), DIPEA (0.12 mL) and DMF (2.0 mL) was stirred at room temperature for 18 hr. The mixture was diluted with ethyl acetate and water, and extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and crystallized from ethyl acetate/heptane to give the title compound (0.071 g).

$^1$H NMR (300 MHz, CDCl$_3$) δ 1.74-1.92 (2H, m), 2.12-2.28 (2H, m), 2.29-2.41 (1H, m), 2.53 (3H, d, J=0.9 Hz), 2.86-2.99 (2H, m), 3.15-3.27 (2H, m), 4.07-4.57 (4H, m), 5.22-5.50 (1H, m), 7.60 (1H, d, J=0.9 Hz), 8.09 (1H, d, J=5.1 Hz), 8.45 (1H, d, J=5.1 Hz), 8.58 (1H, s).

Reference Example 22

((3S)-3-fluoropyrrolidin-1-yl) (1-(4-(5-methyl-1,3-thiazol-2-yl)pyridin-3-yl)piperidin-4-yl)methanone A mixture of 1-(4-(5-methyl-1,3-thiazol-2-yl)pyridin-3-yl)piperidine-4-carboxylic acid (0.080 g), (S)-3-fluoropyrrolidine hydrochloride (0.040 g), HATU (0.12 g), DIPEA (0.12 mL) and DMF (2.0 mL) was stirred at room temperature for 18 hr. The mixture was diluted with ethyl acetate and water, and extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and crystallized from ethyl acetate/heptane to give the title compound (0.075 g).

$^1$H NMR (300 MHz, CDCl$_3$) δ 1.78-2.65 (10H, m), 2.87-3.02 (2H, m), 3.17-3.28 (2H, m), 3.49-4.03 (4H, m), 5.16-5.47 (1H, m), 7.60 (1H, d, J=0.9 Hz), 8.09 (1H, d, J=5.1 Hz), 8.45 (1H, d, J=5.1 Hz), 8.59 (1H, s).

Reference Example 23

N-(4-fluorobenzyl)-N-(2-fluoroethyl)-4-(4-(4-methyl-1H-pyrazol-1-yl)pyridin-3-yl)piperazine-1-carboxamide A) tert-butyl 4-(4-(4-methyl-1H-pyrazol-1-yl)pyridin-3-yl)piperazine-1-carboxylate To a mixture of tert-butyl piperazine-1-carboxylate (0.41 g) and THF (5.0 mL) was added n-butyllithium hexane solution (1.6 M, 1.4 mL) at −78° C., and the mixture was stirred under nitrogen atmosphere for 30 min. To the mixture was added a solution of 3-fluoro-4-(4-methyl-1H-pyrazol-1-yl)pyridine (0.30 g) in THF (1.0 mL), and the mixture was stirred under-nitrogen atmosphere at −78° C. for 15 min. The mixture was allowed to be warmed to room temperature, and stirred for 1 hr. To the mixture was added saturated aqueous ammonium chloride solution, and the mixture was extracted with ethyl acetate. The organic layer was washed with saturated brine, and dried over anhydrous magnesium sulfate, and the solvent was evaporated under reduced pressure. The residue was purified by silica gel column chromatography (ethyl acetate/hexane) to give the title compound (0.26 g).

$^1$H NMR (300 MHz, CDCl$_3$) δ 1.46-1.49 (9H, m), 2.17 (3H, s), 2.81-2.88 (4H, m), 3.45-3.56 (4H, m), 7.55 (1H, s), 7.58 (1H, d, J=5.3 Hz), 8.29 (1H, s), 8.38 (2H, t, J=2.7 Hz).

B) 1-(4-(4-methyl-1H-pyrazol-1-yl)pyridin-3-yl)piperazine

To a mixture of tert-butyl 4-(4-(4-methyl-1H-pyrazol-1-yl)pyridin-3-yl)piperazine-1-carboxylate (1.2 g), ethyl acetate (10 mL) and methanol (5.0 mL) was added 4M hydrogen chloride/ethyl acetate solution (10 mL), and the mixture was stirred overnight at room temperature. The solvent was evaporated under reduced pressure. To the residue was added water, and the mixture was extracted with ethyl acetate. The aqueous solution was basified with 1M aqueous sodium hydroxide solution, saturated brine was added thereto, and the mixture was extracted with a mixed solvent of ethyl acetate and THF. The organic layer was washed with saturated brine, and dried over anhydrous magnesium sulfate, and the solvent was evaporated under reduced pressure to give the title compound (0.86 g).

$^1$H NMR (300 MHz, CDCl$_3$) δ 2.17 (3H, s), 2.81-2.90 (4H, m), 2.91-3.00 (4H, m), 7.54 (1H, s), 7.59 (1H, d, J=4.9 Hz), 8.32-8.43 (3H, m).

C) N-(4-fluorobenzyl)-4-(4-(4-methyl-1H-pyrazol-1-yl)pyridin-3-yl)piperazine-1-carboxamide To a mixture of bis(trichloromethyl) carbonate (31 mg), DIPEA (0.11 mL) and THF (2.0 mL) was added a solution of (4-fluorophenyl)methanamine (0.035 mL) in THF (0.5 mL) under ice-cooling, and the mixture was stirred for 10 min. To the mixture was added a solution of 1-(4-(4-methyl-1H-pyrazol-1-yl)pyridin-3-yl)piperazine (50 mL) in THF (0.5 mL), and the mixture was stirred at room temperature for 30 min. To the mixture was added water, and the mixture was extracted with ethyl acetate. The organic layer was washed with saturated brine, and dried over anhydrous magnesium sulfate, and the solvent was evaporated under reduced pressure. The residue was purified by silica gel column chromatography (NH, ethyl acetate/hexane), and the obtained solid was crystallized from ethyl acetate/hexane to give the title compound (51 mg).

$^1$H NMR (300 MHz, CDCl$_3$) δ 2.16 (3H, s), 2.84-2.92 (4H, m), 3.41-3.51 (4H, m), 4.40 (2H, d, J=5.7 Hz), 4.74 (1H, t, J=5.3 Hz), 6.97-7.06 (2H, m), 7.27-7.33 (2H, m), 7.53-7.59 (2H, m), 8.24 (1H, d, J=0.8 Hz), 8.34-8.42 (2H, m).

D) N-(4-fluorobenzyl)-N-(2-fluoroethyl)-4-(4-(4-methyl-1H-pyrazol-1-yl)pyridin-3-yl)piperazine-1-carboxamide To a mixture of N-(4-fluorobenzyl)-4-(4-(4-methyl-1H-pyrazol-1-yl)pyridin-3-yl)piperazine-1-carboxamide (0.12 g), 15-crown 5-ether (0.079 mL) and THF (2.0 mL) was added sodium hydride (0.016 g) at 0° C., and the mixture was stirred at room temperature for 30 min. To the mixture was added a solution (1.0 mL) of 2-fluoroethyl 4-methylbenzenesulfonate (0.12 g) in THF, and the mixture was stirred at room temperature for 4 days. To the mixture was added aqueous ammonium chloride solution, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane and methanol/ethyl acetate) to give the title compound (0.072 g).

$^1$H NMR (300 MHz, CDCl$_3$) δ 2.17 (3H, s), 2.87-2.96 (4H, m), 3.32-3.50 (6H, m), 4.44-4.67 (4H, m), 6.99-7.09 (2H, m), 7.17-7.25 (2H, m), 7.55 (1H, s), 7.58 (1H, d, J=4.9 Hz), 8.28 (1H, s), 8.36-8.40 (2H, m).

Reference Example 24

N-benzyl-N-(2-fluoroethyl)-4-(4-phenylpyrimidin-5-yl)piperazine-1-carboxamide

A) benzyl 4-(2-oxo-2-phenylethyl)piperazine-1-carboxylate

To a mixture of benzyl piperazine-1-carboxylate (3.1 g), potassium carbonate (2.7 g) and acetonitrile (30 mL) was added dropwise a mixture of 2-chloro-1-phenylethanone (2.0 g) and acetonitrile (20 mL) at room temperature, and the mixture was stirred overnight at room temperature. The solvent was evaporated under reduced pressure, the residue was diluted with water, and the mixture was extracted with ethyl acetate. The organic layer was washed with saturated brine, and dried over anhydrous magnesium sulfate, and the solvent was evaporated under reduced pressure. The residue was purified by silica gel column chromatography (NH, ethyl acetate/hexane) to give the title compound (4.2 g).

MS (API+): [M+H]$^+$ 339.1.

B) benzyl 4-(4-phenylpyrimidin-5-yl)piperazine-1-carboxylate

A mixture of benzyl 4-(2-oxo-2-phenylethyl)piperazine-1-carboxylate (4.2 g) and N,N-dimethylformamide dimethyl acetal (40 mL) was stirred overnight at 100° C. The solvent was evaporated under reduced pressure. To a mixture of the residue, n-butanol (50 mL) and DIPEA (50 mL) was added formamidine acetate (7.7 g), and the mixture was stirred overnight at 110° C. The solvent was evaporated under reduced pressure, the residue was diluted with water, and the mixture was extracted with ethyl acetate. The organic layer was washed with water and saturated brine, and dried over anhydrous magnesium sulfate, and the solvent was evaporated under reduced pressure. The residue was purified by purified by silica gel column chromatography (ethyl acetate/hexane), and then silica gel column chromatography (NH, ethyl acetate/hexane) to give the title compound (3.1 g).

$^1$H NMR (300 MHz, CDCl$_3$) δ 2.92 (4H, brs), 3.46-3.59 (4H, m), 5.12 (2H, s), 7.29-7.39 (5H, m), 7.42-7.52 (3H, m), 7.99-8.07 (2H, m), 8.39 (1H, s), 8.95 (1H, s).

C) 4-phenyl-5-(piperazin-1-yl)pyrimidine

A mixture of benzyl 4-(4-phenylpyrimidin-5-yl)piperazine-1-carboxylate (3.1 g), 10% palladium carbon (about 50% water wet product, 0.30 g) and ethanol (30 mL) was stirred at 50° C. for 3 hr under hydrogen atmosphere. The catalyst was removed by filtration, and the solvent was evaporated under reduced pressure to give the title compound (1.9 g).

MS (API+): [M+H]$^+$ 241.1.

D) N-benzyl-4-(4-phenylpyrimidin-5-yl)piperazine-1-carboxamide

To a mixture of 4-phenyl-5-(piperazin-1-yl)pyrimidine (100 mg) and THF (2.0 mL) was added benzyl isocyanate (0.054 mL) at room temperature, and the mixture was stirred at room temperature for 4 hr. The solvent was evaporated under reduced pressure. The residue was purified by silica gel column chromatography (NH, ethyl acetate/hexane), and the obtained solid was recrystallized from ethyl acetate/hexane to give the title compound (120 mg).

$^1$H NMR (300 MHz, CDCl$_3$) δ 2.85-3.00 (4H, m), 3.28-3.47 (4H, m), 4.42 (2H, d, J=5.3 Hz), 4.69 (1H, t, J=5.1 Hz), 7.27-7.37 (5H, m), 7.41-7.51 (3H, m), 7.99-8.07 (2H, m), 8.40 (1H, s), 8.95 (1H, s).

E) N-benzyl-N-(2-fluoroethyl)-4-(4-phenylpyrimidin-5-yl)piperazine-1-carboxamide To a mixture of N-benzyl-4-(4-phenylpyrimidin-5-yl)piperazine-1-carboxamide (0.11 g), 15-crown 5-ether (0.078 mL) and THF (2.0 mL) was added sodium hydride (16 mg) under ice-cooling, and the mixture was stirred at room temperature for 30 min. To the mixture was added a solution (1.0 mL) of 2-fluoroethyl 4-methylbenzenesulfonate (0.12 g) in THF, and the mixture was stirred at room temperature for 4 days. The reaction was quenched with aqueous ammonium chloride solution, and the mixture was extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane and methanol/ethyl acetate) to give the title compound (43 mg).

$^1$H NMR (300 MHz, CDCl$_3$) δ 2.91-3.01 (4H, m), 3.28-3.50 (6H, m), 4.42-4.65 (4H, m), 7.17-7.38 (5H, m), 7.43-7.52 (3H, m), 8.03-8.10 (2H, m), 8.40 (1H, s), 8.94 (1H, s).

Reference Example 25

(1-(4-(4-bromo-1H-pyrazol-1-yl)pyridin-3-yl)piperidin-4-yl) ((3S)-3-fluoropyrrolidin-1-yl)methanone A mixture of 1-(4-(4-bromo-1H-pyrazol-1-yl)pyridin-3-yl)piperidine-4-carboxylic acid (0.30 g), (S)-3-fluoropyrrolidine hydrochloride (0.13 g), HATU (0.39 g), DIPEA (0.37 mL) and DMF (3.0 mL) was stirred at room temperature for 18 hr. The mixture was diluted with ethyl acetate and water, and extracted with ethyl acetate. The organic layer was washed with water and saturated brine, and dried over anhydrous sodium sulfate, and the solvent was evaporated under reduced pressure. The residue was purified by silica gel column chromatography (NH, ethyl acetate/hexane), and crystallized from ethyl acetate/heptane to give the title compound (0.31 g).

$^1$H NMR (300 MHz, CDCl$_3$) δ 1.73-2.59 (7H, m), 2.68-2.85 (2H, m), 3.06-3.21 (2H, m), 3.47-4.01 (4H, m), 5.14-5.44 (1H, m), 7.59 (1H, d, J=5.3 Hz), 7.69 (1H, s), 8.39 (1H, d, J=5.3 Hz), 8.46 (1H, s), 8.61 (1H, s).

Reference Example 26

(1-(4-(4-cyclopropyl-1H-pyrazol-1-yl)pyridin-3-yl)piperidin-4-yl) (3-fluoroazetidin-1-yl)methanone A mixture of (1-(4-(4-bromo-1H-pyrazol-1-yl)pyridin-3-yl)piperidin-4-yl) (3-fluoroazetidin-1-yl)methanone (0.10 g), potassium carbonate (0.14 g), bis(di-tert-butyl(4-dimethylaminophenyl)phosphine)dichloropalladium(II) (0.017 g), cyclopropyl trifluoroborate potassium salt (0.11 g), toluene (2.0 mL) and water (0.40 mL) was stirred with microwave irradiation at 110° C. for 12 hr. The mixture was purified by silica gel column chromatography (NH, ethyl acetate/hexane) and HPLC (C18, mobile phase: water/acetonitrile (containing 0.1% TFA)). The obtained franctions were concentrated, the residue was neutralized with aqueous sodium hydrogen carbonate solution, and the mixture was extracted with ethyl acetate. The organic layer was washed with water and saturated brine, dried over anhydrous sodium sulfate, and the solvent was evaporated under reduced pressure to give the title compound (0.045 g).

$^1$H NMR (300 MHz, CDCl$_3$) δ 0.56-0.63 (2H, m), 0.88-0.97 (2H, m), 1.67-2.00 (5H, m), 2.21-2.33 (1H, m), 2.63-2.80 (2H, m), 3.05-3.18 (2H, m), 4.04-4.52 (4H, m), 5.18-5.50 (1H, m), 7.46-7.73 (2H, m), 8.30-8.61 (3H, m).

Reference Example 27

(1-(4-(4-cyclopropyl-1H-pyrazol-1-yl)pyridin-3-yl)piperidin-4-yl) ((3S)-3-fluoropyrrolidin-1-yl)methanone A mixture of (S)-(1-(4-(4-bromo-1H-pyrazol-1-yl)pyridin-3-yl)piperidin-4-yl) (3-fluoropyrrolidin-1-yl)methanone (0.10 g), potassium carbonate (0.13 g), bis(di-tert-butyl(4-dimethylaminophenyl)phosphine)dichloropalladium(II) (0.017 g), cyclopropyl trifluoroborate potassium salt (0.11 g), toluene (2.0 mL) and water (0.40 mL) was stirred with microwave irradiation at 110° C. for 12 hr. The mixture was purified by silica gel column chromatography (NH, ethyl acetate/hexane) and HPLC (C18, mobile phase: water/acetonitrile (containing 0.1% TFA)). The obtained franctions were concentrated, the residue was neutralized with aqueous sodium hydrogen carbonate solution, and the mixture was extracted with ethyl acetate. The organic layer was washed with water and saturated brine, dried over anhydrous sodium sulfate, and the solvent was evaporated under reduced pressure to give the title compound (0.046 g).

$^1$H NMR (300 MHz, CDCl$_3$) δ 0.55-0.66 (2H, m), 0.87-0.99 (2H, m), 1.70-2.57 (8H, m), 2.65-2.83 (2H, m), 3.07-3.21 (2H, m), 3.46-4.01 (4H, m), 5.13-5.45 (1H, m), 7.48-7.71 (2H, m), 8.32-8.64 (3H, m).

The compounds of Reference Examples produced according to the above-mentioned methods or a method analogous thereto are shown in the following tables. MS in the tables means actual measured value.

TABLE 1-1

| Reference Example | IUPAC NAME | Structure | MS |
|---|---|---|---|
| 1 | N-cyclopropyl-1-(4-(4-fluorophenyl)pyrimidin-5-yl)-N-methylpiperidine-4-carboxamide | 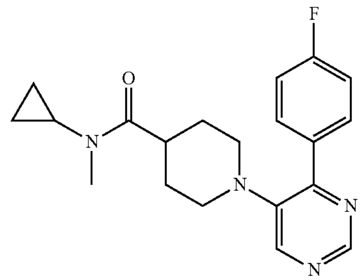 [SMILES: CN(C(=O)C1CCN(c2cncnc2-c2ccc(F)cc2)CC1)C1CC1] | 355.2 |
| 2 | (3-fluoroazetidin-1-yl)(1-(4-(4-fluorophenyl)pyrimidin-5-yl)piperidin-4-yl)methanone | 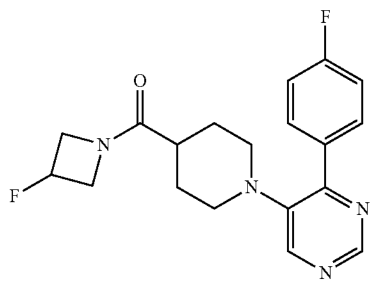 [SMILES: O=C(C1CCN(c2cncnc2-c2ccc(F)cc2)CC1)N1CC(F)C1] | 359.1 |
| 3 | 1-(4-(4-chloro-1H-pyrazol-1-yl)pyridin-3-yl)-N-methyl-N-(tetrahydro-2H-pyran-4-yl)piperidine-4-carboxamide | 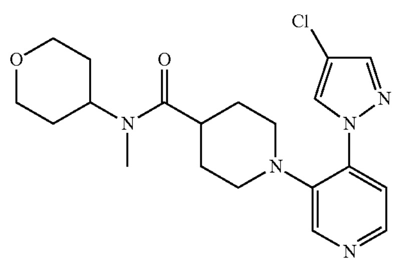 [SMILES: CN(C(=O)C1CCN(c2cnccc2-n2cc(Cl)cn2)CC1)C1CCOCC1] | 404.2 |
| 4 | (3-fluoroazetidin-1-yl)(1-(4-(4-methyl-1H-pyrazol-1-yl)pyridin-3-yl)piperidin-4-yl)methanone | 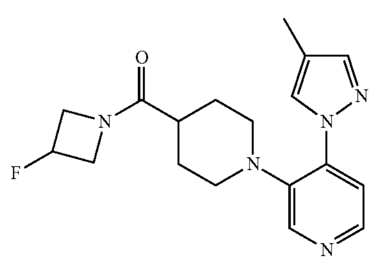 [SMILES: Cc1cnn(-c2ccncc2N2CCC(C(=O)N3CC(F)C3)CC2)c1] | 344.1 |
| 5 | (1-(4-(4-chloro-1H-pyrazol-1-yl)pyridin-3-yl)piperidin-4-yl)(3-fluoroazetidin-1-yl)methanone | 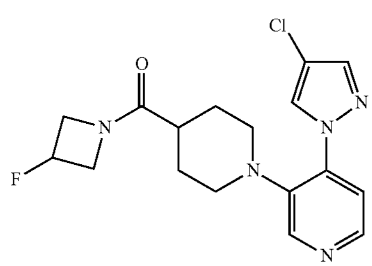 [SMILES: O=C(C1CCN(c2cnccc2-n2cc(Cl)cn2)CC1)N1CC(F)C1] | 364.2 |

TABLE 1-1-continued

| Reference Example | IUPAC NAME | Structure | MS |
|---|---|---|---|
| 6 | ((3S)-3-fluoropyrrolidin-1-yl)(1-(4-(4-methyl-1H-pyrazol-1-yl)pyridin-3-yl)piperidin-4-yl)methanone | 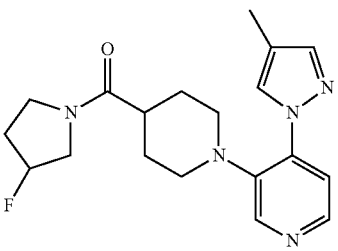 [SMILES: Cc1cnn(-c2ccncc2N2CCC(C(=O)N3CCC(F)C3)CC2)c1] | 358.1 |
| 7 | ((3R)-3-fluoropyrrolidin-1-yl)(1-(4-(4-methyl-1H-pyrazol-1-yl)pyridin-3-yl)piperidin-4-yl)methanone | 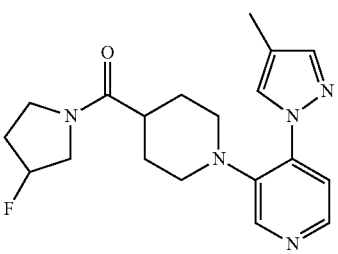 [SMILES: Cc1cnn(-c2ccncc2N2CCC(C(=O)N3CCC(F)C3)CC2)c1] | 358.1 |
| 8 | (1-(4-(4-chloro-1H-pyrazol-1-yl)pyridin-3-yl)piperidin-4-yl)((3S)-3-fluoropyrrolidin-1-yl)methanone | 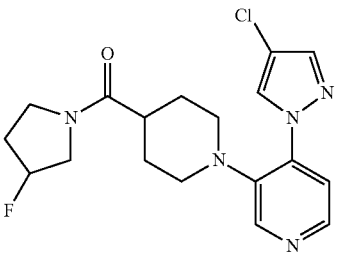 [SMILES: O=C(C1CCN(c2cnccc2-n2cc(Cl)cn2)CC1)N1CCC(F)C1] | 378.1 |
| 9 | (1-(4-(4-chloro-1H-pyrazol-1-yl)pyridin-3-yl)piperidin-4-yl)((3R)-3-fluoropyrrolidin-1-yl)methanone | 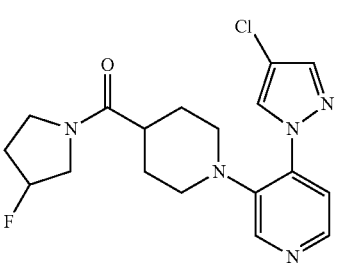 [SMILES: O=C(C1CCN(c2cnccc2-n2cc(Cl)cn2)CC1)N1CCC(F)C1] | 378.1 |

TABLE 1-1-continued

| Reference Example | IUPAC NAME | Structure | MS |
|---|---|---|---|
| 10 | (1-(4-(4-fluorophenyl)pyrimidin-5-yl)piperidin-4-yl)((3S)-3-fluoropyrrolidin-1-yl)methanone | 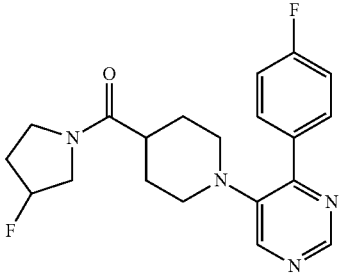 [SMILES: O=C(C1CCN(c2cncnc2-c2ccc(F)cc2)CC1)N1CCC(F)C1] | 373.1 |

TABLE 1-2

| Reference Example | IUPAC NAME | Structure | MS |
|---|---|---|---|
| 11 | (1-(4-(4-fluorophenyl)pyrimidin-5-yl)piperidin-4-yl)((3R)-3-fluoropyrrolidin-1-yl)methanone | 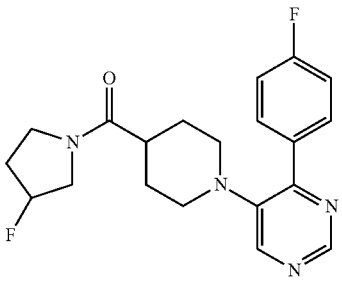 [SMILES: O=C(C1CCN(c2cncnc2-c2ccc(F)cc2)CC1)N1CCC(F)C1] | 373.2 |
| 12 | 1-(4-(4-fluorophenyl)pyrimidin-5-yl)-N-methyl-N-(tetrahydro-2H-pyran-4-yl)piperidine-4-carboxamide | 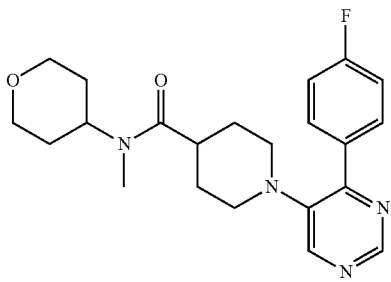 [SMILES: CN(C(=O)C1CCN(c2cncnc2-c2ccc(F)cc2)CC1)C1CCOCC1] | 399.1 |
| 13 | 1-(4-(4-chloro-1H-pyrazol-1-yl)pyridin-3-yl)-N-methyl-N-((3S)-tetrahydrofuran-3-yl)piepridine-4-carboxamide | 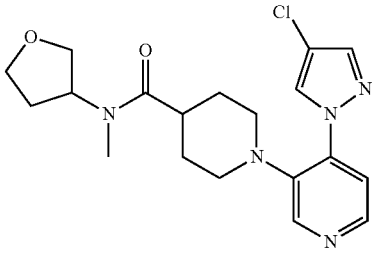 [SMILES: CN(C(=O)C1CCN(c2cnccc2-n2cc(Cl)cn2)CC1)C1CCOC1] | 390.1 |
| 14 | 1-(4-(4-chloro-1H-pyrazol-1-yl)pyridin-3-yl)-N-methyl-N-((3R)-tetrahydrofuran-3-yl)piperidine-4-carboxamide | 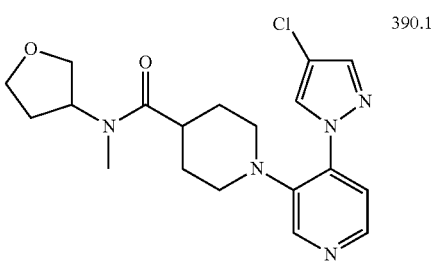 | 390.1 |

TABLE 1-2-continued

| Reference Example | IUPAC NAME | Structure | MS |
|---|---|---|---|
| 15 | 1-(4-(4-fluorophenyl)pyrimidin-5-yl)-N-methyl-N-((3S)-tetrahydrofuran-3-yl)piperidine-4-carboxamide | 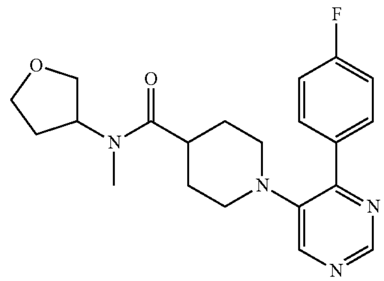 [SMILES: CN(C(=O)C1CCN(c2cncnc2-c2ccc(F)cc2)CC1)C1CCOC1] | 385.1 |
| 16 | 1-(4-(4-fluorophenyl)pyrimidin-5-yl)-N-methyl-N-((3R)-tetrahydrofuran-3-yl)piperidine-4-carboxamide | 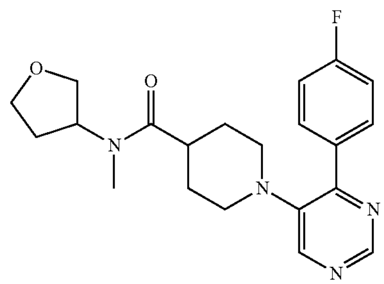 [SMILES: CN(C(=O)C1CCN(c2cncnc2-c2ccc(F)cc2)CC1)C1CCOC1] | 385.1 |
| 17 | N-(2-fluoroethyl)-1-(4-(4-methyl-1H-pyrazol-1-yl)pyridin-3-yl)-N-(tetrahydro-2H-pyran-4-yl)piepridine-4-carboxamide | 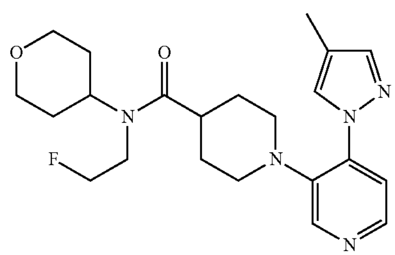 [SMILES: Cc1cnn(-c2ccncc2N2CCC(C(=O)N(CCF)C3CCOCC3)CC2)c1] | 416.2 |
| 18 | N-(2-fluoroethyl)-1-(4-(4-methyl-1H-pyrazol-1-yl)pyridin-3-yl)-N-((3S)-tetrahydrofuran-3-yl)piperidine-4-carboxamide | 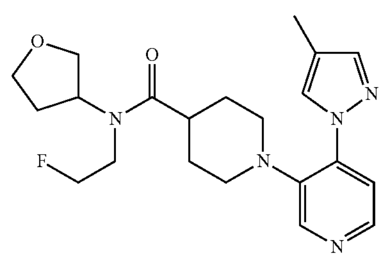 [SMILES: Cc1cnn(-c2ccncc2N2CCC(C(=O)N(CCF)C3CCOC3)CC2)c1] | 402.1 |
| 19 | N-(2-fluoroethyl)-1-(4-(4-methyl-1H-pyrazol-1-yl)pyridin-3-yl)-N-((3R)-tetrahydrofuran-3-yl)piperidine-4-carboxamide | 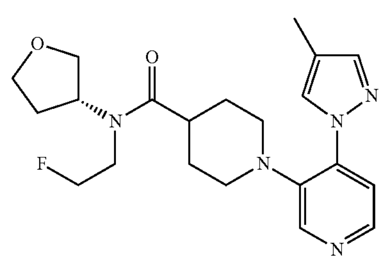 [SMILES: Cc1cnn(-c2ccncc2N2CCC(C(=O)N(CCF)[C@@H]3CCOC3)CC2)c1] | 402.1 |

TABLE 1-2-continued

| Reference Example | IUPAC NAME | Structure | MS |
|---|---|---|---|
| 20 | (1-(4-(4-bromo-1H-pyrazol-1-yl)pyridin-3-yl)piperidin-4-yl)(3-fluoroazetidin-1-yl)methanone | 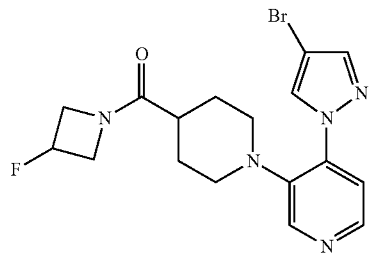 [SMILES: O=C(C1CCN(c2cnccc2-n2cc(Br)cn2)CC1)N1CC(F)C1] | 408.0 |

TABLE 1-3

| Reference Example | IUPAC NAME | Structure | MS |
|---|---|---|---|
| 21 | (3-fluoroazetidin-1-yl)(1-(4-(5-methyl-1,3-thiazol-2-yl)pyridin-3-yl)piperidin-4-yl)methanone | 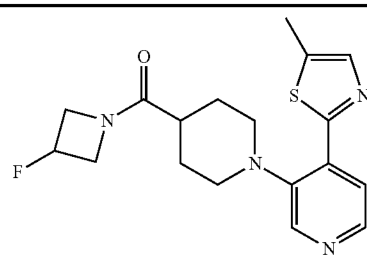 | 361.1 |
| 22 | ((3S)-3-fluoropyrrolidin-1-yl)(1-(4-(5-methyl-1,3-thiazol-2-yl)pyridin-3-yl)piperidin-4-yl)methanone | 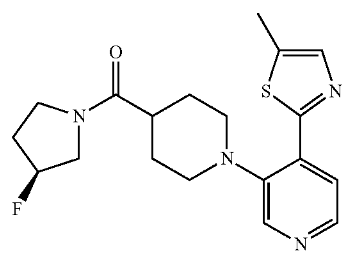 [SMILES: Cc1cnc(-c2ccncc2N2CCC(C(=O)N3CC[C@H](F)C3)CC2)s1] | 375.0 |
| 23 | N-(4-fluorobenzyl)-N-(2-fluoroethyl)-4-(4-(4-methyl-1H-pyrazol-1-yl)pyridin-3-yl)piperazine-1-carboxamide | 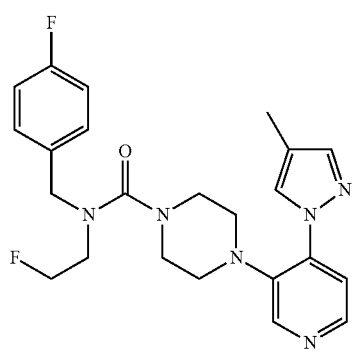 [SMILES: Cc1cnn(-c2ccncc2N2CCN(C(=O)N(CCF)Cc3ccc(F)cc3)CC2)c1] | 441.1 |
| 24 | N-benzyl-N-(2-fluoroethyl)-4-(4-phenylpyrimidin-5-yl)piperazine-1-carboxamide | 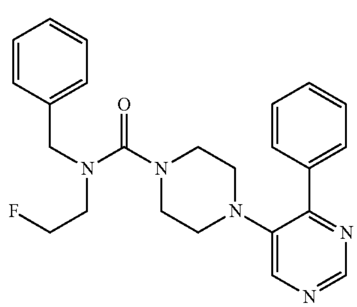 [SMILES: O=C(N1CCN(c2cncnc2-c2ccccc2)CC1)N(CCF)Cc1ccccc1] | 420.0 |

TABLE 1-3-continued

| Reference Example | IUPAC NAME | Structure | MS |
|---|---|---|---|
| 25 | (1-(4-(4-bromo-1H-pyrazol-1-yl)pyridin-3-yl)piperidin-4-yl)((3S)-3-fluoropyrrolidin-1-yl)methanone | 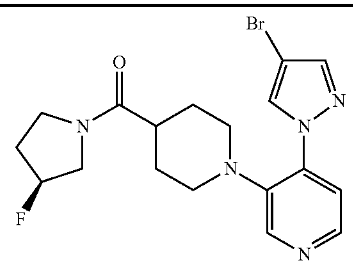 | 421.9 |
| 26 | (1-(4-(4-cyclopropyl-1H-pyrazol-1-yl)pyridin-3-yl)piperidin-4-yl)(3-fluoroazetidin-1-yl)methanone | 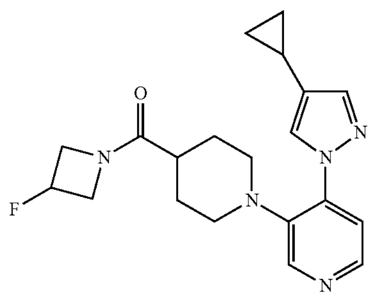 [SMILES: O=C(C1CCN(c2cnccc2-n2cc(C3CC3)cn2)CC1)N1CC(F)C1] | 370.0 |
| 27 | (1-(4-(4-cyclopropyl-1H-pyrazol-1-yl)pyridin-3-yl)piperidin-4-yl)((3S)-3-fluoropyrrolidin-1-yl)methanone | 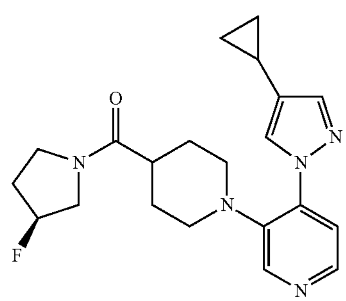 [SMILES: O=C(C1CCN(c2cnccc2-n2cc(C3CC3)cn2)CC1)N1CC[C@H](F)C1] | 384.0 |

EXAMPLES

Radiochemical labeling was performed using a GE TRACERlab FXFN module using helium pressure or vacuum for fluid transfers. [$^{18}$F]Fluoride was purchased from Cardinal Health (Hartford, Conn.) or NCM (Bronx, N.Y.). All chemicals were purchased from Sigma-Aldrich (St Louis, Mo.) or ABX (Radeberg, Germany). Chemical and radiochemical purities were assessed by HPLC (Waters 1525 or 2695, or Agilent G1312A) equipped with ultraviolet (Waters 2489 or Agilent 1315B, λ=254 nM) and gamma (Bioscan FC-3200) detectors. The HPLC conditions used a Waters XBridge C18 (5 μm, 4.6×250 mm) analytical column, eluting with a 15 min gradient mixture of methanol (eluent A) and sodium phosphate buffer (pH 6, 10 mM, eluent B) at a flow rate of 1 mL/min (gradient from 50% to 90% A over 12 min, hold for 1 min, re-equilibration at 50% A for 2 min). The data were analyzed with Waters Empower software. Radioactivity was measured with a Capintec CRC-25 dose calibrator. Radionuclidic identity was determined by gamma spectroscopy using a Canberra 802 multi-channel analyzer. A pH measurement was performed with a pH meter (Orion Star A211) fitted with a micro electrode. Cryptand 222 (Kryptofix-222) content was measured using a TLC test (eluent: dichloromethane/methanol 90/10 stain reagent: iodoplatinate). Residual solvent analysis was performed on a Perkin-Elmer Clarus 500 gas chromatograph fitted with a Restek Stabilwax (30 m×0.53 mm×1 μm) column, using a flow rate of 14.7 mL/min of helium as carrier and of temperature gradient as following: hold at 40° C. for 3.0 min, then 25° C. per min until temperature reaches 210° C., and hold at 210° C. for 2.2 min). Pyrogen content was measured with a Charles River Laboratories Endosafe PTS-100. Sterility tests were performed by inoculating a sample of the drug product in fluid thioglycollate medium and tripticase soy broth (Northeast Laboratories) and monitoring for two weeks, per USP guidelines.

Example 1

(1-(4-(4-chloro-1H-pyrazol-1-yl)pyridin-3-yl)piperidin-4-yl) (3-[$^{18}$F]fluoroazetidin-1-yl)methanone A) (1-(4-(4-chloro-1H-pyrazol-1-yl)pyridin-3-yl) piperidin-4-yl)(3-hydroxyazetidin-1-yl)methanone A mixture of 1-(4-(4-chloro-1H-pyrazol-1-yl)pyridin-3-yl)piperidine-4-carboxylic acid (0.60 g), azetidin-3-ol hydrochloride (0.28 g), HATU (0.97 g), DIPEA (1.0 mL) and DMF (7.0 mL) was stirred at room temperature for 24 h. The mixture was diluted with brine and ethyl acetate and the resultant precipitates were collected, washed with water and dried in vacuo to give the title compound (0.49 g).

$^1$H NMR (300 MHz, DMSO-$d_6$) δ 1.51-1.70 (4H, m), 2.23-2.38 (1H, m), 2.63-2.79 (2H, m), 2.84-2.96 (2H, m), 3.56 (1H, dd, J=10.0, 4.3 Hz), 3.87 (1H, dd, J=8.7, 4.1 Hz), 4.01 (1H, dd, J=10.0, 7.0 Hz), 4.27-4.51 (2H, m), 5.70 (1H, d, J=6.0 Hz), 7.52 (1H, d, J=4.9 Hz), 7.96 (1H, s), 8.36 (1H, d, J=4.9 Hz), 8.48 (1H, s), 8.76 (1H, s)

B) 1-(1-(4-(4-chloro-1H-pyrazol-1-yl)pyridin-3-yl) piperidine-4-carbonyl)azetidin-3-yl 4-methylbenzenesulfonate A mixture of (1-(4-(4-chloro-1H-pyrazol-1-yl)pyridin-3-yl)piperidin-4-yl) (3-hydroxyazetidin-1-yl)methanone (0.48 g), 4-methylbenzene-1-sulfonyl chloride (0.38 g), triethylamine (0.56 mL), trimethylamine hydrochloride (51 mg) and acetonitrile (15 mL) was stirred at room temperature for 18 h. The mixture was diluted with water and the resultant precipitates were collected, washed with water and dried in vacuo. The crude solids were recrystallized from ethanol to give the title compound (0.34 g).
$^1$H NMR (300 MHz, CDCl$_3$) δ 1.66-1.96 (4H, m), 2.16-2.29 (1H, m), 2.48 (3H, s), 2.64-2.79 (2H, m), 3.02-3.16 (2H, m), 3.88-3.99 (1H, m), 4.12-4.34 (2H, m), 4.38-4.49 (1H, m), 5.03-5.15 (1H, m), 7.35-7.42 (2H, m), 7.58 (1H, d, J=5.3 Hz), 7.65 (1H, s), 7.76-7.83 (2H, m), 8.39 (1H, d, J=5.3 Hz), 8.43 (1H, s), 8.53 (1H, s).

C) (1-(4-(4-chloro-1H-pyrazol-1-yl)pyridin-3-yl) piperidin-4-yl) (3-[$^1$F]fluoroazetidin-1-yl)methanone

[$^{18}$F]Fluoride in target water (0.5 to 3 mL) was transferred onto an ion-exchange solid phase extraction (SPE) cartridge (Waters QMA light, pre-conditioned). The cartridge was eluted into a pre-heated (60° C.) reactor vial with a solution of cryptand-222 (10 mg, 27 μmol) and potassium carbonate (1.2 mg, 9.4 μmol) in acetonitrile (0.8 mL) and sterile water for injection (WFI) (0.2 mL). The reactor was heated to 95° C. under vacuum with a stream of helium for 4 min before addition of acetonitrile (1 mL). The evaporation was continued for 2 min before acetonitrile (1 mL) was added. The azeotrope was continued for a further 2 min before the reactor was cooled to 60° C. A solution of (1-(1-(4-(4-chloro-1H-pyrazol-1-yl)pyridin-3-yl)piperidine-4-carbonyl) azetidin-3-yl 4-methylbenzenesulfonate (1 mg, 2.0 μmol) in anhydrous dimethylsulfoxide (1.0 mL) was added thereto and heated to 120° C. After 10 min, the mixture was cooled to 40° C., and diluted with preparative HPLC mobile phase (2.5 mL) and WFI (2.0 mL). The resulting mixture was injected onto a prep-HPLC column (Phenomenex Luna C18(2), 10×250 mm) and eluted with a mixture of HPLC-grade acetonitrile/HPLC grade water (35/65 v/v) at a flow rate of 4 mL/min. The eluent was monitored by ultraviolet (λ=254 nm) and radioactive detectors connected in series. The product-containing fraction (retention time of 800-900 s) was collected, diluted with WFI (15 mL) and transferred onto a SPE cartridge (Waters Sep-Pak tC18 light, pre-rinsed with 6 mL ethanol and 6 mL WFI). The cartridge was rinsed with WFI (10 mL) and the product was eluted with ethanol (1 mL) and diluted with a solution of ascorbic acid in normal saline (14 mL of a 0.8 mg/mL solution). The diluted product was transferred through a sterilizing filter (Millex LG 0.22 μm, Millipore) into a vented final product vial, containing normal saline (15 mL) and which had been assembled under aseptic conditions. The product was identified by analytical HPLC using co-injection of the non-radioactive reference compound (Reference Example 5) by comparing the retention times (Rt) of the UV and radioactive peaks.

Rt: 8.592 min (radioactive product)
Rt: 8.475 min (reference compound)

Example 2

(3-[$^{18}$F]fluoroazetidin-1-yl) (1-(4-(4-fluorophenyl) pyrimidin-5-yl)piperidin-4-yl)methanone A) (1-(4-(4-fluorophenyl)pyrimidin-5-yl)piperidin-4-yl) (3-hydroxyazetidin-1-yl)methanone A mixture of 1-(4-(4-fluorophenyl)pyrimidin-5-yl)piperidine-4-carboxylic acid (0.70 g), azetidin-3-ol hydrochloride (0.33 g), HATU (1.1 g), DIPEA (1.2 mL) and DMF (7.0 mL) was stirred at room temperature for 5 hr. The mixture was diluted with ethyl acetate and water, and then extracted with ethyl acetate. The organic layer was separated, washed with water and brine, dried over sodium sulfate, and concentrated in vacuo. The residue was purified by silica gel column chromatography (NH, ethyl acetate/hexane and methanol/ ethyl acetate) to give the title compound (0.68 g).
$^1$H NMR (300 MHz, CDCl$_3$) δ 1.62-1.94 (4H, m), 2.17-2.31 (1H, m), 2.40 (1H, d, J=5.7 Hz), 2.58-2.72 (2H, m), 3.20-3.34 (2H, m), 3.87 (1H, dd, J=10.6, 4.1 Hz), 4.01 (1H, dd, J=9.1, 4.2 Hz), 4.20-4.43 (2H, m), 4.64-4.77 (1H, m), 7.13-7.21 (2H, m), 8.09-8.18 (2H, m), 8.40 (1H, s), 8.90 (1H, s).

B) 1-((1-(4-(4-fluorophenyl)pyrimidin-5-yl)piperidin-4-yl)carbonyl)azetidin-3-yl 4-methylbenzenesulfonate A mixture of (1-(4-(4-fluorophenyl)pyrimidin-5-yl)piperidin-4-yl) (3-hydroxyazetidin-1-yl)methanone (0.67 g), 4-methylbenzene-1-sulfonyl chloride (0.54 g), triethylamine (0.79 mL), trimethylamine hydrochloride (0.036 g) and acetonitrile (15 mL) was stirred at room temperature for 30 min. The mixture was diluted with water and the resultant precipitates were collected, washed with water and ethyl acetate, and dried in vacuo. The crude solids were recrystallized from ethyl acetate/heptane to give the title compound (0.31 g).
$^1$H NMR (300 MHz, CDCl$_3$) δ 1.61-1.89 (4H, m), 2.11-2.24 (1H, m), 2.47 (3H, s), 2.57-2.70 (2H, m), 3.20-3.33 (2H, m), 3.92 (1H, dd, J=11.6, 4.1 Hz), 4.16 (1H, dd, J=11.0, 6.9 Hz), 4.26 (1H, dd, J=10.1, 3.5 Hz), 4.37-4.46 (1H, m), 5.02-5.11 (1H, m), 7.11-7.20 (2H, m), 7.35-7.42 (2H, m), 7.76-7.82 (2H, m), 8.07-8.17 (2H, m), 8.40 (1H, s), 8.90 (1H, s).

C) (3-[$^{18}$F]fluoroazetidin-1-yl) (1-(4-(4-fluorophenyl)pyrimidin-5-yl) piperidin-4-yl)methanone

[$^{18}$F]Fluoride in target water (0.5 to 3 mL) was transferred onto an ion-exchange solid phase extraction (SPE) cartridge (Waters QMA light, pre-conditioned). The cartridge was eluted into a pre-heated (60° C.) reactor vial with a solution of cryptand-222 (10 mg) and potassium carbonate (1.2 mg) in acetonitrile (0.8 mL) and sterile water for injection (WFI) (0.2 mL). The reactor was heated to 95° C. under vacuum with a stream of helium for 4 min before addition of acetonitrile (1 mL). The evaporation was continued for 2 min before acetonitrile (1 mL) was added. The azeotrope was continued for a further 2 min before the reactor was cooled to 60° C. A solution of 1-((1-(4-(4-fluorophenyl) pyrimidin-5-yl)piperidin-4-yl)carbonyl)azetidin-3-yl 4-methylbenzenesulfonate (1 mg) in anhydrous dimethylsulfoxide (1.0 mL) was added thereto and heated to 120° C. After 10 min, the mixture was cooled to 40° C., and diluted with preparative HPLC mobile phase (2.5 mL) and WFI (2.0 mL). The resulting mixture was injected onto a prep-HPLC column (Phenomenex Luna C18(2), 10×250 mm) and eluted with a mixture of HPLC-grade acetonitrile/HPLC grade water (35/65 v/v) at a flow rate of 4 mL/min. The eluent was monitored by ultraviolet ($\lambda$=254 nm) and radioactive detectors connected in series. The product-containing fraction (retention time of 800-900 s) was collected, diluted with WFI (15 mL) and transferred onto a SPE cartridge (Waters Sep-Pak tC18 light, pre-rinsed with 6 mL ethanol and 6 mL WFI). The cartridge was rinsed with WFI (10 mL) and the product was eluted with ethanol (1 mL) and diluted with a solution of ascorbic acid in normal saline (14 mL of a 0.8 mg/mL solution). The diluted product was transferred through a sterilizing filter (Millex LG 0.22 μm, Millipore) into a vented final product vial, containing normal saline (15 mL) and which had been assembled under aseptic conditions. The product was identified by analytical HPLC using co-injection of the non-radioactive reference compound (Reference Example 2) by comparing the retention times (Rt) of the UV and radioactive peaks.

Rt: 8.450 min-(radioactive product)
Rt: 8.345 min (reference compound)

Examples 3-15

In the same manner as in Examples 1 and 2, the compounds of Reference Examples 4, 6-11, 20-22 and 25-27 are radiolabeled with $^{18}$F.

EXPERIMENTAL EXAMPLES

Experimental Example 1

Construction of Human CH24H (CYP46) Expression Vector

A plasmid DNA for expressing human CH24H in a FreeStyle 293 cell was produced as follows. Using Full-Length Mammalian Gene Collection No. 4819975 (Invitrogen) as a template, and the following two kinds of synthesized DNAs:

```
                                      (SEQ ID NO: 1)
5'-GCCCCGGAGCCATGAGCCCCGGGCTG-3'
and (SEQ ID NO: 2)
5'-GTCCTGCCTGGAGGCCCCCTCAGCAG-3',
```

PCR was performed to amplify 91-1625 bp region of human CH24H (BC022539). The obtained fragment was cloned using TOPO TA Cloning Kit (Invitrogen). The obtained fragment was subcloned to pcDNA3.1(+) digested with BamHI and XhoI to give a plasmid DNA for human CH24H expression (pcDNA3.1(+)/hCH24H).

Experimental Example 2

Expression of Human CH24H and Preparation of Human CH24H Lysate

The expression of human CH24H was performed using FreeStyle 293 Expression System (Invitrogen). According to the manual attached to FreeStyle 293 Expression System and using the plasmid DNA for human CH24H expression (pcDNA3.1(+)/hCH24H) constructed in Experimental Example 1, a transient expression using FreeStyle 293-F cell was performed. After transfection, the cells were cultured at 37° C., 8% $CO_2$ with shaking at 125 rpm for 2 days. The cells were collected by centrifugation, and suspended in a suspension buffer (100 mM potassium phosphate (pH 7.4), 0.1 mM EDTA, 1 mM DTT, 20% Glycerol). The suspended product was disrupted by a polytron homogenizer (manufactured by Kinematica), and centrifuged at 9000×g for 10 min, and the supernatant was collected. The collected supernatant was cryopreserved (−80° C.) as a human CH24H lysate standard product.

Experimental Example 3

Measurement of CH24H Inhibitory Activity

For the measurement of CH24H inhibitory activity, using the human CH24H lysate prepared in Experimental Example 2, the amount of 24-HC produced from cholesterol by catalytic activity of CH24H was measured in the presence of a test compound, and compared with that measured in the absence of the test compound. That is, a test compound solution at various concentrations was mixed with a reaction buffer (50 mM potassium phosphate containing 0.1% BSA and Complete, EDTA-free, pH 7.4) and human CH24H lysate. Then, [$^{14}$C] cholesterol (53 mCi/mmol specific activity, 15 μM) was added, and CH24H reaction was performed at 37° C. for 5 hr. After completion of the reaction, a quenching solution consisting of chloroform/methanol/distilled water (2:2:1 v/v) was added, and the resulting 24-HC was extracted by shaking. The extract was applied to silica gel thin layer chromatography (ethyl acetate:toluene=4:6), and the obtained $^{14}$C-24HC fraction was measured with BAS2500 (Fujifilm Corporation).

The inhibitory rate (%) and $IC_{50}$ values (μM) were calculated from the ratio of radioactivity in the presence of a test compound relative to the radioactivity in the absence of the test compound. The results are shown in the following Table 2.

TABLE 2

| Test Compound | $IC_{50}$ (μM) |
| --- | --- |
| Reference Example 1 | 0.0054 |
| Reference Example 2 | 0.0088 |
| Reference Example 3 | 0.0074 |
| Reference Example 4 | 0.0071 |
| Reference Example 5 | 0.019 |
| Reference Example 10 | 0.020 |
| Reference Example 11 | 0.016 |
| Reference Example 13 | 0.020 |
| Reference Example 14 | 0.017 |
| Reference Example 20 | 0.0069 |
| Reference Example 21 | 0.0049 |
| Reference Example 23 | 0.017 |
| Reference Example 26 | 0.010 |

Experimental Example 4

Selectivity Assay

Selectivity assay over other CNS related human receptors and enzymes were performed by the method of Eurofins Panlabs Taiwan, Ltd. (Catalog: https://www.eurofinspanlabs.com/Catalog/AssayCatalog/AssayCatalog.aspx). The assay names and their methods are listed in the following Tables 3-1 and 3-2. (3-Fluoroazetidin-1-yl) (1-(4-(4-fluorophenyl)pyrimidin-5-yl)piperidin-4-yl)methanone (Reference Example 2) showed less than 50% inhibition at 10 μM in the assay listed in Tables 3-1 and 3-2.

TABLE 3-1

| Assay name | substrate/ligand | species |
|---|---|---|
| Adenosine A2B | [$^3$H]MRS1754 | human |
| Adrenergic β1 | [$^{125}$I]Cyanopindolol | human |
| Adrenergic β2 | [$^3$H]CGP-12177 | human |
| Adrenergic β3 | [$^{125}$I]Cyanopindolol | human |
| Angiotensin AT2 | [$^{125}$I]CGP-42112A | human |
| Bradykinin B1 | [$^3$H](Des-Arg$^{10}$)-Kallidin | human |
| Cannabinoid CB1 | [$^3$H]SR141716A | human |
| Carbonic Anhydrase II | 4-Nitrophenyl acetate (4-NPA) | human |
| Cholinesterase, Acetyl, ACES | Acethylthiocholine | human |
| Cyclooxygenase (COX-1) | Arachidonic acid | human |
| Cyclooxygenase (COX-2) | Arachidonic acid | human |
| Dopamine D1 | [$^3$H]SCH-23390 | human |
| Dopamine D2L | [$^3$H]Spiperone | human |
| Dopamine D3 | [$^3$H]Spiperone | human |
| Dopamine D4.2 | [$^3$H]Spiperone | human |
| GABA B1A | [$^3$H]CGP-54626 | human |
| GABA B1B | [$^3$H]CGP-54626 | human |
| Histamine H1 | [$^3$H]Pyrilamine | human |
| Histamine H2 | [$^{125}$I]Aminopotentidine | human |
| Imidazoline I2(Central) | [$^3$H]Idazoxan | human |
| MAO A | Kynuramine | human |
| MAO B | Kynuramine | human |
| Muscarinic M1 | [$^3$H]N-Methylscopolamine | human |
| Muscarinic M2 | [$^3$H]N-Methylscopolamine | human |
| Muscarinic M3 | [$^3$H]N-Methylscopolamine | human |
| Opiate κ (OP2, KOP) | [$^3$H]Diprenorphine | human |
| Opiate μ (OP3, MOP) | [$^3$H]Diprenorphine | human |

TABLE 3-2

| Assay name | substrate/ligand | species |
|---|---|---|
| Peptidase, Metalloproteinase, Neutral Endopeptidase | Glutaryl-Ala-Ala-Phe-4-methoxy-2-naphthylamide | human |
| Phosphodiesterase 4 (PDE4) | [$^3$H]cAMP + cAMP | human |
| Phosphodiesterase 5 (PDE5) | [$^3$H]cGMP + cGMP | human |
| 5-HT2B | [$^3$H]Lysergic acid diethylamide (LSD) | human |
| NK2 | [$^3$H]SR-48968 | human |
| NK3 | [$^{125}$I]MePhe$^7$-Neurokinin B | human |
| Dopamine transporter (DAT) | [$^{125}$I]RTI-55 | human |
| Norepinephrine transporter (NET) | [$^{125}$I]RTI-55 | human |
| Serotonin transporter (SERT) | [$^3$H]Paroxetine | human |
| Vasopressin V1A | [$^{125}$I]Phenyl-acetylTyr(Me)PheGlnAsnArgProArgTyr | human |

Experimental Example 5

PET Measurements and Image Analysis

A. Study Design

PET imaging was conducted over 4 hours following intravenous injection as a bolus of the radiopharmaceutical in non-human primate female rhesus macaque (macaca mulatta, body weight: 9.3 kg) to study the in vivo pharmacokinetics of (1-(4-(4-chloro-1H-pyrazol-1-yl)pyridin-3-yl)piperidin-4-yl) (3-[$^{18}$F]fluoroazetidin-1-yl)methanone (Example 1, injected dose: 5.26 mCi, injected mass: 0.270 μg) and (3-[$^{18}$F]fluoroazetidin-1-yl) (1-(4-(4-fluorophenyl)pyrimidin-5-yl)piperidin-4-yl)methanone (Example 2, injected dose: 4.93 mCi, injected mass: 0.431 μg).

B. Monitoring

Animals were fasted for 18-24 h before the study. At 2 h prior to injection of the radiopharmaceutical, the animals were anesthetized with intramuscular ketamine (10 mg/kg) and glycopyrrolate (0.01 mg/kg), transferred to the PET camera, and immediately intubated with an endrotracheal tube for continued anesthesia with 2.75% isoflurane administered through a rebreathing circuit. Body temperature was kept at 37° C. using a heated water blanket. Vital signs, including heart rate, blood pressure, respiration rate, oxygen saturation and body temperature, were monitored every 3 to 20 min during the study.

C. PET Imaging

An intravenous line was placed and used for injection of the radiopharmaceuticals Example 1 and Example 2. Following the intravenous injection of example 1 or example 2 as a bolus over 3 min, a series of up to 57 dynamic 3D PET scans were obtained continuously on a microPET Focus 220 camera (Siemens Medical Solutions, Inc.) over four hours as follows: 6×30 s, 3×1 min, 2×2 min, and 46×5 min frames. The dynamic series were subsequently reconstructed using filtered back projection with corrections for random, scatter, and attenuation provided by the camera manufacturer.

D. Blood Sampling

Four standards of 5 mL were drawn prior to injection of example 1 or example 2. Four samples of 5 mL were drawn at 3, 10, 30 and 60 min post injection to evaluate the stability in blood as well as the metabolite analysis method and HPLC conditions.

E. Image Analysis

Reconstructed PET image data volumes were transferred to the image processing PMOD software package (PMOD Technologies, Zurich, Switzerland) where the images were realigned with the monkey's individual MRI to apply a volume of interest (VOI) template comprising the following regions: whole brain, caudate nucleus, putamen, globus pallidus, frontal cortex, temporal cortex, occipital cortex, parietal cortex, anterior cingulate cortex, posterior cingulated cortex, hippocampus, thalamus, and cerebellum. Average activity concentration (kBq/cc) within each VOI was determined and time activity curves (TAC) were generated for each study, depicting the regional brain activity concentration over time and reflecting total uptake (specific plus non displaceable). Time activity curves were also expressed in SUV (Standard Uptake Value) units (g/mL) by normalizing by the weight of the animal and the injected dose. Logan graphical analysis with reference region input function was applied to the regional time activity curves with t* fixed at 40 min to obtain an estimate of $BP_{ND}$ (Binding Potential relative to the Non-Displaceable compartment), where the cerebellum was used as the reference region.

Figure 2:
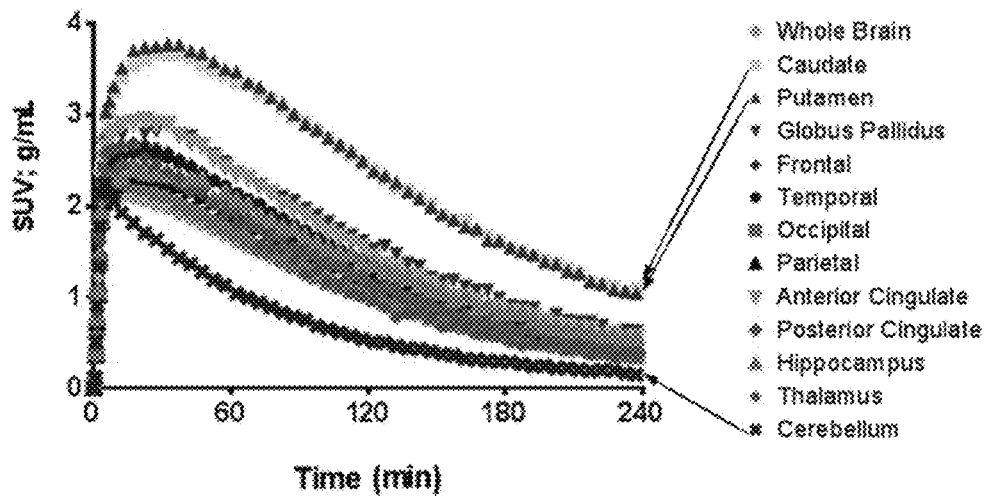
FIG. 2 shows time activity curves (TAC) of regional brain uptake of Example 2.

Time activity curves (TAC) of regional brain uptake are shown in FIG. 1 (Example 1, SUV) and FIG. 2 (Example 2, SUV).

Example 1 and Example 2 showed the highest uptake in the putamen and caudate, followed by globus pallidus, followed by lower uptake in the cortical regions and other nuclei such as the thalamus. The lowest uptake was seen in the cerebellum. The brain distribution of both example 1 and example 2 are in accordance with the expected CH24H distribution in brain.

Example 1 and Example 2 present favorable kinetics with a significant washout following the maximum uptake. The maximum SUV in the putamen was 2.8 (Example 1, at ~45 min post injection) and 3.8 (Example 2, at ~30 min post injection). The whole-brain maximum % ID was 1.6%

(Example 1) and 2.3% (Example 2). The $BP_{ND}$ in the putamen was 2.3 (Example 1) and 2.6 (Example 2).

INDUSTRIAL APPLICABILITY

The radiolabeled compounds of the present invention are useful as radiotracers for quantitative imaging of CH24H in mammals.

This application is based on patent application No. 62/009,526 filed in USA, the contents of which are incorporated in full herein.

The invention claimed is:

1. A compound represented by the formula (I):

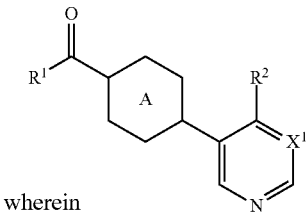

wherein
$R^1$ is
(1) a 3- to 8-membered monocyclic non-aromatic heterocyclic group substituted by 1 to 3 radiolabeled halogen atoms, or
(2) an amino group mono- or di-substituted by substituent(s) selected from the group consisting of:
  (a) a $C_{1-6}$ alkyl group substituted by 1 to 3 radiolabeled halogen atoms, and
  (b) a radiolabeled $C_{1-6}$ alkyl group,
and optionally further substituted by a substituent selected from the group consisting of:
  (c) a $C_{1-6}$ alkyl group substituted by 1 to 3 halogen atoms,
  (d) a $C_{1-6}$ alkyl group optionally substituted by $C_{6-14}$ aryl group(s) optionally substituted by 1 to 3 halogen atoms,
  (e) a $C_{3-8}$ cycloalkyl group, and
  (f) a 3- to 8-membered monocyclic non-aromatic heterocyclic group;

$R^2$ is
(1) a $C_{6-14}$ aryl group optionally substituted by 1 to 3 halogen atoms, or
(2) a 5- or 6-membered monocyclic aromatic heterocyclic group optionally substituted by 1 to 3 substituents selected from the group consisting of:
  (a) a halogen atom,
  (b) a $C_{1-6}$ alkyl group, and
  (c) a $C_{3-8}$ cycloalkyl group;

$X^1$ is CH or N; and
Ring A is

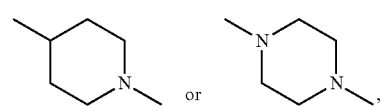

or a salt thereof.

2. The compound or salt of claim 1, wherein $R^1$ is
(1) a 3- to 8-membered monocyclic non-aromatic heterocyclic group substituted by one radiolabeled halogen atom, or
(2) an amino group substituted by one substituent selected from the group consisting of:
  (a) a $C_{1-6}$ alkyl group substituted by one radiolabeled halogen atom, and
  (b) a radiolabeled $C_{1-6}$ alkyl group,
and further substituted by one substituent selected from the group consisting of:
  (c) a $C_{1-6}$ alkyl group optionally substituted by $C_{6-14}$ aryl group(s) optionally substituted by 1 to 3 halogen atoms,
  (d) a $C_{3-8}$ cycloalkyl group, and
  (e) a 3- to 8-membered monocyclic non-aromatic heterocyclic group.

3. The compound or salt of claim 1, wherein $R^1$ is a 3- to 8-membered monocyclic non-aromatic heterocyclic group substituted by one radiolabeled halogen atom.

4. The compound or salt of claim 1, wherein
R¹ is
(1) an azetizinyl group or a pyrrolidinyl group, each substituted by 1 to 3 radiolabeled halogen atoms, or
(2) an amino group mono- or di-substituted by substituent(s) selected from the group consisting of:
(a) a $C_{1-6}$ alkyl group substituted by 1 to 3 radiolabeled halogen atoms, and
(b) a radiolabeled $C_{1-6}$ alkyl group,
and optionally further substituted by a substituent selected from the group consisting of:
(c) a $C_{1-6}$ alkyl group substituted by 1 to 3 halogen atoms,
(d) a $C_{1-6}$ alkyl group optionally substituted by phenyl group(s) optionally substituted by 1 to 3 halogen atoms,
(e) a $C_{3-8}$ cycloalkyl group,
(f) a tetrahydropyranyl group, and
(g) a tetrahydrofuryl group;
R² is
(1) a phenyl group optionally substituted by 1 to 3 halogen atoms, or
(2) a pyrazolyl group or a thiazolyl group, each optionally substituted by 1 to 3 substituents selected from the group consisting of:
(a) a halogen atom,
(b) a $C_{1-6}$ alkyl group, and
(c) a $C_{3-8}$ cycloalkyl group;
X¹ is CH or N; and
Ring A is

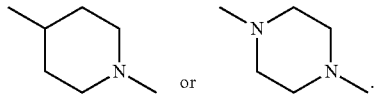

5. The compound or salt of claim 1, wherein
R¹ is
(1) an azetizinyl group or a pyrrolidinyl group, each substituted by one radiolabeled halogen atom, or
(2) an amino group substituted by one substituent selected from the group consisting of:
(a) a $C_{1-6}$ alkyl group substituted by one radiolabeled halogen atom, and
(b) a radiolabeled $C_{1-6}$ alkyl group,
and further substituted by one substituent selected from the group consisting of:
(c) a $C_{1-6}$ alkyl group optionally substituted by phenyl group(s) optionally substituted by 1 to 3 halogen atoms,
(d) a $C_{3-8}$ cycloalkyl group,
(e) a tetrahydropyranyl group, and
(f) a tetrahydrofuryl group;
R² is
(1) a phenyl group optionally substituted by 1 to 3 halogen atoms, or
(2) a pyrazolyl group or a thiazolyl group, each optionally substituted by 1 to 3 substituents selected from the group consisting of:
(a) a halogen atom,
(b) a $C_{1-6}$ alkyl group, and
(c) a $C_{3-8}$ cycloalkyl group;
X¹ is CH or N; and
Ring A is

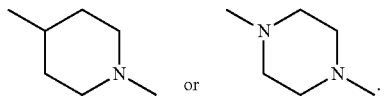

6. The compound or salt of claim 1, wherein
R¹ is an azetizinyl group or a pyrrolidinyl group, each substituted by one radiolabeled halogen atom;
R² is
(1) a phenyl group optionally substituted by 1 to 3 halogen atoms, or
(2) a pyrazolyl group or a thiazolyl group, each optionally substituted by 1 to 3 substituents selected from the group consisting of:
(a) a halogen atom,
(b) a $C_{1-6}$ alkyl group, and
(c) a $C_{3-8}$ cycloalkyl group;
X¹ is CH or N; and
Ring A is

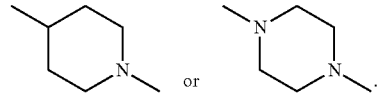

7. The compound or salt of claim 5, wherein R¹ is
(1) an azetizinyl group or a pyrrolidinyl group, each substituted by one $^{18}F$, or
(2) an amino group substituted by one substituent selected from the group consisting of:
(a) a $C_{1-6}$ alkyl group substituted by one $^{18}F$, and
(b) a $C_{1-6}$ alkyl group radiolabeled by one $^{11}C$,
and further substituted by one substituent selected from the group consisting of:
(c) a $C_{1-6}$ alkyl group optionally substituted by phenyl group(s) optionally substituted by 1 to 3 halogen atoms,
(d) a $C_{3-8}$ cycloalkyl group,
(e) a tetrahydropyranyl group, and
(f) a tetrahydrofuryl group.

8. The compound or salt of claim 6, wherein R¹ is an azetizinyl group or a pyrrolidinyl group, each substituted by one $^{18}F$.

9. The compound or salt of claim 1, wherein
R¹ is an azetizinyl group or a pyrrolidinyl group, each substituted by one $^{18}F$;
R² is
(1) a phenyl group optionally substituted by 1 to 3 halogen atoms, or
(2) a pyrazolyl group or a thiazolyl group, each optionally substituted by 1 to 3 substituents selected from the group consisting of:
(a) a halogen atom,
(b) a $C_{1-6}$ alkyl group, and
(c) a $C_{3-8}$ cycloalkyl group;
X¹ is CH or N; and
Ring A is

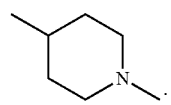

10. (3-[$^{18}F$]Fluoroazetidin-1-yl)(1-(4-(4-fluorophenyl)pyrimidin-5-yl)piperidin-4-yl)methanone or a salt thereof.

11. (1-(4-(4-Chloro-1H-pyrazol-1-yl)pyridin-3-yl)piperidin-4-yl)(3-[$^{18}F$]fluoroazetidin-1-yl)methanone or a salt thereof.

12. (1-(4-(4-Bromo-1H-pyrazol-1-yl)pyridin-3-yl)piperidin-4-yl)(3-[$^{18}$F]fluoroazetidin-1-yl)methanone or a salt thereof.

13. A method for quantitative imaging of cholesterol 24-hydroxylase in a mammal, which comprises administering to the mammal in need of such imaging an effective amount of the compound or salt of claim 1, and obtaining an image useful for quantifying cholesterol 24-hydroxylase in the mammal using positron emission tomography.

14. A method for quantitative imaging of cholesterol 24-hydroxylase in the brain in a mammal, which comprises administering to the mammal in need of such imaging an effective amount of the compound or salt of claim 1, and obtaining an image useful for quantifying cholesterol 24-hydroxylase in the brain in the mammal using positron emission tomography.

15. A method for diagnostic imaging of epilepsy or neurodegenerative disease associated with cholesterol 24-hydroxylase dysfunction in the brain in a mammal, which comprises administering to the mammal in need of such diagnostic imaging an effective amount of the compound or salt of claim 1, and obtaining an image useful for quantifying cholesterol 24-hydroxylase in the brain in the mammal using positron emission tomography.

16. The method of claim 15, wherein the neurodegenerative disease is Alzheimer's disease, mild cognitive disorder, Huntington's disease, Parkinson's disease or multiple sclerosis.

17. A method for the quantification of cholesterol 24-hydroxylase occupancy by a test compound or a salt thereof in mammalian tissue, which comprises contacting such mammalian tissue with an effective amount of the compound or salt of claim 1, contacting such mammalian tissue with the test compound or a salt thereof and quantifying the cholesterol 24-hydroxylase using positron emission tomography.

18. A composition comprising the compound or salt of claim 1.

19. A method of imaging a tissue, cells or a host, which comprises contacting the compound or salt of claim 1, with or administering to a tissue, cells or a host, and imaging the tissue, cells or host with a PET imaging system.

20. The compound or salt of claim 1, which is for use of quantitative imaging of cholesterol 24-hydroxylase.

* * * * *